US005800815A

United States Patent [19]
Chestnut et al.

[11] Patent Number: 5,800,815
[45] Date of Patent: Sep. 1, 1998

[54] ANTIBODIES TO P-SELECTIN AND THEIR USES

[75] Inventors: Robert W. Chestnut, Cardiff; Margaret J. Polley, La Jolla; James C. Paulson, Del Mar, all of Calif.; S. Tarran Jones, Radlett, United Kingdom; José W. Saldanha, Middlesex, United Kingdom; Mary M. Bendig, London, United Kingdom; Michael Kriegler, Rancho Santa Fe, Calif.; Carl Perez, San Diego, Calif.; Robert Bayer, San Diego, Calif.; Michael Nunn, San Diego, Calif.

[73] Assignee: Cytel Corporation, San Diego, Calif.

[21] Appl. No.: 202,047

[22] Filed: Feb. 25, 1994

Related U.S. Application Data

[63] Continuation-in-part of Ser. No. 57,292, May 5, 1993, abandoned, which is a continuation-in-part of Ser. No. 880,198, May 5, 1992, abandoned.

[30] Foreign Application Priority Data

| May 5, 1903 | [IL] | Israel | 105614 |
| May 4, 1993 | [WO] | WIPO | PCT/US93/04274 |

[51] Int. Cl.⁶ ............... A61K 39/395; C07K 16/28; C12N 5/12; C07H 21/04
[52] U.S. Cl. ............... 424/153.1; 424/133.1; 424/143.1; 424/173.1; 435/7.24; 435/70.21; 435/172.2; 435/316; 435/328; 435/343; 435/346; 530/387.3; 530/388.2; 530/388.7; 530/389.6; 536/23.53
[58] Field of Search ............... 424/130.1, 133.1, 424/139.1, 141.1, 143.1, 144.1, 153.1, 173.1, 1.49; 435/70.21, 171.2, 240.27, 69.6, 72.3, 320.1, 326, 328, 331, 332, 334, 343, 346, 2.1, 2.2, 2.21, 2.64; 530/387.1, 387.3, 387.9, 388.1, 388.2, 388.7, 389.6, 391.3; 536/23.5, 23.53

[56] References Cited

U.S. PATENT DOCUMENTS

| 4,605,644 | 8/1986 | Foker | 514/45 |
| 5,114,842 | 5/1992 | Plow et al. | 424/85.8 |
| 5,378,464 | 1/1995 | McEver | 424/143.1 |

FOREIGN PATENT DOCUMENTS

| 101185 | 7/1983 | European Pat. Off. | A61K 9/08 |
| 239400 | 9/1987 | European Pat. Off. | C12N 15/00 |
| 90/07861 | 7/1990 | WIPO | C12P 21/00 |
| 91/06632 | 5/1991 | WIPO | C12N 5/06 |
| 9109967 | 7/1991 | WIPO | |
| WO 92/01718 | 2/1992 | WIPO | C07K 15/00 |

OTHER PUBLICATIONS

Carlos et al., "Membrane proteins involved in phagocyte adherence to endothelium," *Immunol. Reviews* 114:5-28 (1990).

Geng et al., "Rapid neutrophil adhesion to activated endothelium mediated by GMP-140," *Nature* 343:757-760 (1990).

Johnston et al., "Cloning of GMP-140, a granule membrane protein of platelets and endothelium: sequence similarity to proteins involved in cell adhesion and inflammation," *Cell* 56:1033-1044 (1989).

Harris et al., "Therapeutic antibodies—the coming of age," TIBTECH 11:42-44 (1993).

Larsen et al., "PADGEM protein: A receptor that mediates the interaction of activated platelets with neutrophils and monocytes," *Cell* 59:305-312 (1989).

Mulligan et al., "Neutrophil-dependent acute lung injury. Requirement for P-selectin (GMP-140)," *J. Clin. Invest.* 90:1600-1607 (1992).

Parmentier et al., "Inhibition of platelet functions by a monoclonal antibody (LYP20) directed against a granule membrane glycoprotein (GMP-140/PADGEM)," *Blood* 77(8):1734-1739 (1991).

Waldmann, Thomas A., "Monoclonal antibodies in diagnosis and therapy," *Science* 252:1657-1662 (1991).

Kettleborough et al., "Humanization of a mouse monoclonal antibody by CDR-grafting: the importance of framework residues on loop conformation," *Protein Engineering* 4:773-783 (1991).

Aruffo, Alejandro et al., "CD62/P-Selectin Recognition of Myeloid and Tumor Cell Sulfatides." *Cell* 67:35-44 (1991).

Aruffo, Alejandro et al., "Granule Membrane Protein 140 (GMP140) Binds to Carcinomas and Carcinoma-Derived Cell Lines." *Proc. Natl. Acad. Sci. USA.* 89:2292-2295 (1992).

Bevilacqua, Michael P. et al., "Endothelial Leukocyte Adhesion Molecule 1: An Inducible Receptor for Neutrophils Related to Complement Regulatory Proteins and Lectins." *Science* 243:1160-1165 (1989).

Bienvenu, Kristine and Granger, D. Neil "Molecular Determinants of Shear Rate-Dependent Leukocyte Adhesion in Postcapillary Venules." *Am. J. Physiol.* 264:H1504-H1508 (1993).

Bonfanti, Roberta et al., "PADGEM (GMP140) Is a Component of Weibel-Palade Bodies of Human Endothelial Cells." *Blood* 73:1109-1112 (1989).

Borman, Stu "Glycotechnology Drugs Begin to Emerge from the Lab," *C&EN* 27-34 Jun. (1993).

Bowen, Benjamin R. et al., "Characterization of a Human Homologue of the Murine Peripheral Lymph Node Homing Receptor." *J. Cell Biol.* 109:421-427 (1989).

(List continued on next page.)

*Primary Examiner*—Paula K. Hutzell
*Assistant Examiner*—Phillip Gambel
*Attorney, Agent, or Firm*—Campbell & Flores LLP

[57] ABSTRACT

The present invention relates to compositions and methods for treating inflammation and other pathological conditions using novel blocking P-selectin antibodies that inhibit adhesion of leukocytes to activated platelets and/or to activated vascular endothelium in vivo. Both murine and humanized antibodies are provided.

57 Claims, 40 Drawing Sheets

OTHER PUBLICATIONS

Brandley, Brian K. et al., "Carbohydrate Ligands of the LEC Cell Adhesion Molecules." *Cell* 63:861–863 (1990).

Buttrum, Stephen M. et al., "Selectin–Mediated Rolling of Neutrophils on Immobolized Platelets." *Blood* 82:1165–1174 (1993).

Carden, Donna L. et al., "Pulmonary Microvascular Injury After Intestinal Ischemia–Reperfusion: Role of P–Selectin: Role of P–Selectin." 2529–2534 (1993).

Chen, L.Y. et al., "Monoclonal Antibody to P–Selectin (PB1.3) Protects Against Myocardial Reperfusion Injury in the Dog." *Cardiovas. Res.* 28:1414–1422 (1994).

Corral, Laura et al., "Requirement for Sialic Acid on Neutrophils in a GMP–140 (PADGEM) Mediated Adhesive Interaction with Activated Platelets." *Biochem. and Biophysic. Res. Comm.* 172:1349–1356 (1990).

Davenpeck, Kelly L. et al., "Role of P–Selectin in Microvascular Leukocyte–endothelial Interaction in Splanchnic Ischemia–Reperfusion." H622–H630 (1994).

Davenpeck, Kelly L. et al., "Inhibition of Endothelial–Derived Nitric Oxide Promotes P–Selectin Expression and Actions in the Rat Microciculation." *Gastroenterology* 107:1050–1058 (1994).

Doré, Monique et al., "P–Selectin Mediates Spontaneous Leukocyte Rolling In Vivo." *Blood* 82:1308–1316 (1993).

Dunlop, Lindsay C. et al., "Characterization of GMP–140 (P–Selectin) as a Circulating Plasma Protein." *J. Exp. Med.* 175:1147–1150 (1992).

Flynn, David M. et al., "A Blocking Monoclonal Antibody Against P–Selectin Reduces Cardiac Injury Following Myocardial Ischemia and Reperfusion." *FASEB J.* 8:A327 Abstract 1888. (1994).

Gaboury, Jeffrey P. et al., "Molecular Mechanisms Involved in Superoxide–induced Leikocyte–Endothelial Cell Interactions in Vivo." H637–H642 (1994).

Gaboury, Jeffrey P. et al., "Mechanisms Underlying Acute Mast Cell–Induced Leukocyte Rolling and Adhesion In Vivo." *J. Immun.* 154:804–813 (1995).

Gamble, Jennifer R. et al., "Prevention of Activated Neutrophil Adhesion to Endothelium by Soluble Adhesion Protein GMP140." *Science* 249: 414–417 (1990).

Geng, Jian–Guo et al., "Rapid Neutrophil Adhesion to Activated Endothelium Mediated by GMP–140." *Nature* 343:757–760 (1990).

Goelz, Susan E. et al., "ELFT: A Gene That Directs the Expression of an ELAM–1 Ligand" *Cell* 63:1349–1356 (1990).

Grober, James S. et al., "Monocyte–Endothelial Adhesion in Chronic Rheumatoid Arthritis." *J. Clin. Invest.* 91:2609–2619 (1993).

Hamburger, Steven A. and McEver, Rodger P. "GMP–140 Mediates Adhesion of Stimulated Platelets to Neutrophils." *Blood* 75:550–554 (1990).

Hattori, Ryuchi et al., "Stimulated Secretion of Endothelial von Willebrand Factor is Accompanied by Rapid Redistribution of the Cell Surface of the Intracellular Granule Membrane Protein GMP–140." *J. Biol. Chem.* 264:7768–7771 (1989).

Hattori, Ryuchi et al., "Complement Proteins c5b–9 Induce Secretion of High Molecular Weight Multimers of Endothelial von Willebrand Factor and Translocation of Granule Membrane Protein GMP–140 to the Cell Surface." *J. Biol. Chem.* 264:9053–9060 (1989).

Hourcade, Dennis et al., "The Regulators of Complement Activation (RCA) Gene Cluster." *Adv. Immuno.* 45:381–416 (1989).

Hullinger, T.G. et al., "The Effect of P–Selectin Blockade on Neointimal Lesion Development in a Primate Carotoid Injury Model." *FASEB J.* 9:A845 Absract 4897 (1995).

Issekutz, Andrew C. et al., "Role of Neutrophils in the Deposition of Platelets during Acute Inflammation." *Lab. Invest.* 49:716–724 (1983).

Jerome, Sarah N. et al., "P–Selectin and ICAM–1–Dependent Adherence Reactions: Role in the Genesis of Postischemic No–Reflow." H1316–H1321 (1994).

Johnston, G.I. et al., "Structure and Biosynthesis of the Platelet α–Granule Membrane Protein, GMP–140." *Blood* 70:Suppl. 1:355a Abst. No. 1264 (1987).

Johnston, Geoffrey I. et al., "Structure of the Human Gene Encoding Granule Membrane Protein–140, a Member of the Selectin Family of Adhesion Receptors for Leukocytes." *J. Biol. Chem.* 265:21381–21385 (1990).

Johnston, Geoffrey I. et al., "Cloning of GMP–140, Granule Membranes Protein of Platelets and Endothelium: Sequence Similarity to Proteins Involved in Cell Adhesion and Inflammation." *Cell* 56:1033–1044 (1989).

Jones, Peter T. et al., "Replacing the Complementarity–determining Regions in a Human Antibody with Those From a Mouse," *Nature* 321:522–525 (1986).

Langford, E.J. et al., "Inhibition of Platelet Activity by S–Nitrosoglutathione During Coronary Angioplasty." *Lancet* 344:1458–1460 (1994).

Larsen, Eric et al., "PADGEM Protein: A Receptor That Mediates the Interaction of Activated Platelets with Neutrophils and Monocytes." *Cell* 59:305–312 (1989).

Larsen, Eric et al., "PADGEM–Dependent Adhesion of Platelets to Monocytes and Neutrophils is Mediated by a Lineage–Specific Carbohydrate, LNF III (CD15)." *Cell* 63:467–474 (1990).

Lasky, Laurence a. et al., "Cloning of a Lymphocyte Homing Receptor Reveals a Lectin Doamin." *Cell* 56:1045–1055 (1989).

Ley, Klaus "Histamine Can Induce Leukocyte Rolling in Rat Mesenteric Venules." H1017–H1023 (1994).

Liao, Lianxi et al., "Oxidized Lipoproteins Elicit Leukocyte–Endothelial Cell Adhesion in Mesenteric Venules." *FEBS J.* 7:A343 Abst. 1986 (1993).

Lowe, John B. et al., "ELAM–1–Dependent Cell Adhesion to Vascular Endothelium Determined by a Transfected Human Fucosyltransferase cDNA." *Cell* 63:475–484 (1990).

Mayadas, Tanya N. et al., "Leukocyte Rolling and Extavasation Are Severly Compromised in P Selectin–Deficient Mice." *Cell* 74:541–554 (1993).

McEver, Rodger P., "Leukocyte–Endothelial Cell Interactions." *Current Opin. Cell Biol.* 4:840–849 (1992).

McEver, Rodger P. et al., "GMP–140, a Platelet α–Granule Membrane Protein, Is Also Synthesized by Vascular Endothelial Cells and Is Localized in Weibel–Palade Bodies." *J. Clin. Invest.* 84:92–99 (1989).

McEver, R.P. et al., "The Platelet α–Granule Membrane Protein GMP–140 is Also Synthesized by Human Vascular Endothelial Cells and is Present in Blood Vessels of Divers Tissues." *Blood* 70:Suppl. 1:335a Abst. 1274 (1987).

McEver, Rodger P. and Martin, Mary N., "A Monoclonal Antibody to a Membrane Glycoprotein Binds Only to Activated Platelets." *J. Biol. Chem.* 259:9799–9804 (1984).

Moore, Kevin L. et al., "GMP–140 Binds to a Glycoprotein Receptor on Human Neutrophils: Evidence for a Lectin–like Interaction." *J. Cell Biol.* 112:491–499 (1991).

McEver, R.P. "Misguided Leukocyte Adhesion ." *J. Clin. Invest.* 91:2340–2341 (1993).

Müller–Eberhard, Hans J. et al., "Molecular Organization and Function of the Complement System." *Ann. Rev. Biochem.* 57:321–347 (1988).

Mulligan, Michael S. et al., "Neutrophil–Dependent Acute Lung Injury." *J. Clin. Invest.* 90:1600–1607 (1992).

Mulligan, Michael S. et al., "Protective Effects of Oligosaccharides in P–Selectin–Dependent Lung Injury." *Nature* 364:149–151 (1993).

Patel, Kamala D. et al., "Oxygen Radicals Induce Human Endothelial Cells to Express GMP–140 and Bind Neutrophils." *J. Cell Biol.* 112:749–759 (1991).

Phillips, M. Laurie et al., ELAM–1 Mediates Cell Adhesion by Recognition of a Carbohydrates Ligand, Sialyl–Le$^x$. *Science* 250:1130–1132 (1990).

Pigott, Rod and Power, Christine *The Adhesion Molecule FactsBook* Academic Press, (Harcourt Brace & Company, Publ.) London pp. 132–134.

Riechamann, Lutz, et al., "Reshaping Human Antibodies for Therapy." *Nature* 332:323–327 (1988).

Sharar, Sam R. et al., "P–Selectin Blockade Does Not Impair Leukocyte Hose Defense Against Bacterial Peritonitis and Soft Tissue Infections in Rabbits." *J. Immun.* 151:4982–4988 (1993).

Shebuski, Ronald, J. et al., "Role of P–Selectin in Animal Models of Thrombosis and Restenosis." *Circulation* 90:Abstract 0756 (1994).

Siegelman, Mark H. and Weisman, Irving L. "Human Homologue of Mouse Lymph Node Homing Receptor: Evolutionary Conservation at Tandem Cell Interaction Domains." *Proc. Natl. Acad. Sci. USA* 86:5562–5566 (1989).

Siegelman, Mark H. et al., "Mouse Lymph Node Homing Receptor cDNA Clone Encodes a Glycoprotein Revealing Tandem Interaction Domains." *Science* 243:1165–1172 (1989).

Skinner, Michael P. et al., "Characterization of Human Platelet GMP–140 as a Heparin–Binding Protein." *Biochem. Biophys. Res. Commun.* 164:1373–1379 (1989).

Springer, Timothy A. and Lasky, Laurence A. "Sticky Sugars for Selectins." *Nature* 349:196–197 (1991).

Stenberg, Paula E. et al., "A Platelet Alpha–Granule Membrane Protein (GMP–140) Is Expressed on the Plasma Membrane After Activation." *J. Cell Biol.* 101:880–886 (1985).

Suzuki, Hidekazu et al., "Impaired Leukocyte–Endothelial Cell Interaction in Spontaneously Hypertensive Rats." *Hypertension* 24:719–727 (1994).

Tedder, Thomas F. et al., "Isolation and Chromosomal Localization of cDNAs Encoding a Novel Human Lymphocyte Cell Surface Molecule, LAM–1." *J. Exp. Med.* 170:123–133 (1989).

Tenaglia, Alan N. et al., "Beneficial Effect of a P–Selectin Blockade on Endothelial Repair Following Balloon Injury of Rabbit Aorta." *J. Invest. Med.* 43:Supplem. 1 52A (1995).

Tenaglia, Alan N. et al., "Expression of P–Selectin in Human Primary and Restenotic Atherectory." *J. Invest. Med.* 43:Supple 1 7A (1995).

Tiemeyer, Michael et al., "Carbohydrate Ligands for Endothelial–Leukocyte Adhesion Molecule 1." *Proc. Natl. Acad. Sci. USA.* 88:1138–1142 (1991).

Todderud, G. et al., "Soluble GMP–140 Inhibits Neutrophil Accumulation in Induced Murine Peritonitis." *FASEB J.* 6:A1889, Abst. 5513 (1992).

Toombs, C.F. et al., "In Vivo Inhibition of P–Selectin with the GA6 Monoclonal Antibody Accelerates Thrombolysis in a Primate Model of Arterial Thrombosis." *FASEB J.* (Abstr., Part I) 8:A268 (1994).

Verhoeyen, Martine et al., "Reshaping Human Antibodies: Grafting an Antilysozyme Activity." *Science* 239:1534–1536 (1988).

Walz, Gerd, et al., "Recognition by ELAM–1 of the Sialyl–Le$^x$ Determinant on Myeloid and Tumor Cells." *Science* 250:1132–1135 (1990).

Watson, Mark L. et al., "Genomic Organization of the Selectin Family of Leukocyte Adhesion Molecules on Human and Mouse Chromosomes 1." *J. Exp. Med.* 173:263–272 (1990).

Weyrich, Andrew S. et al., "In Vivo Neutralization of P–Selectin Protects Feline Heart and Endothelium in Myocardial Ischemia and Reperfusion Injury." *J. Clin. Invest.* 91:2620–2629 (1993).

Winn, Robert K. et al., "A Monoclonal Antibody to P–Selectin Ameliorates Injury Associated with Hemorrhagic Shock in Rabbits." H2391–H2397 (1994).

Winn, Robert K. et al., "Anti–P–Selectin Monoclonal Antibody Attenuates Reperfusion Injury to the Rabbit Ear." *J. Clin. Invest.* 92:2042–2047 (1993).

Winter, Greg and Milstein, César "Man–made Antibodies." *Nature* 349:293–299 (1991).

Edgington Biotechnology 10:383–389 (1992).

Ward et al. Therapuetic Immunology 1:165–171 (1994).

TRANSLATION OF CY1747 (PB1.3) HEAVY CHAIN SIGNAL PEPTIDE AND
VARIABLE REGION

```
                                                                      48
ATG GGA TGG AGC GGG GTC TTT CTC TTT CTC CTG TCA GGA ACT GCA GGT
Met Gly Trp Ser Gly Val Phe Leu Phe Leu Leu Ser Gly Thr Ala Gly>
```

| SIGNAL SEQUENCE | MATURE VARIABLE REGION SEQUENCE | 96 |

```
GTC CAC TCT | GAG GCC CAG CTG CAG CAG TCT GGA CCT GAG CTG GTA GAG
Val His Ser | Glu Ala Gln Leu Gln Gln Ser Gly Pro Glu Leu Val Glu

144
CCT GGG GCT TCA GTG AAG GTG TCC TGC AAG GCT TCT GGA TAC ACA TTC
Pro Gly Ala Ser Val Lys Val Ser Cys Lys Ala Ser Gly Tyr Thr Phe>

192
ACC AAC TAT GTT ATG CAC TGG GTG AAG CAG AAG CCT GGG CAG GGC CTT
Thr Asn Tyr Val Met His Trp Val Lys Gln Lys Pro Gly Gln Gly Leu>

240
GAG TGG ATT GGA TTT ATT AAC CCA TCC AAT GAT GGT CCT AAG TAC AAT
Glu Trp Ile Gly Phe Ile Asn Pro Ser Asn Asp Gly Pro Lys Tyr Asn>

288
GAG AGG TTC AAA AAC AAG GCC ACA CTG ACT TCA GAC AAA TCC TCC AGC
Glu Arg Phe Lys Asn Lys Ala Thr Leu Thr Ser Asp Lys Ser Ser Ser>

336
ACA GCC TAC ATG GAG CTC AGC AGC CTG ACC TCT GAG GTC TCT GCG GTC
Thr Ala Tyr Met Glu Leu Ser Ser Leu Thr Ser Glu Val Ser Ala Val>

384
TAT TTC TGT GCA AGA GCC CGC CCG GGG TTC GAC TGG TAC TTC GAT GTC
Tyr Phe Cys Ala Arg Ala Arg Pro Gly Phe Asp Trp Tyr Phe Asp Val>

TGG GGC GCA GGG ACC ACG GTC ACC GTC TCC TCA
Trp Gly Ala Gly Thr Thr Val Thr Val Ser Ser
```

FIG. 9

TRANSLATION OF CY1747 (PB1.3) LIGHT CHAIN SIGNAL PEPTIDE AND VARIABLE REGION.

```
                                                                        48
ATG GGC ATC AAG ATG GAG TCA CAG ATT CAG GTC TTT GTA TAC ATG TTG
Met Gly Ile Lys Met Glu Ser Gln Ile Gln Val Phe Val Tyr Met Leu>

SIGNAL
            SEQUENCE       | MATURE VARIABLE REGION SEQ.    96
CTG TGG TTG TCT GGT GTT GAT GGA | GAC ATT GTG ATG ACC CAG TCT CAA
Leu Trp Leu Ser Gly Val Asp Gly | Asp Ile Val Met Thr Gln Ser Gln

144
AAA TTC ATG TCC ACA TCA GTA GGA GAC AGG GTC AGC GTC ACC TGC AAG
Lys Phe Met Ser Thr Ser Val Gly Asp Arg Val Ser Val Thr Cys Lys>

192
GCC AGT CAG AAT GTG GCT ACT AAT GTA GTC TGG TAT CAA CAG AGA CCA
Ala Ser Gln Asn Val Ala Thr Asn Val Val Trp Tyr Gln Gln Arg Pro>

240
GGA CAA TCT CCT AAA GCG CTT ATT TAT ACG GCA TCC TAC CGG TTC AGT
Gly Gln Ser Pro Lys Ala Leu Ile Tyr Thr Ala Ser Tyr Arg Phe Ser>

288
GGA GTC CCT GAA CGC TTC TCA GGC AGT GGA TCT GGG ACA GAT TTC ACT
Gly Val Pro Glu Arg Phe Ser Gly Ser Gly Ser Gly Thr Asp Phe Thr>

336
CTC ACC ATC ACC AAT GTG CAG TCT GAA GAC TTG GCA GAC TAT TTC TGT
Leu Thr Ile Thr Asn Val Gln Ser Glu Asp Leu Ala Asp Tyr Phe Cys>

384
CAA CAA TAT AAC AAC TAT CCC TAC ACG TTC GGA GGG GGG ACC AAG GTG
Gln Gln Tyr Asn Asn Tyr Pro Tyr Thr Phe Gly Gly Gly Thr Lys Val>

GAA ATT CAA
Glu Ile Gln
```

FIG. 10

TRANSLATION OF CY1748 (PB1.3-HUMANIZED) HEAVY CHAIN-A SIGNAL
PEPTIDE AND VARIABLE REGION

```
                                                                          48
ATG GAG TTT GGG CTG AGC TGG CTT TTT CTT GTG GCT ATT TTA

TRANSLATION OF CY1748(PB1.3-HUMANIZED) HEAVY CHAIN-B SIGNAL
PEPTIDE AND VARIABLE REGION

```
                                                                    48
ATG GAG TTT GGG CTG AGC TGG CTT TTT CTT GTG GCT ATT TTA AAA GGT
Met Glu Phe Gly Leu Ser Trp Leu Phe Leu Val Ala Ile Leu Lys Gly>

SIGNAL
SEQUENCE    | MATURE VARIABLE REGION SEQUENCE                      96
GTC CAG TGT | CAG GTC CAG CTG GTG CAG TCT GGA GCT GAG GTG AAA AAG
Val Gln Cys | Gln Val Gln Leu Val Gln Ser Gly Ala Glu Val Lys Lys

144
CCT GGG GCT TCA GTG AAG GTG TCC TGC AAG GCT TCT GGA TAC ACA TTC
Pro Gly Ala Ser Val Lys Val Ser Cys Lys Ala Ser Gly Tyr Thr Phe>

192
ACC AAC TAT GTT ATG CAC TGG GTG CGC CAA GCT CCC GGG CAG AGG CTT
Thr Asn Tyr Val Met His Trp Val Arg Gln Ala Pro Gly Gln Arg Leu>

240
GAG TGG ATG GGA TTT ATT AAC CCA TCC AAT GAT GGT CCT AAG TAC AAT
Glu Trp Met Gly Phe Ile Asn Pro Ser Asn Asp Gly Pro Lys Tyr Asn>

288
GAG AGG TTC AAA AAC AGG GTC ACA ATC ACT TCA GAC ACA TCC GCC AGC
Glu Arg Phe Lys Asn Arg Val Thr Ile Thr Ser Asp Thr Ser Ala Ser>

336
ACC GCC TAC ATG GAA CTG TCC AGC CTG CGC TCC GAG GAC ACT GCA GTC
Thr Ala Tyr Met Glu Leu Ser Ser Leu Arg Ser Glu Asp Thr Ala Val>

384
TAT TAC TGT GCC AGA GCA CGC CCG GGG TTC GAC TGG TAC TTC GAT GTC
Tyr Tyr Cys Ala Arg Ala Arg Pro Gly Phe Asp Trp Tyr Phe Asp Val>

TGG GGA CAG GGT ACC CTT GTC ACC GTC AGT TCA
Trp Gly Gln Gly Thr Leu Val Thr Val Ser Ser
```

FIG. 12

TRANSLATION OF CY1748 (PB1.3-HUMANIZED) HEAVY CHAIN-C SIGNAL
PEPTIDE AND VARIABLE REGION

```
                                                                    48
ATG GAG TTT GGG CTG AGC TGG CTT TTT CTT GTG GCT ATT TTA AAA GGT
Met Glu Phe Gly Leu Ser Trp Leu Phe Leu Val Ala Ile Leu Lys Gly>

SIGNAL
SEQUENCE    | MATURE VARIABLE REGION SEQUENCE                      96
GTC CAG TGT | GAG GCC CAG CTG GTG CAG TCT GGA GCT GAG GTG AAA AAG
Val Gln Cys | Glu Ala Gln Leu Val Gln Ser Gly Ala Glu Val Lys Lys
                                                                   144
CCT GGG GCT TCA GTG AAG GTG TCC TGC AAG GCT TCT GGA TAC ACA TTC
Pro Gly Ala Ser Val Lys Val Ser Cys Lys Ala Ser Gly Tyr Thr Phe>
                                                                   192
ACC AAC TAT GTT ATG CAC TGG GTG CGC CAA GCT CCC GGG CAG AGG CTT
Thr Asn Tyr Val Met His Trp Val Arg Gln Ala Pro Gly Gln Arg Leu>
                                                                   240
GAG TGG ATG GGA TTT ATT AAC CCA TCC AAT GAT GGT CCT AAG TAC AAT
Glu Trp Met Gly Phe Ile Asn Pro Ser Asn Asp Gly Pro Lys Tyr Asn>
                                                                   288
GAG AGG TTC AAA AAC AGG GTC ACA ATC ACT TCA GAC AAA TCC GCC AGC
Glu Arg Phe Lys Asn Arg Val Thr Ile Thr Ser Asp Lys Ser Ala Ser>
                                                                   336
ACC GCC TAC ATG GAA CTG TCC AGC CTG CGC TCC GAG GAC ACT GCA GTC
Thr Ala Tyr Met Glu Leu Ser Ser Leu Arg Ser Glu Asp Thr Ala Val>
                                                                   384
TAT TAC TGT GCC AGA GCA CGC CCG GGG TTC GAC TGG TAC TTC GAT GTC
Tyr Tyr Cys Ala Arg Ala Arg Pro Gly Phe Asp Trp Tyr Phe Asp Val>

TGG GGA CAG GGT ACC CTT GTC ACC GTC AGT TCA
Trp Gly Gln Gly Thr Leu Val Thr Val Ser Ser
```

FIG. 13

TRANSLATION OF CY1748 (PB1.3-HUMANIZED) LIGHT CHAIN-A SIGNAL
PEPTIDE AND VARIABLE REGION

```
                                                                    48
ATG GGA TGG AGC TGT ATC ATC CTC TTC TTG GTA GCA ACA GCT ACA GGT
Met Gly Trp Ser Cys Ile Ile Leu Phe Leu Val Ala Thr Ala Thr Gly>

SIGNAL
SEQUENCE  |  MATURE VARIABLE REGION SEQUENCE                      96
GTC CAC TCC | GAC ATC CAG ATG ACC CAG AGC CCA TCC ACC CTG TCT GCA
Val His Ser | Asp Ile Gln Met Thr Gln Ser Pro Ser Thr Leu Ser Ala
                                                                   144
AGC GTA GGA GAC AGA GTC ACC GTC ACC TGC AAG GCC AGT CAG AAT GTG
Ser Val Gly Asp Arg Val Thr Val Thr Cys Lys Ala Ser Gln Asn Val>
                                                                   192
GCT ACT AAT GTA GTC TGG TAT CAA CAG AAA CCA GGA GAG GCT CCT AAA
Ala Thr Asn Val Val Trp Tyr Gln Gln Lys Pro Gly Glu Ala Pro Lys>
                                                                   240
GCG CTT ATT TAT ACG GCA TCC TAC CGG TTC AGT GGA GTC CCT GAA CGC
Ala Leu Ile Tyr Thr Ala Ser Tyr Arg Phe Ser Gly Val Pro Glu Arg>
                                                                   288
TTC TCA GGC AGT GGA TCT GGG ACA GAT TTC ACT CTC ACC ATC AGC AGT
Phe Ser Gly Ser Gly Ser Gly Thr Asp Phe Thr Leu Thr Ile Ser Ser>
                                                                   336
CTG CAG TCT GAT GAC TTT GCA ACT TAT TAC TGT CAA CAG TAT AAC AAT
Leu Gln Ser Asp Asp Phe Ala Thr Tyr Tyr Cys Gln Gln Tyr Asn Asn>

TAC CCA TAC ACG TTC GGC CAA GGG ACC AAG CTC GAA ATC AAA
Tyr Pro Tyr Thr Phe Gly Gln Gly Thr Lys Leu Glu Ile Lys
```

FIG. 14

TRANSLATION OF CY1748 (PB1.3-HUMANIZED) LIGHT CHAIN-B SIGNAL
PEPTIDE AND VARIABLE REGION

```
                                                              48
ATG GGA TGG AGC TGT ATC ATC CTC TTC TTG GTA GCA ACA GCT ACA GGT
Met Gly Trp Ser Cys Ile Ile Leu Phe Leu Val Ala Thr Ala Thr Gly>
```

| SIGNAL SEQUENCE | MATURE VARIABLE REGION SEQUENCE | 96 |

```
GTC CAC TCC  | GAC ATC CAG ATG ACC CAG AGC CCA TCC ACC CTG TCT GCA
Val His Ser  | Asp Ile Gln Met Thr Gln Ser Pro Ser Thr Leu Ser Ala

144
AGC GTA GGA GAC AGA GTC ACC GTC ACC TGC AAG GCC AGT CAG AAT GTG
Ser Val Gly Asp Arg Val Thr Val Thr Cys Lys Ala Ser Gln Asn Val>

192
GCT ACT AAT GTA GTC TGG TAT CAA CAG AAA CCA GGA GAG GCT CCT AAA
Ala Thr Asn Val Val Trp Tyr Gln Gln Lys Pro Gly Glu Ala Pro Lys>

240
GCG CTT ATT TAT ACG GCA TCC TAC CGG TTC AGT GGA GTC CCT TCA CGC
Ala Leu Ile Tyr Thr Ala Ser Tyr Arg Phe Ser Gly Val Pro Ser Arg>

288
TTC TCA GGC AGT GGA TCT GGG ACA GAT TTC ACT CTC ACC ATC AGC AGT
Phe Ser Gly Ser Gly Ser Gly Thr Asp Phe Thr Leu Thr Ile Ser Ser>

336
CTG CAG TCT GAT GAC TTT GCA ACT TAT TAC TGT CAA CAG TAT AAC AAT
Leu Gln Ser Asp Asp Phe Ala Thr Tyr Tyr Cys Gln Gln Tyr Asn Asn>

TAC CCA TAC ACG TTC GGC CAA GGG ACC AAG CTC GAA ATC AAA
Tyr Pro Tyr Thr Phe Gly Gln Gly Thr Lys Leu Glu Ile Lys
```

FIG. 15

TRANSLATION OF CY1748 (PB1.3-HUMANIZED) LIGHT CHAIN-C SIGNAL
PEPTIDE AND VARIABLE REGION

```
                                                                        48
ATG GGA TGG AGC TGT ATC ATC CTC TTC TTG GTA GCA ACA GCT ACA GGT
Met Gly Trp Ser Cys Ile Ile Leu Phe Leu Val Ala Thr Ala Thr Gly>
```

| SIGNAL SEQUENCE | MATURE VARIABLE REGION SEQUENCE | 96 |

```
GTC CAC TCC | GAC ATC CAG ATG ACC CAG AGC CCA TCC ACC CTG TCT GCA
Val His Ser | Asp Ile Gln Met Thr Gln Ser Pro Ser Thr Leu Ser Ala

144
AGC GTA GGA GAC AGA GTC ACC GTC ACC TGC AAG GCC AGT CAG AAT GTG
Ser Val Gly Asp Arg Val Thr Val Thr Cys Lys Ala Ser Gln Asn Val>

192
GCT ACT AAT GTA GTC TGG TAT CAA CAG AAA CCA GGA GAG GCT CCT AAA
Ala Thr Asn Val Val Trp Tyr Gln Gln Lys Pro Gly Glu Ala Pro Lys>

240
GCG CTT ATT TAT ACG GCA TCC TAC CGG TTC AGT GGA GTC CCT GAA CGC
Ala Leu Ile Tyr Thr Ala Ser Tyr Arg Phe Ser Gly Val Pro Glu Arg>

288
TTC TCA GGC AGT GGA TCT GGG ACA GAA TTC ACT CTC ACC ATC AGC AGT
Phe Ser Gly Ser Gly Ser Gly Thr Glu Phe Thr Leu Thr Ile Ser Ser>

336
CTG CAG TCT GAT GAC TTT GCA ACT TAT TAC TGT CAA CAG TAT AAC AAT
Leu Gln Ser Asp Asp Phe Ala Thr Tyr Tyr Cys Gln Gln Tyr Asn Asn>

TAC CCA TAC ACG TTC GGC CAA GGG ACC AAG CTC GAA ATC AAA
Tyr Pro Tyr Thr Phe Gly Gln Gly Thr Lys Leu Glu Ile Lys
```

FIG. 16

TRANSLATION OF CY1748 (PB1.3-HUMANIZED) LIGHT CHAIN-D SIGNAL
PEPTIDE AND VARIABLE REGION

```
                                                                48
ATG GGA TGG AGC TGT ATC ATC CTC TTC TTG GTA GCA ACA GCT ACA GGT
Met Gly Trp Ser Cys Ile Ile Leu Phe Leu Val Ala Thr Ala Thr Gly>
```

| SIGNAL SEQUENCE | MATURE VARIABLE REGION SEQUENCE |
|---|---|
| GTC CAC TCC<br>Val His Ser | GAC ATC CAG ATG ACC CAG AGC CCA TCC ACC CTG TCT GCA<br>Asp Ile Gln Met Thr Gln Ser Pro Ser Thr Leu Ser Ala |

```
                                                               144
AGC GTA GGA GAC AGA GTC ACC GTC ACC TGC AAG GCC AGT CAG AAT GTG
Ser Val Gly Asp Arg Val Thr Val Thr Cys Lys Ala Ser Gln Asn Val>

192
GCT ACT AAT GTA GTC TGG TAT CAA CAG AAA CCA GGA GAG GCT CCT AAA
Ala Thr Asn Val Val Trp Tyr Gln Gln Lys Pro Gly Glu Ala Pro Lys>

240
GCG CTT ATT TAT ACG GCA TCC TAC CGG TTC AGT GGA GTC CCT TCA CGC
Ala Leu Ile Tyr Thr Ala Ser Tyr Arg Phe Ser Gly Val Pro Ser Arg>

288
TTC TCA GGC AGT GGA TCT GGG ACA GAA TTC ACT CTC ACC ATC AGC AGT
Phe Ser Gly Ser Gly Ser Gly Thr Glu Phe Thr Leu Thr Ile Ser Ser>

336
CTG CAG TCT GAT GAC TTT GCA ACT TAT TAC TGT CAA CAG TAT AAC AAT
Leu Gln Ser Asp Asp Phe Ala Thr Tyr Tyr Cys Gln Gln Tyr Asn Asn>

TAC CCA TAC ACG TTC GGC CAA GGG ACC AAG CTC GAA ATC AAA
Tyr Pro Tyr Thr Phe Gly Gln Gly Thr Lys Leu Glu Ile Lys
```

FIG. 17

- ■ RESHAPED 1748RL VARIABLE REGION
- □ HUMAN KAPPA REGION (GENOMIC DNA FRAGMENT)
- ▨ HCMV DNA FRAGMENT
- ▫ pSV2neo VECTOR FRAGMENT

ANTIBODIES TO P-SELECTIN AND THEIR USES

CROSS-REFERENCE TO RELATED APPLICATIONS

This application is a continuation-in-part of Ser. No. 08/057,292, filed May 5, 1993, now abandoned, which is a continuation-in-part of Ser. No. 07/880,196, filed May 5, 1992, now abandoned. These applications are incorporated by reference in their entirety for all purposes.

TECHNICAL FIELD

This application relates generally to novel immunoglobulins reactive with functional epitopes on a cell surface receptor P-selectin. This application also relates generally to diagnostic and therapeutic methods of using the antibodies.

BACKGROUND OF THE INVENTION

The ability of cells to adhere to one another plays a critical role in development, normal physiology, and disease processes such as inflammation. This ability is mediated by adhesion molecules, generally glycoproteins, expressed on cell membranes. Often, an adhesion molecule on one cell type will bind to another adhesion molecule expressed on a different cell type, forming a receptor counter-receptor pair. Three important classes of adhesion molecules are the integrins, selectins, and immunoglobulin (Ig) superfamily members (see Springer, *Nature* 346:425 (1990); Osborn, *Cell* 62:3 (1990); Hynes, *Cell* 69:11 (1992), all of which are incorporated herein by reference in their entirety for all purposes). These molecules are especially vital to the interaction of leukocytes and platelets with themselves and with the extracellular matrix and vascular endothelium.

P-selectin, also known as CD62, granule membrane protein-140 (GMP-140)/platelet activation-dependent granule external membrane (PADGEM)/LECCAM-3 is a specialized cell-surface receptor on vascular endothelial cells and platelets that is involved in the recognition of various circulating cells. P-selectin is a surface glycoprotein with a lectin-like domain, a region with homology to epidermal growth factor, and a region with homology to complement regulatory proteins (see McEver, *Blood Cells* 16:73–83 (1990)). The structure of P-selectin is similar to that of two other vascular cell surface receptors, endothelial leukocyte adhesion molecule (ELAM-1) and lymphocyte homing receptor (LHR). The term "selectin" has been suggested for this general class of receptors, because of their lectin-like domain and the selective nature of their adhesive functions.

P-selectin is present on the surface of platelets and endothelial cells in response to a variety of stimuli, where it mediates platelet-leukocyte and endothelium-leukocyte interactions. By contrast, ELAM-1 is expressed only on endothelial cells and LHR is expressed on a variety of leukocytes in endothelial venules of peripheral lymph nodes. Expression of P-selectin is inducible and it is not expressed on unactivated endothelial cells or platelets. P-selectin expression does not require de novo synthesis since it is stored in secretory granules (or Weibel-Palade bodies) in both platelets and endothelial cells. Thus, within minutes of activation of either cell type by thrombin, histamine, or phorbol esters or other humoral factors, P-selectin is rapidly redistributed to the surface of the cell where it is accessible for binding to other cells.

A number of mouse antibodies to P-selectin have been reported (see, e.g., U.S. Pat. No. 4,783,330, WO 91/06632, PCT Application No. FR90/00565, McEver et al., *J. Biol. Chem.* 259:9799–9804 (1984)); Geng et al., *Nature* 343:757–760; Parmentier et al., *Blood* 77:1734–1739 (1991)). An additional antibody to P-selectin has been described in presentations at the Scripps Institute, La Jolla Calif. and at a Keystone Colloquium held Jan. 16, 1992. Certain of these antibodies that block P-selectin mediated adhesion are $Ca^{++}$ dependent.

In vitro experiments employing antibodies to P-selectin have provided a limited understanding of the ligand specificity of this receptor. It has been reported that P-selectin binds neutrophils, monocytes and certain carcinoma cells (Bevilacqua et al., *Proc. Natl. Acad. Sci. USA* 84:9238–9242 (1987); Geng et al., *Nature* 343:757–760 (1990); Larsen et al., *Cell* 63:467–474 (1990); and Polley et al. It has been also been reported that P-selectin recognizes $Le^x$ as a high-affinity ligand (Larsen et al., *Cell* 63:467–474 (1990)). However, subsequent experiments showed that $SLe^x$-containing oligosaccharide is in fact a more potent inhibitor of P-selectin mediated adhesion than $Le^x$ (Polley et al., *Proc. Natl. Acad. Sci. USA* 88:6224–6228 (1991)).

The participation of P-selectin in intercellular adhesion in vitro suggests that like other adhesion molecules, P-selectin might participate in cellular interactions that contribute to inflammatory diseases in vivo. However, the specific inflammatory diseases in which P-selectin might play a major role have not yet been elucidated. Similarly, the epitope-specificity of agents effective to abort particular P-selectin-mediated inflammatory diseases is also unclear. Of the known antibodies to P-selectin, some bind to P-selectin but do not block P-selectin mediated intercellular interactions. Other known antibodies have the capacity to block P-selectin-mediated intercellular binding only in the presence of high concentrations of $Ca^{2+}$, a condition that may not always exist in vivo. The absence of high concentrations of $Ca^{2+}$ in vivo would render these antibodies ineffective as therapeutic agents. Moreover, all antibodies to P-selectin produced to-date have been of murine origin and might therefore induce a human-antimouse antibody response (HAMA) in clinical use.

Based on the foregoing it is apparent that a need exists for novel agents targeted against P-selectin that have the appropriate epitope-specificity to abort intercellular interactions leading to inflammatory diseases in vivo. Ideally such agents would not induce a HAMA response in treatment of humans. The present invention fulfills this and other needs.

SUMMARY OF THE INVENTION

In one aspect of the invention, blocking antibodies that specifically bind to P-selectin are provided. One such exemplified antibody is designated mu MAb PB1.3 (produced by a cell line having ATCC accession number HB11041). Other antibodies competitively inhibit the binding of mu MAb PB1.3 to P-selectin measured by a competitive inhibition assay. Preferred antibodies bind to P-selectin in the absence of $Ca^{++}$. The antibodies of the invention include fragments such as Fab, Fab' F(ab')$_2$, Fabc, and Fv, as well as intact antibodies.

In another aspect of the invention, pharmaceutical compositions are provided. The pharmaceutical compositions comprise a blocking P-selectin antibody as described above and a pharmaceutically acceptable carrier.

The invention also provides therapeutic methods for treating diseases of the immune system. The methods comprise administering to a patient having such a disease a therapeutically effective dose of a pharmaceutical composition as described above. Acute lung injury and ischemic reperfusion injury are examples of diseases treatable by the present invention.

Some antibodies of the invention are humanized immunoglobulins. The humanized immunoglobulins comprise a humanized heavy chain and a humanized light chain. The humanized light chain comprises three complementarity determining regions (CDR1, CDR2 and CDR3) having amino acid sequences from the corresponding complementarity determining regions of a mouse PB1.3 immunoglobulin light chain, and a variable region framework from a human kappa light chain variable region framework sequence. The humanized heavy chain comprises three complementarity determining regions (CDR1, CDR2 and CDR3) having amino acid sequences from the corresponding complementarity determining regions of a mouse PB1.3 immunoglobulin heavy chain, and a variable region framework from a human heavy chain variable region framework sequence. The humanized immunoglobulins specifically bind to P-selectin with a binding affinity having a lower limit of about $10^7$ $M^{-1}$ and an upper limit of about five-times the binding affinity of the mouse PB1.3 immunoglobulin.

In many humanized immunoglobulins, the human kappa light chain variable region framework sequence is substituted in at least one position selected from a first group consisting of L21, L46, L60 and L70, by an amino acid present in the equivalent position of the mouse PB1.3 immunoglobulin light chain variable region framework sequence. Similarly, the human heavy chain variable region framework sequence is substituted in at least one position selected from a second group consisting of H1, H2, H71 and H73, by an amino acid present in the equivalent position of the mouse PB1.3 heavy chain variable region framework sequence. In some humanized immunoglobulins, the humanized heavy chain variable region framework is a 21/28'CL heavy chain variable region framework sequence. In some humanized immunoglobulins, the humanized light chain variable region framework is a DEN light chain variable region framework sequence. Exemplary mature light chain variable region amino acid sequences are shown in FIGS. 14-17. Exemplary mature heavy chain variable region amino acid sequences are shown in FIGS. 11-13. A preferred humanized immunoglobulin comprises the mature light chain variable region shown in FIG. 17 and the mature heavy chain variable region shown in FIG. 12.

The invention provides intact humanized immunoglobulins and humanized immunoglobulin fragments such as Fab, Fab' F(ab')$_2$, Fabc and Fv. Some humanized immunoglobulins further comprise a constant region, which may or may not have an effector function.

In another aspect of the invention, nucleic acids encoding the humanized immunoglobulins described above are provided. Some nucleic acid encode heavy chains and others encode light chains.

The invention also provides computers programmed to display a three dimensional representation of the immunoglobulins described above on a monitor or printer.

The invention further provides pharmaceutical compositions comprising the humanized immunoglobulins described above and a pharmaceutically acceptable carrier.

In another aspect, the invention provides methods for detecting P-selectin using the humanized immunoglobulins described above. A humanized immunoglobulin is administered to a patient or a tissue sample therefrom. Complexes formed by specific binding between the immunoglobulin and P-selectin present in the target sample are detected to indicate the presence of P-selectin.

The invention also provides methods of treating a patient suffering from a disease of the immune systems using humanized immunoglobulins. The methods comprise administering to the patient a therapeutically effective dose of a pharmaceutical composition as described above. Diseases amenable to treatment include ischemia-reperfusion injury and acute lung injury. For example, the compositions are useful for treating patients suffering from epidermal, myocardial, renal, cerebral, splenic, hepatic, spinal, splanchnic, pulmonary, partial-body, or whole-body ischemia.

In a further aspect of the invention, stable cell lines producing humanized immunoglobulins are provided. The stable cell lines comprise two nucleic acids segments. One nucleic acid segment encodes the heavy chain of a humanized immunoglobulin as described above, the segment operably linked to a promoter to allow expression of the heavy chain. The second nucleic acid segment encodes the light chain of the humanized immunoglobulin, the second segment operably linked to a second promoter to allow expression of the light chain. Preferred cell lines produce about 30 µg of the humanized immunoglobulin/$10^6$ cells/day.

In another aspect of the invention, fragments of P-selectin are provided. These fragments have up to 100 amino acids, the up to 100 amino acids comprising at least five contiguous amino acids from between positions 448 and 467 of the amino acid sequence shown in FIG. 34. In preferred fragments, the up to 100 amino acids comprise the entire contiguous segment of amino acids between positions 448 and 467.

BRIEF DESCRIPTION OF THE DRAWINGS

FIGS. 3A, 3B, 3C, 3D show expression of P-selectin in lung venules at various times after infusion of CVF; time 0 FIG. 3A, 5, 10 and 15 min, FIGS. 3B, 3C and 3D, respectively. FIGS. 3E, 3F, 3G and 3H are light and transmission electron micrographs of CVF-induced acute lung injury in rats treated with 200 µg non-blocking antibody (mu MAb PNB1.6) (FIGS. 3E and G) or with blocking P-selectin antibody (mu MAb PB1.3) to P-selectin (FIGS. 3F and H). In animals treated with PNB1.6, vascular injury was indicated by extensive intra-alveolar hemorrhage (FIG. 3E), associated with intravascular aggregates of neutrophils (FIG. 3G, arrows) in close contrast with endothelial cells. In contrast, in animals treated with mu MAb PB1.3 intraalveolar hemorrhage was absent (FIG. 3F) and intravascular neutrophils showed little contact with the endothelium (FIG. 3H, arrows). (FIGS. 3E, and F), plastic embedded sections stained with toluidine blue, X160: FIGS. 3G and H, uranyl acetate, lead citrate stained X2250).

Figure 1:
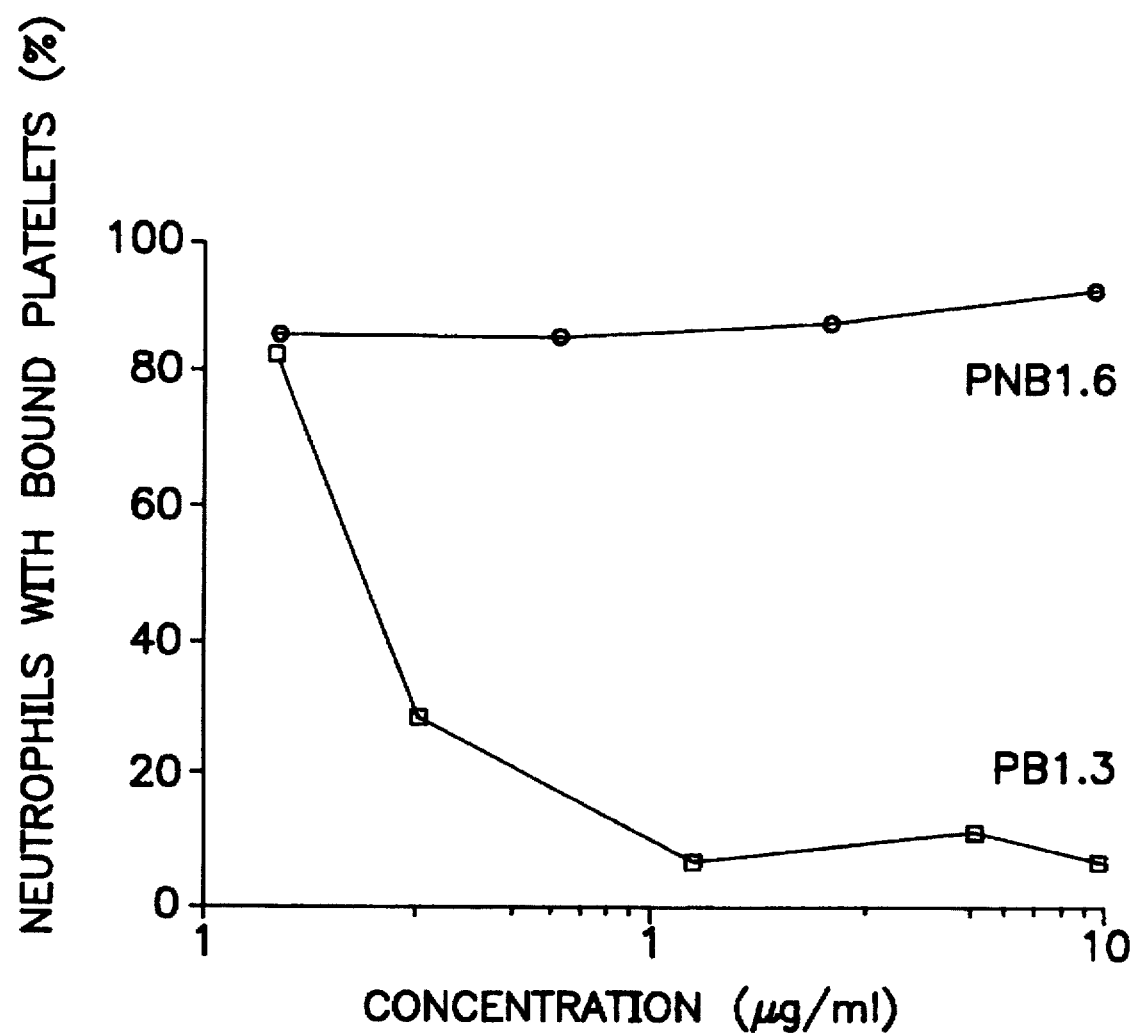
FIG. 1 presents data showing that anti-inflammatory immunoglobulins of the invention inhibit binding of thrombin activated platelets to neutrophils.

The phrase "polynucleotide sequence" refers to a single or double-stranded polymer of deoxyribonucleotide or ribonucleotide bases read from the 5' to the 3' end. It includes self-replicating plasmids, infectious polymers of DNA or RNA and non-functional DNA or RNA.

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence of FIGS. 9–17, or may comprise a complete DNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. (USA)* 85:2444 (1988) (each of which is incorporated by reference in its entirety for all purposes), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of sequence similarity over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, the sequence shown in FIGS. 10–17.

As applied to polypeptides, the term "sequence identity" means peptides share identical amino acids at corresponding positions. The term "sequence similarity" means peptides have identical or similar amino acids (i.e., conservative substitutions) at corresponding positions. The term "substantial identity" means that two peptide sequences, when optimally aligned, such as by the programs GAP or BEST-FIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. The term "substantial similarity" means that two peptide sequences share corresponding percentages of sequence similarity.

The term "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

For purposes of classifying amino acids substitutions as conservative or nonconservative, amino acids are grouped as follows: Group I (hydrophobic sidechains): norleucine, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for another.

Amino acids from the variable regions of the mature heavy and light chains of immunoglobulins are designated Hx and Lxx respectively, where x is a number designating the position of an amino acids according to the scheme of Kabat et al., *Sequences of Proteins of Immunological Interest* (National Institutes of Health, Bethesda, Md. (1987) and (1991)) (hereinafter collectively referred to as "Kabat et al.," incorporated by reference in their entirety for all purposes). Kabat et al. list many amino acid sequences for antibodies for each subclass, and list the most commonly occurring amino acid for each residue position in that subclass. Kabat et al. use a method for assigning a residue number to each amino acid in a listed sequence, and this method for assigning residue numbers has become standard in the field. Kabat et al.'s scheme is extendible to other antibodies not included in the compendium by aligning the antibody in question with one of the consensus sequences in Kabat et al. The use of the Kabat et al. numbering system readily identifies amino acids at equivalent positions in different antibodies. For example, an amino acid at the L50 position of a human antibody occupies the equivalence position to an amino acid position L50 of a mouse antibody.

"Immunoglobulin," "antibody" or "antibody peptide(s)" refers to an intact antibody or a binding fragment thereof that competes with the intact antibody for specific binding to P-selectin.

"Substantial inhibition" means at least about 50% inhibition, preferably about 60% to about 80%, and more usually about greater than 85% or more (as measured in an in vitro competitive binding assay).

Chimeric antibodies are antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as $\gamma_1$ and $\gamma_4$. A typical therapeutic chimeric antibody is thus a hybrid protein consisting of the V or antigen-binding domain from a mouse antibody and the C or effector domain from a human antibody, although other mammalian species may be used.

DESCRIPTION OF THE PREFERRED EMBODIMENT

This invention provides compositions and methods for inhibiting diseases and conditions of the immune system mediated by P-selectin. Specifically, the invention provides immunoglobulins which have the ability to inhibit P-selectin-mediated adhesion of cells in vivo.

I. Characteristics of Immunoglobulins

A. General

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Immunology* (Paul, W., ed., 2nd ed. Raven Press, N.Y., 1989), Ch. 7 (incorporated by reference in its entirety for all purposes).

The variable regions of each light/heavy chain pair form the antibody binding site. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. CDR and FR residues are delineated according to the standard sequence definition of Kabat et al., supra. An alternative structural definition has been proposed by Chothia et al., *J. Mol. Biol.* 196:901–917 (1987); *Nature* 342:878–883 (1989); and *J. Mol. Biol.* 186:651–663 (1989) (hereinafter collectively referred to as "Chothia et al." and incorporated by reference in their entirety for all purposes).

B. Binding Specificity and Affinity

The immunoglobulins (or antibodies) of the invention selectively bind a functional epitope on P-selectin associated with a response to tissue injury and inflammation. Usually, binding of the antibodies to a functional epitope on P-selectin effectively inhibits adhesion of leukocytes to activated platelets and/or to the activated vascular endothelium in vivo. Antibodies showing this property are referred to as "blocking" antibodies. Preferred blocking antibodies impair the adhesion of leukocytes to the activated vascular endothelium to prevent or inhibit an inflammatory and/or thrombotic condition.

Many of the blocking antibodies of the invention compete with an exemplary antibody designated mu MAb PB1.3 for specific binding to P-selectin. A hybridoma producing the mu MAb PB1.3 antibody has been deposited with the AMERICAN TYPE CULTURE COLLECTION, Rockville, Md. under the Budapest Treaty on May 14, 1992 and given the Accession No. HB11041. The production of this monoclonal antibody is described in Example 1. Other blocking antibodies of the invention compete with a second exemplified antibody designated 84/26.

Competition is determined by an assay in which the immunoglobulin under test inhibits specific binding of a reference antibody (e.g., mu MAb PB1.3) to an antigenic determinant on a P-selectin molecule. Numerous types of competitive binding assays are known for example: solid phase direct or indirect radioimmunoassay (RIA), solid phase direct or indirect enzyme immunoassay (EIA), sandwich competition assay (see Stahli et al., *Methods in Enzymology* 9:242–253 (1983)); solid phase direct biotin-avidin EIA (see Kirkland et al., *J. Immunol.* 137:3614–3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using I-125 label (see Morel et al., *Molec. Immunol.* 25(1):7–15 (1988)); solid phase direct biotin-avidin EIA (Cheung et al., *Virology* 176:546–552 (1990)); and direct labeled RIA (Moldenhauer et al., *Scand. J. Immunol.* 32:77–82 (1990)). Typically, such an assay involves the use of purified P-selectin or cells bearing P-selectin bound to a solid surface, an unlabelled test immunoglobulin and a labelled reference immunoglobulin. Competitive inhibition is measured by determining the amount of label bound to the solid surface in the presence of the test immunoglobulin. Usually the test immunoglobulin is present in excess. An example of a suitable competitive binding assay is presented in Example 8. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to P-selectin by at least 10, 25, 50 or 75%.

The epitope bound by mu MAb PB1.3 has been mapped to an epitope between amino acids 448 and 467 of human P-selectin. See FIG. 34 and Johnson et al., *Cell* 56:1033–1044 (1989) (hereby incorporated by reference in its entirety for all purposes). The epitope occurs within the fifth CRP domain of P-selectin. See FIG. 30. Antibodies that compete with mu MAb PB1.3 usually bind to a segment of amino acids between 448 and 467 or to another segment within the fifth CRP domain.

The binding specificity of many blocking antibodies of the invention is further defined by their capacity to bind P-selectin in the complete or substantial absence of $Ca^{++}$ (e.g., in the presence of 25 mM EDTA (a calcium chelator) and the absence of $Ca^{++}$ in an in vitro assay). Antibodies requiring a $Ca^{++}$ cofactor for blocking activity may not be effective in in vivo conditions where levels of $Ca^{++}$ are expected to fluctuate.

Antibodies that compete with the mu MAb PB1.3 antibody are further characterized by the observation that their capacity to specifically bind to P-selectin is not inhibited by a fragment of P-selectin having the amino acid sequence CQNRYTDLVAIQNKNE (SEQ ID No: 1). A molar excess of this fragment usually inhibits specific binding of such antibodies by less than 5%. Mu MAb PB1.3 and competing antibodies are thereby distinguished from reported mouse antibodies designated G1, G2 and G3 (Geng et al., *The Journal of Biological Chemistry* 266:22313–22318 (1991)) whose binding to P-selectin is partially or completely blocked by the above peptide.

Some antibodies of the invention are further characterized by their capacity to selectively inhibit some P-selectin mediated responses while leaving others unimpaired. For example, some antibodies are capable of blocking specific binding of neutrophils to activated endothelial cells in vivo, without inhibiting platelet aggregation. Such antibodies are particularly useful for treating inflammatory disorders without impairing a patient's capacity to initiate a response to conditions (e.g., wounding) in which platelet aggregation is desirable.

The antibodies of the invention usually exhibit a specific binding affinity for P-selectin of at least $10^7$, $10^8$, $10^9$, or $10^{10}$ $M^{-1}$. Usually the upper limit of binding affinity of the antibodies for P-selectin is within a factor of about three, five or ten of that of the mu MAb PB 1.3.1. Often the lower limit of binding affinity is also within a factor of about three, five or ten of that of mu MAb PB1.3. In this context, the term "about" encompasses the small degree of experimental error that may typically occur in the measurement of binding affinities.

II. Production of Immunoglobulins

A. Nonhuman Antibodies

The production of non-human monoclonal antibodies, e.g., murine, lagomorpha, equine is well known and can be accomplished by, for example, immunizing an animal with a preparation containing cells bearing P-selectin (e.g., thrombin-activated platelets), isolated P-selectin molecules or fragments thereof, such as extracellular domains. Antibody-producing cells obtained from the immunized animals are immortalized and screened, or screened first for the production of antibody which binds to P-selectin, and then immortalized. See Harlow and Lane, supra. Alternatively, substantially monospecific antibody populations can be produced by chromatographic purification of polyclonal sera.

B. Human Antibodies Against P-Selectin

In another aspect of the invention, human antibodies against P-selectin are provided. Some human antibodies are selected by competitive binding experiments, or otherwise, to have the same epitope specificity as a particular mouse antibody, such as mu MAb PB1.3. Such antibodies are particularly likely to share the useful therapeutic properties demonstrated for mu MAb PB1.3. Human antibodies to P-selectin can be produced by screening a DNA library from human B cells according to the general protocol outlined by Huse et al., *Science* 246:1275–1281 (1989). Antibodies binding to P-selectin or a fragment thereof are selected. Sequences encoding such antibodies (or a binding fragments) are then cloned and amplified. The protocol described by Huse is rendered more efficient in combination with phage-display technology. See, e.g., Dower et al., WO 91/17271 and McCafferty et al., WO 92/01047 (each of which is incorporated by reference in its entirety for all purposes). In these methods, libraries of phage are produced in which members display different antibodies on their outersurfaces. Antibodies are usually displayed as Fv or Fab fragments. Phage displaying antibodies with a desired specificity are selected by affinity enrichment to an P-selectin polypeptide or fragment thereof.

In a variation of the phage-display method, human antibodies having the binding specificity of a selected murine antibody can be produced. See Winter, WO 92/20791. In this method, either the heavy or light chain variable region of the selected murine antibody (e.g., mu MAb PB1.3) is used as a starting material. If, for example, a light chain variable region is selected as the starting material, a phage library is constructed in which members displays the same light chain variable region (i.e., the murine starting material) and a different heavy chain variable region. The heavy chain variable regions are obtained from a library of rearranged human heavy chain variable regions. A phage showing strong specific binding for P-selectin (e.g., at least $10^8$ and preferably at least $10^9$ $M^{-1}$) is selected. The human heavy chain variable region from this phage then serves as a starting material for constructing a further phage library. In this library, each phage displays the same heavy chain variable region (i.e., the region identified from the first display library) and a different light chain variable region. The light chain variable regions are obtained from a library of rearranged human variable light chain regions. Again, phage showing strong specific binding for L-selectin are selected. These phage display the variable regions of completely human anti-P-selectin antibodies. These antibodies usually have the same or similar epitope specificity as the murine starting material (e.g., mu MAb PB1.3).

C. Humanized Antibodies

The invention provides humanized immunoglobulins having variable framework regions substantially from a human immunoglobulin (termed an acceptor immunoglobulin) and complementarity determining regions substantially from a mouse immunoglobulin termed mu MAb PB1.3 (referred to as the donor immunoglobulin). The constant region(s), if present, are also substantially from a human immunoglobulin. The humanized antibodies of the present invention offer several advantages over the mouse donor antibody, which has already shown to be effective in animals models:

1) The human immune system should not recognize the framework or constant region of the humanized antibody as foreign, and therefore the antibody response against such an injected antibody should be less than against a totally foreign mouse antibody or a partially foreign chimeric antibody.

2) Because the effector portion of the humanized antibody is human, it may interact better with other parts of the human immune system.

3) Injected mouse antibodies have been reported to have a half-life in the human circulation much shorter than the half-life of normal human antibodies (Shaw et al., *J. Immunol.* 138:4534–4538 (1987)). Injected humanized antibodies have a half-life essentially equivalent to naturally occurring human antibodies, allowing smaller and less frequent doses.

1. Cloning and Sequencing Variable Domains of mu MAb PB1.3

The cloning and sequencing of cDNA encoding the mu MAb PB1.3 antibody heavy and light chain variable regions is described in Example 10, and the nucleotide and predicted amino acids sequences are shown in FIGS. 11 and 12. Tables 1 (mouse II A=SEQ ID No. 21, human I=SEQ ID No. 22, human 21/28'CL=SEQ ID No. 23) and 2 (mouse κ-V=SEQ ID No. 24, human κ-I=SEQ ID No. 25, human DEN=SEQ ID No. 26) illustrate the subdivision of the amino acid coding sequence into framework and complementarity determining domains. From N-terminal to C-terminal, both light and heavy chains comprise the domains FR1, CDR1, FR2, CDR2, FR3, CDR3 and FR4. The assignment of amino acids to each domain is in accordance with the numbering convention of Kabat et al., supra.

(2) Selection of Human Antibodies to Supply Framework Residues

The substitution of mouse CDRs into a human variable domain framework is most likely to result in retention of their correct spatial orientation if the human variable domain framework adopts the same or similar conformation to the mouse variable framework from which the CDRs originated. This is achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. See Kettleborough et al., Protein Engineering 4:773 (1991); Kolbinger et al., Protein Engineering 6:971 (1993).

Suitable human antibody sequences are identified by computer comparisons of the amino acid sequences of the mouse variable regions with the sequences of known human antibodies. The comparison is performed separately for heavy and light chains but the principles are similar for each. This comparison reveals that the mu MAb PB1.3 light chain shows greatest sequence identity to human light chains of subtype kappa-1 and that the mu PB1.3 heavy chain shows greatest sequence identity to human heavy chains of subtype 1, as defined by Kabat et al., supra. Thus, light and heavy human framework regions are usually derived from human antibodies of these subtypes, or from consensus sequences of such subtypes. The preferred heavy and light chain human variable regions showing greatest sequence identity to the corresponding regions from mu MAb PB1.3 are from antibodies 21/28' CL and DEN respectively.

(3) Computer Modelling

The unnatural juxtaposition of murine CDR regions with human variable framework region can result in unnatural conformational restraints, which, unless corrected by substitution of certain amino acid residues, lead to loss of binding affinity. The selection of amino acid residues for substitution is determined, in part, by computer modelling. Computer hardware and software for producing three-dimensional images of immunoglobulin molecules are widely available. In general, molecular models are produced starting from solved structures for immunoglobulin chains or domains thereof. The chains to be modelled are compared for amino acid sequence similarity with chains or domains of solved three dimensional structures, and the chains or domains showing the greatest sequence similarity is/are selected as starting points for construction of the molecular model. For example, for the light chain of mu MAb PB1.3, the starting point for modelling was the human light chain DEN. The solved starting structures are modified to allow for differences between the actual amino acids in the immunoglobulin chains or domains being modelled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits. Such a model can in turn serve as a starting point for predicting the three-dimensional structure of an antibody containing the mu MAb PB1.3 complementarity determining regions substituted in human framework structures. Additional models can be constructed representing the structure when further amino acid substitutions to be discussed infra, are introduced.

(4) Substitution of Amino Acid Residues

As noted supra, the humanized antibodies of the invention comprise variable framework regions substantially from a human immunoglobulin and complementarity determining regions substantially from a mouse immunoglobulin termed mu MAb PB1.3. Having identified the complementarity determining regions of mu MAb PB1.3 and appropriate human acceptor immunoglobulins, the next step is to determine which, if any, residues from these components should be substituted to optimize the properties of the resulting humanized antibody. In general, substitution of human amino acid residues with murine should be minimized, because introduction of murine residues increases the risk of the antibody eliciting a HAMA response in humans. Amino acids are selected for substitution based on their possible influence on CDR conformation and/or binding to antigen. Investigation of such possible influences is by modelling, examination of the characteristics of the amino acids at particular locations, or empirical observation of the effects of substitution or mutagenesis of particular amino acids.

When an amino acid differs between a mu MAb PB1.3 variable framework region and an equivalent human variable framework region, the human framework amino acid should usually be substituted by the equivalent mouse amino acid if it is reasonably expected that the amino acid:

(1) noncovalently binds antigen directly (e.g., amino acids at positions H1, H2, and L60 of mu MAb PB1.3)

(2) is adjacent to a CDR region, is part of a CDR region under the alternative definition proposed by Chothia et al., supra, or otherwise interacts with a CDR region (e.g., is within about 3 Å of a CDR region) (e.g., H73 of mu MAb PB1.3, Tables 1 and 3), or (3) participates in the $V_L$-$V_H$ interface.

Other candidates for substitution are acceptor human framework amino acids that are unusual for a human immunoglobulin at that position. These amino acids can be substituted with amino acids from the equivalent position of more typical human immunoglobulins. Alternatively, amino acids from equivalent positions in mu MAb PB1.3 can be introduced into the human framework regions when such amino acids are typical of human immunoglobulin at the equivalent positions.

In general, substitution of all or most of the amino acids fulfilling the above criteria is desirable. Occasionally, however, there is some ambiguity about whether a particular amino acid meets the above criteria, and alternative variant immunoglobulins are produced, one of which has that particular substitution, the other of which does not. Surprisingly, an exemplified humanized antibody designated reshaped MAb PB1.3 ($H_D L_D$) contains only one substitution of the human heavy-chain variable region framework residues and only two substitutions of the human light-chain variable region framework residues and yet exhibits substantially similar (within a factor of two) binding affinity to a murine or chimeric antibody having intact murine variable regions fused to a human constant region (designated chi MAb PB1.3).

Some humanized antibodies of the invention contain a substitution of a human light chain framework residue with a corresponding mu MAb PB1.3 residue in at least 1, 2 or 3, and sometimes 4 of the following positions: L21, L46, L60 and L70. (See Tables 2 and 4). Some humanized antibodies usually contain a substitution of a human heavy chain framework residue in at least 1, 2 or 3 and sometimes 4 of the following positions H1, H2, and H71 and H73. (See Tables 1 and 3). Many humanized antibodies contain substitutions of both light and heavy chain variable framework regions. Preferred antibodies contain a substitution of a human heavy chain framework residue at least at position H71, and substitutions of human light chain framework residues at least at positions 21 and 46.

Usually the CDR regions in humanized antibodies are substantially identical, and more usually, identical to the corresponding CDR regions in the mu MAb PB1.3 antibody. Although not usually desirable, it is sometimes possible to make one or more conservative amino acid substitutions of CDR residues without appreciably affecting the binding affinity of the resulting humanized immunoglobulin. Occasionally, substitution of CDR regions can result in enhanced binding affinity.

Other than for the specific amino acid substitutions discussed above, the framework regions of humanized immunoglobulins are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin. However, in general, such substitutions are undesirable.

(5) Production of Variable Regions

Having conceptually selected the CDR and framework components of humanized immunoglobulins, a variety of methods are available for producing such immunoglobulins. Because of the degeneracy of the code, a variety of nucleic acid sequences will encode each immunoglobulin amino acid sequence. The desired nucleic acid sequences can be produced by de novo solid-phase DNA synthesis or by PCR mutagenesis of an earlier prepared variant of the desired polynucleotide. Oligonucleotide-mediated mutagenesis is a preferred method for preparing substitution, deletion and insertion variants of target polypeptide DNA. See Adelman et al., *DNA* 2:183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

(6) Selection of Constant Region

The variable segments of humanized antibodies produced as described supra are typically linked to at least a portion of an immunoglobulin constant region (Fc), typically that of a human immunoglobulin. Human constant region DNA sequences can be isolated in accordance with well-known procedures from a variety of human cells, but preferably immortalized B-cells (see Kabat et al., supra, and WO87/02671) (each of which is incorporated by reference in its entirety for all purposes). Ordinarily, the antibody will contain both light chain and heavy chain constant regions. The heavy chain constant region usually includes CH1, hinge, CH2, CH3, and CH4 regions.

The humanized antibodies include antibodies having all types of constant regions, including IgM, IgG, IgD, IgA and IgE, and any isotype, including IgG1, IgG2, IgG3 and IgG4. When it is desired that the humanized antibody exhibit cytotoxic activity, the constant domain is usually a complement-fixing constant domain and the class is typically $IgG_1$. When such cytotoxic activity is not desirable, the constant domain may be of the $IgG_4$ class. The humanized antibody may comprise sequences from more than one class or isotype.

(7) Expression Systems

Nucleic acids encoding humanized light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Such control sequences include a signal sequence, a promoter, an enhancer, and a transcription termination sequence. Expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362).

*E. coli* is one prokaryotic host useful particularly for cloning the polynucleotides of the present invention. Other microbial hosts suitable for use include bacilli, such as *Bacillus subtilus*, and other enterobacteriaceae, such as Salmonella, Serratia, and various Pseudomonas species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. Saccharomyces is a preferred host, with suitable vectors having expression control sequences, such as promoters, including 3-phosphoglycerate kinase or other glycolytic enzymes, and an origin of replication, termination sequences and the like as desired.

In addition to microorganisms, mammalian tissue cell culture may also be used to express and produce the polypeptides of the present invention (see Winnacker, *From Genes to Clones* (VCH Publishers, N.Y., N.Y., 1987). Eukaryotic cells are actually preferred, because a number of suitable host cell lines capable of secreting intact immunoglobulins have been developed. Preferred suitable host cells for expressing nucleic acids encoding the immunoglobulins of the invention include: monkey kidney CV1 line transformed by SV40 (COS-7, ATCC CRL 1651); human embryonic kidney line (293) (Graham et al., *J. Gen. Virol.* 36:59 (1977)); baby hamster kidney cells (BHK, ATCC CCL 10);

Chinese hamster ovary-cells-DHFR (CHO, Urlaub and Chasin, *Proc. Natl. Acad. Sci. (USA)* 77:4216 (1980)); mouse sertoli cells (TM4, Mather, *Biol. Reprod.* 23:243–251 (1980)); monkey kidney cells (CV1 ATCC CCL 70); african green monkey kidney cells (VERO-76, ATCC CRL 1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); and, TRI cells (Mather, et al., *Annals N.Y. Acad. Sci.* 383:44–46 (1982)); baculovirus cells.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts. (See generally Sambrook et al., *Molecular Cloning: A Laboratory Manual* (Cold Spring Harbor Press, 2nd ed., 1989) (incorporated by reference in its entirety for all purposes). When heavy and light chains are cloned on separate expression vectors, the vectors are cotransfected to obtain expression and assembly of intact immunoglobulins. After introduction of recombinant DNA, cell lines expressing immunoglobulin products are cell selected. Cell lines capable of stable expression are preferred (i.e., undiminished levels of expression after fifty passages of the cell line).

Once expressed, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like (see generally *Scopes, Protein Purification* (Springer-Verlag, N.Y., 1982). Substantially pure immunoglobulins of at least about 90 to 95% homogeneity are preferred, and 98 to 99% or more homogeneity most preferred, for pharmaceutical uses.

The recombinant techniques described above can also be used for expression of native sequences encoding human or murine antibodies. This approach is particularly advantageous for expression of human antibodies that are isolated as unstable cell lines.

III. Antibodies Fragments

In another embodiment of the invention, fragments of the intact antibodies described above are provided. Typically, these fragments compete with the intact antibody from which they were derived for specific binding to P-selectin, and bind with an affinity of at least $10^7$, $10^8$, $10^9$ $M^{-1}$, or $10^{10}$ $M^{-1}$. Antibody fragments include separate heavy chains, light chains Fab, Fab' F(ab')$_2$, Fabc, and Fv. Fragments can be produced by enzymic or chemical separation of intact immunoglobulins. For example, a F(ab')$_2$ fragment can be obtained from an IgG molecule by proteolytic digestion with pepsin at pH 3.0–3.5 using standard methods such as those described in Harlow and Lane, *Antibodies: A Laboratory Manual*, Cold Spring Harbor Pubs., N.Y. (1988). Fab fragments may be obtained from F(ab')$_2$ fragments by limited reduction, or from whole antibody by digestion with papain in the presence of reducing agents. (See id.) Fragments can also be produced by recombinant DNA techniques. Segments of nucleic acids encoding selected fragments are produced by digestion of full-length coding sequences with restriction enzymes, or by de novo synthesis. Often fragments are expressed in the form of phage-coat fusion proteins. This manner of expression is advantageous for affinity-sharpening of antibodies as discussed in Section IV.

IV. Affinity-Sharpened Antibodies

Many of the immunoglobulins described above can undergo non-critical amino-acid substitutions, additions or deletions in both the variable and constant regions without loss of binding specificity or effector functions, or intolerable reduction of binding affinity (i.e., below about $10^7$ $M^{-1}$). Usually, immunoglobulins incorporating such alterations exhibit substantial sequence identity to a reference immunoglobulin from which they were derived. Occasionally, a mutated immunoglobulin can be selected having the same specificity and increased affinity compared with a reference immunoglobulin from which it was derived. Phage-display technology offers powerful techniques for selecting such immunoglobulins. See, e.g., Dower et al., WO 91/17271 McCafferty et al., WO 92/01047; and Huse, WO 92/06204.

V. Hybrid Antibodies

The invention also provides hybrid antibodies that share the specificity of blocking antibodies against P-selectin but are also capable of specific binding to a second moiety. In hybrid antibodies, one heavy and light chain pair is usually from an anti-P-selectin antibody and the other pair from an antibody raised against another epitope. This results in the property of multi-functional valency, i.e., ability to bind at least two different epitopes simultaneously, where at least one epitope is the epitope to which the blocking P-selectin antibody binds. Such hybrids can be formed by fusion of hybridomas producing the respective component antibodies, or by recombinant techniques.

Immunoglobulins can also be fused to functional regions from other genes (e.g., enzymes) to produce fusion proteins (e.g., immunotoxins) having novel properties.

VI. Nucleic Acids

The intact antibodies and antibody fragments described above are often produced by expression of nucleic acids. All nucleic acids encoding any antibody or antibody described in this application are expressly included in the invention. Modifications of nucleic acids are readily accomplished by a variety of well-known techniques, such as site-directed mutagenesis (see Gillman and Smith, *Gene*, 8:81–97 (1979) and Roberts, et al., *Nature*, 328:731–734 (1987)). Many of the nucleic acids of the invention show substantial sequence identity to nucleic acids encoding the heavy and light chains of mu MAb PB1.3 or the exemplified humanized derivatives thereof.

VII. Computers

In another aspect of the invention, computers programmed to display three dimensional images of antibodies on a monitor or printer are provided. For example, a SILICON GRAPHICS IRIS 4D workstation running under the UNIX operating system and using the molecular modelling package QUANTA (POLYGEN CORP. USA) is suitable. Computers are useful for visualizing models of variants of humanized antibodies. In general, the antibodies of the invention already provide satisfactory binding affinity. However, it is likely that antibodies with even stronger binding affinity could be identified by further variation of certain amino acid residues. The three dimensional image will also identify many noncritical amino acids, which could be the subject of conservative substitutions without appreciable affecting the binding affinity of the antibody.

VIII. Large-Scale Production of Antibodies

For large-scale production of antibodies, stable cells are produced containing multiple copies of the genes encoding heavy and light chain immunoglobulins in their chromosomes. Multiple copies are obtained by amplification of isolated region(s) of a cell's chromosomal DNA. Amplification is achieved using a selection agent, e.g., methotrexate (MTX), that inactivates a cellular enzyme (e.g., DHFR) that is essential under certain growth conditions. Amplification, i.e., the accumulation of multiple copies of the DHFR gene, results in greater amounts of DHFR being produced in response to greater amounts of MTX. Amplification pressure is applied notwithstanding the presence of endogenous DHFR, by adding ever greater amounts of MTX to the media. Amplification of desired genes (here genes encoding immunoglobulin heavy and light chains) is achieved by linking each gene to a copy of a DHFR gene on the same or separate plasmid(s), and cotransfecting the plasmid(s). Amplification of the DHFR genes in response to MTX results in a concomitant increase in copy number of the desired immunoglobulin genes. Increased copy number of the desired genes results in greater expression of the desired heterologous protein. Stable cell lines expressing about 10–100, 20–50 or about 30 μg humanized immunoglobulin per $10^6$ cells per day are preferred.

IX. P-Selectin Fragments

In another aspect of the invention, fragments of P-selectin are provided. The fragments comprise amino acids from the fifth C3b–C4b regulatory domain of P-selectin (fifth CRP). The fragments contain the epitope bound by mu MAb PB 1.3 and/or proximal epitopes bound by competing antibodies. The fragments usually contain up to 5, 10, 20, 25, 50, 75, 100 or 200 amino acids in total. Most fragments contain some or all of the amino acids between positions 448 and 467 of the human P-selectin sequence shown in FIG. 34. These amino acids define the epitope specifically bound by mu MAb PB1.3. In many fragments, at least five contiguous amino are from between positions 448 and 467 of the amino acid sequence shown in FIG. 34. Other fragments contain the entire contiguous segment of amino acids between positions 448 and 467. Some fragments consist essentially of this contiguous segment of amino acids. In these fragments, no other amino acids are present that contribute to the binding specificity or affinity of the fragment. Often, no other amino acids of any description are present.

The polypeptide fragments of the invention have a variety of uses. The fragments are useful as immunogens for generating antibodies that compete with mu MAb PB 1.3 for specific binding to P-selectin. The use of defined fragments as immunogens reduces the extent of screening required to isolate an antibody of desired specificity. The polypeptide fragments are also useful in the diagnostic and therapeutic methods described infra. Some fragments compete with full-length P-selectin molecules for binding to activated neutrophils. Thus, these fragments are useful for aborting diseases and conditions of the immune system mediate by interactions of P-selectin with its ligand(s) on activated neutrophils. Some fragments are also useful for monitoring the presence of activated neutrophils by binding to ligands to P-selectin present on the surface of these cells. The small size of the fragments renders them particularly suitable for effective delivery following in vivo administration. The exclusively human origin of the fragments reduces the risk of side-effects that might occur with some other agents.

X. Therapeutic and Diagnostic Methods

The therapeutic methods employ the antibodies (whole and binding fragments), and fragments of P-selectin discussed above as therapeutic agents for treatment of various diseases. The therapeutic agents are useful for prophylactic and therapeutic treatment of a wide variety of diseases and disorders of the immune system. Such diseases and disorders include transplant rejection, graft versus host disease, autoimmune diseases such as insulin-dependent diabetes mellitus, multiple sclerosis, stiff man syndrome, rheumatoid arthritis, myasthenia gravis and lupus erythematosus, and inflammatory disorders. The agents are also useful for preventing tumor metastasis inhibiting the adhesion of circulating cancer cells, such as carcinomas of the colon and melanoma. Some therapeutic agents function by blocking or otherwise antagonizing the action of a P-selectin molecule with its ligand. Other therapeutic agents function by killing cells bearing a polypeptide against which the agent is targeted.

The therapeutic agents are particularly suitable for treatment of inflammatory and thrombotic conditions including post-ischemic leukocyte-mediated tissue damage (reperfusion injury) arising from traumatic shock, stroke, myocardial infarction, acute transplantation rejection, frost-bite injury, compartment syndrome, and pathophysiologic conditions associated with cardio-pulmonary bypass, acute leukocyte-mediated lung injury (e.g., adult respiratory distress syndrome), septic shock, wound associated sepsis secondary to viral infection by e.g., herpes simplex virus, IgE-mediated allergic reactions such as acute phase asthmatic disease, and chronic inflammatory conditions, including rheumatoid arthritis, atopic dermatitis and psoriasis.

Ischemia/reperfusion injury is an inflammatory condition that occurs on restoring blood flow to organs suffering from an obstructed supply causing ischemia (oxygen deprivation). Unless rapidly relieved by reperfusion, ischemia causes death of surrounding cells, and eventually, death of a whole organ or patient. However, accumulating evidence suggests that reperfusion may itself exert deleterious effects on surrounding tissue. The deleterious effects of reperfusion are believed to result at least in part from an inflammatory response mediated by activated neutrophils in the restored blood flow. Some patients have whole-body ischemia, whereas in other patients ischemia is confined to particular parts or organs of the body. For example, a patient may suffer from epidermal, myocardial, renal, cerebral, splenic, hepatic, spinal, splanchnic, pulmonary, partial-body, or whole-body ischemia. The therapeutic agents of the invention function by antagonizing the interaction of such lymphocytes with P-selectin.

One major component of acute allergic conditions, including asthma, is the degranulation of mast cells following challenge of subjects with antigens to which they are specifically sensitized. The consequences of mast cell degranulation include a bronchoconstrictor response and also an inflammatory response characterized in part by leukocyte accumulation. Histamine, which is contained together with other inflammatory mediators in mast cells, can induce the expression of P-selectin on vascular endothelial cells, indicating that degranulation of mast cells may also result in P-selectin expression and subsequent leukocyte accumulation. Because mast cell degranulation is a key element in the pathogenesis of allergic conditions, administration of antibodies to P-selectin will be useful for the treatment of human allergic conditions.

The methods are particularly useful for humans, but may also be practiced on veterinary subjects. The therapeutic methods are usually applied to organs present in living subjects. However, some methods, such as ischemia-reperfusion therapy, are equally applicable to dissected organs, particularly when such organs are awaiting transplant to a recipient patient. Therapeutic methods can also be performed ex vivo.

Therapeutic agents and compositions targeted against P-selectin can also be used in combination with agents targeted against other molecules, particularly humanized or human antibodies reactive with different adhesion molecules. Suitable immunoglobulins include those specific for CD11a, CD11b, CD18, E-selectin, L-selectin and ICAM-1. The immunoglobulins should bind to epitopes of these adhesion molecules so as to inhibit binding of leukocytes, particularly neutrophils, to endothelial cells. Other suitable antibodies for use in combination therapies are those specific for lymphokines, such as IL-1, IL-2 and IFN-γ, and their receptors. Such antibodies serve to block activation of endothelial cells, and thereby prevent their interaction with neutrophils in an inflammatory response.

The blocking P-selectin antibodies and pharmaceutical compositions of this invention are particularly useful for parenteral administration, i.e., subcutaneously, intramuscularly or intravenously. A number of new drug delivery approaches are being developed, the pharmaceutical compositions of the present invention are suitable for administration using these new methods, as well. See Langer, *Science*, 249:1527–1533 (1990).

The blocking P-selectin antibodies can be directly or indirectly coupled to the chemotherapeutic agent. The coupling, which may be performed by means, generally known in the art, should not substantially inhibit the ability of the immunoglobulin to bind the receptor nor should it substantially reduce the activity of the chemotherapeutic agent. A variety of chemotherapeutics can be coupled for targeting. For example, anti-inflammatory agents which may be coupled include immunomodulators, platelet activating factor (PAF) antagonists, cyclooxygenase inhibitors, lipoxygenase inhibitors, and leukotriene antagonists. Some preferred moieties include cyclosporin A, indomethacin, naproxen, FK-506, mycophenolic acid, and the like. Similarly, antioxidants, e.g., superoxide dismutase, are useful in treating reperfusion injury. Likewise, anticancer agents, such as daunomycin, doxorubicin, vinblastine, bleomycin, and the like can be targeted.

The P-selectin targeting may also be accomplished via amphipaths, or dual character molecules (polar:nonpolar) which exist as aggregates in aqueous solution. Amphipaths include nonpolar lipids, polar lipids, mono- and diglycerides, sulfatides, lysolecithin, phospholipids, saponin, bile acids and salts. These molecules can exist as emulsions and foams, micelles, insoluble monolayers, liquid crystals, phospholipid dispersions and lamellar layers. These are generically referred to herein as liposomes. In these preparations, the drug to be delivered is incorporated as part of a liposome in which an anti-P-selectin immunoglobulin is embedded. In this embodiment, the immunoglobulin need not bind a functional epitope on the P-selectin molecule, so long as the immunoglobulin effectively targets the liposome to P-selectin molecules. When the liposomes are brought into proximity of the affected cells, they deliver the selected therapeutic compositions.

A variety of methods are available for preparing liposomes, as described in, e.g., Szoka et al., *Ann. Rev. Biophys. Bioeng.* 9:467 (1980), U.S. Pat. Nos. 4,235,871, 4,501,728 and 4,837,028, incorporated herein by reference. Targeting of liposomes using a variety of targeting agents (e.g., ligands, receptors and monoclonal antibodies) is well known in the art. (see, e.g., U.S. Pat. Nos. 4,957,773 and 4,603,044, both of which are incorporated herein by reference). Standard methods for coupling targeting agents to liposomes can be used. Antibody targeted liposomes can be constructed using, for instance, liposomes which incorporate protein A (see Renneisen, et al., *J. Biol. Chem.*, 265:16337–16342 (1990) and Leonetti et al., *Proc. Natl. Acad. Sci. (USA)* 87:2448–2451 (1990).

Pharmaceutical compositions for parenteral administration usually comprise a solution of a therapeutic agent (e.g., an antibody against P-selectin (intact or binding fragment or a P-selectin fragment) or a cocktail of several such agents dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH-adjusting and buffering agents, tonicity adjusting agents and the like, for example sodium acetate, sodium chloride, potassium chloride, calcium chloride, sodium lactate, etc. The concentration of antibody in these formulations can vary widely, i.e., from less than about 0.5%, usually at or at least about 0.1% to as much as 1.5% or 2.0% by weight and will be selected primarily based on fluid volumes, viscosities, etc., in accordance with the particular mode of administration selected. Actual methods for preparing parenterally administrable compositions will be known or apparent to those skilled in the art and are described in more detail in, for example, Remington's Pharmaceutical Sciences, 17th Ed., Mack Publishing Company, Easton, Pa. (1985), which is incorporated herein by reference.

The antibodies of this invention can be lyophilized for storage and reconstituted in a suitable carrier prior to use. This technique has been shown to be effective with conventional immunoglobulins and art-known lyophilization and reconstitution techniques can be employed. Lyophilization and reconstitution can lead to varying degrees of antibody activity loss (e.g., with conventional immunoglobulins, IgM antibodies tend to have greater activity loss than IgG antibodies) and that use levels may have to be adjusted to compensate.

The compositions containing the present antibodies or a cocktail thereof can be administered for the prophylactic and/or therapeutic treatments. In therapeutic application, compositions are administered to a patient in an amount sufficient to cure or at least partially arrest the infection and its complications. An amount adequate to accomplish this is defined as a "therapeutically effective dose." Amounts effective for this use will depend upon the severity of the disease and the general state of the patient's own immune system, but generally range from about 0.05 mg/kg body weight to about 5 mg/kg body weight, preferably between about 0.2 mg/kg body weight to about 1.5 mg/kg body weight.

The materials of this invention may generally be employed in serious disease states, that is, life-threatening or potentially life-threatening situations. In such cases, in view of the minimization of extraneous substances and the lower probability of "foreign substance" rejections (e.g., HAMA) which are achieved by human or humanized antibody forms of this invention, it is possible and may be felt desirable by the treating physician to administer substantial excesses of these antibodies.

In prophylactic applications, compositions containing the present antibodies or a cocktail thereof are administered to a patient not already in a disease state to enhance the patient's resistance. Such an amount is defined to be a "prophylactically effective dose." In this use, the precise amounts again depend upon the patient's state of health and general level of immunity, but is generally in the ranges described above.

Single or multiple administrations of the compositions can be carried out with dose levels and pattern being selected by the treating physician. In any event, the pharmaceutical formulations should provide a quantity of the immunoglobulins of this invention sufficient to treat the patient effectively.

The antibodies of invention (whole and binding fragments) and fragments of P-selectin can also be used for diagnostic purposes. An amount sufficient for these purposes is defined to be a "diagnostically effective dose." In diagnostic uses, the precise amounts will depend upon the patient's state of health, mode of administration, and the like. The antibodies may either be labeled or unlabeled. Unlabeled antibodies can be used in combination with other labeled antibodies (second antibodies) that are reactive with the antibody, such as antibodies specific for the particular immunoglobulin constant region. Alternatively, the antibodies can be directly labeled. A wide variety of labels may be employed, such as radionuclides, fluorescers, enzymes, enzyme substrates, enzyme cofactors, enzyme inhibitors, ligands (particularly haptens).

The antibodies (whole and binding fragments) are useful for detecting the presence of cells bearing the P-selectin receptor. The presence of such cells is diagnostic of an inflammatory condition or disease and may signal the need for commencement of a therapeutic method discussed supra. Diagnosis can be accomplished by removing a cellular sample from a patient. The amount of expressed P-selectin receptor in individual cells of the sample is then determined, e.g., by immunohistochemical staining of fixed cells or by Western blotting of a cell extract with an antibody of the invention. Fragments of P-selectin are useful for monitoring the presence of activated neutrophils, a presence that can be indicate of an undesirable immune response.

Diagnosis can also be achieved by in vivo administration of a labelled antibody (preferably a humanized or human antibody) and detection by in vivo imaging. The concentration of MAb administered should be sufficient that the binding to cells having the target antigen is detectable compared to the background signal. The diagnostic reagent can be labelled with a radioisotope for camera imaging, or a paramagnetic isotope for magnetic resonance or electron spin resonance imaging.

A change (typically an increase) in the level of P-selectin protein in a cellular sample or imaged from an individual, which is outside the range of clinically established normal levels, may indicate the presence of an undesirable inflammatory response reaction in the individual from whom the sample was obtained, and/or indicate a predisposition of the individual for developing (or progressing through) such a reaction. P-selectin can also be employed as a differentiation marker to identify and type cells of certain lineages and developmental origins. Such cell-type specific detection can be used for histopathological diagnosis of undesired immune responses.

Kits can also be supplied for use with the subject antibodies. Thus, the subject antibody composition of the present invention may be provided, usually in a lyophilized form in a container, either alone or in conjunction with additional antibodies specific for the desired cell type. The antibodies, which may be conjugated to a label or toxin, or unconjugated, are included in the kits with buffers, such as Tris, phosphate, carbonate, etc., stabilizers, biocides, inert proteins, e.g., serum albumin, or the like, and a set of instructions for use. Generally, these materials will be present in less than about 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1 to 99% wt. of the total composition. Where a second antibody capable of binding to an anti-P-selectin antibody is employed in an assay, the second antibody will usually be present in a separate vial. The second antibody is typically conjugated to a label and formulated as described above.

The following examples are offered by way of illustration, not by limitation.

EXAMPLE 1

Preparation of Reagents

This example describes preparation or isolation of reagents used for the immunizations in Examples 2 and 3 and the ELISAs in Example 4.

A. "Outdated Platelets"

A preparation of platelets which was purified from "outdated platelets" obtained from the San Diego Blood Bank. The method used was a modification of the method described in Moore et al., *J. Cell. Biol.* 112:491–499 (1991), which is incorporated herein by reference. Briefly, 25 units of outdated platelet-rich plasma were centrifuged twice for 10 min at 1200 rpm (300xg) to remove contaminating non-platelet blood cells. The purified platelet preparation was then washed three times with a buffer containing 0.1M NaCl, 20 mM Tris and 5 mM Benzamidine. It also contained 3.8% sodium citrate. The pH was adjusted to 7.5 with 1N HCl. The purified platelets were stored at 70° C. and were washed once in PBS before injection.

B. Purified P-Selectin

Fractionation of Platelets: Washed outdated platelets were fractionated essentially according to Moore et al., 1991, supra, 25 units washed platelets were made 100 uM in leupeptin and 1 mM in 4-(2aminoethyl)-benzenesulfonylfluoride (AEBSF), freeze-thawed three times in dry ice/methanol, and homogenized ten strokes with a DOUNCE homogenizer. The suspension was then centrifuged in a BECKMAN Ti 70 rotor at 4° C. at 35,000 rpm for 60 min. The supernatant from this spin was the starting material for the purification of "soluble" P-selectin. The pellet was resuspended in 30 ml 1 mM $MnCl_2$, 1 mM $CaCl_2$, 5 mM benzamidine-HCl, 0,1M NaCl, 20 mM Tris, 2% Triton X-100, pH 7.5, homogenized 10 strokes with a Dounce homogenizer, and incubated for 1 h at 4° C.. The suspension was then centrifuged for 1 h in a BECKMAN Ti 70 rotor at 4° C. at 35,000 rpm. The supernatant from this spin was the starting material for the isolation of "membrane-bound" P-selectin.

Isolation of P-Selectin from Fractionated Platelets: "Soluble" and "membrane-bound" P-selectin were then further purified separately by some or all of the following procedures. The non-ionic detergent RENNEX 30 (ACCURATE CHEMICAL AND SCIENTIFIC CORP.) was included at a concentration of 0.1% in all buffers for isolation of the membrane-bound form of P-selectin. All buffers also included 1 mM $CaCl_2$ and 1 mM $MnCl_2$. Fractions containing P-selectin were detected by Western blotting with the monoclonal antibody PNB1.6.

Lentil Lectin Chromatography: "Soluble P-selectin" supernatant or "membrane-bound P-selectin" detergent extract from 25 units of platelets were passed over a column (1.5×5.5 cm) of lectin from Lens culinaris (lentil lectin) coupled to SEPHAROSE 4B (SIGMA CHEMICAL CO., L-0511). The column was then washed with 150 ml 20 mM Tris, 0.1M NaCl, pH 7.5. Bound glycoproteins were then eluted from the column with 10×3 ml aliquots of 20 mM Tris, 0.5M NaCl, 0.5M alpha-methyl D-mannopyranoside, pH 7.5. Fractions containing P-selectin were concentrated to 1.5–2 ml in an AMICON CENTRIPREP 30.

Gel Filtration Chromatography: Concentrated fractions from lentil lectin chromatography were injected onto a TOSO HAAS G3000 SW HPLC column (21.5 mm×30 cm) equilibrated with 20 mM Tris, 0.1M NaCl, pH 7.5. The column was eluted with the same buffer at a flow rate of 0.75 ml/min, fractions (1.5 ml) were collected, and analyzed by Western blotting. Fractions containing P-selectin were pooled and concentrated to 1.5–2 ml in an Amicon Centriprep 30, followed by several buffer exchanges with 20 mM Tris, pH 7.5.

Heparin-Agarose Chromatography: The sample, in 20 mM Tris, pH 7.5, was applied to a 1 ml column of Heparin-Agarose, the column was washed with the same buffer, and eluted with 20 mM Tris, 1.5M NaCl, pH 7.5.

Anion Exchange Chromatography: Fractions were dialyzed into 20 mM Tris, pH 7.5, and injected onto a TOSO HAAS DEAE-5PW column (7.5 mm×7.5 cm) that had been equilibrated with 20 mM Tris, pH 7.5, and eluted with a salt gradient to 1M NaCl. Fractions containing P-selectin were pooled, and concentrated in an AMICON CENTRIPREP-30, and stored at −80° C.

Cation Exchange Chromatography: Samples were dialyzed into 10 mM phosphate, pH 7, and injected onto a POROS CM/P (4.6/100) column that had been equilibrated in the same buffer, and eluted with a salt gradient to 1M NaCl.

C. Isolation and Activation of Fresh Human Platelets

All chemicals used throughout the platelet isolation procedure were obtained from SIGMA CHEMICAL COMPANY, St. Louis, Mo.

1. 42 ml of blood was drawn from a human volunteer blood donor into a syringe containing 7 ml Acid Citrate Dextrose anticoagulant (ACD).

Preparation of ACD anticoagulant

| Dextrose | 2.0 g |
| Sodium Citrate | 2.49 g |
| Citric Acid | 1.25 g |

Bring to 100 ml with distilled water

2. The needle was removed and the blood was transferred to two sterile 50 ml tubes.

3. The tubes were centrifuged in an IECC-6000 centrifuge equipped with a 921 head (radius=17.2 cm.) at 800 rpm (approx. 90xg) for 15 min at room temperature with the brake off.

4. The supernatant was removed using a plastic pipette. The supernatant was removed as close as possible to the buffy layer.

5. The supernatant was centrifuged at 1200 rpm (approx. 300xg) for 6 min.

6. The supernatant was removed.

7. The supernatant was centrifuged at 2000 rpm (approx. 1200xg) for 10 min. The platelets appeared as a cell button at the bottom of the tube. The supernatant was discarded.

8. The platelets were washed as follows: 2 ml Tyrode-Hepes Buffer pH 6.5, containing Prostaglandin, $E_1$(PGE$_1$ at a final concentration of 100 nM was added and the platelets were gently resuspended. A further 10 ml of the same buffer was added and the sample was centrifuged at 3000 rpm for 10 min.

Preparation of Tyrode-Hepes Buffer

| NaCl | 8.0 g |
| KCl | 0.2 g |
| $NaH_2PO_4H_2O$ | 0.057 g |
| $MgCl_2 6H_2O$ | 0.184 g |
| $NaHCO_3$ | 0.1 g |
| Dextrose | 1.0 g |
| HEPES | 2.383 g |

Bring to 1 liter with distilled water. Adjust pH to 6.5 with 1N NaOH.

9. Step #8 was repeated once more and then the platelets were washed once in the same buffer without $PGE_1$.

10. The platelets were counted in a COULTER COUNTER and diluted to $2 \times 10^8$/ml.

11. The pH of the platelet suspension was adjusted to 7.2, and the amount of thrombin (Human thrombin-Sigma) required for maximal activation was determined. There is a certain amount of donor variation, but optimal activation is normally obtained in the range of 0.25–0.5 Units/ml. Maximal activation i.e., maximal thrombin-induced aggregation appears to correspond to maximal expression of P-selectin.

12. The required amount of thrombin was added to the platelet preparation and the mixture was allowed to stand at room temperature for 20 min without stirring to prevent aggregation.

EXAMPLE 2

Preparation of Blocking P-selectin Antibody

This example describes preparation of mu mAB PB1.3, a monoclonal antibody to P-selectin that inhibits binding of thrombin-activated platelets to neutrophils.

One RBF/DnJ male mouse, received from Jackson Laboratories, was used as a source of antibody producing cells and was immunized according to the following schedule (all injections were performed intraperitoneally):

1. Month 1—200 µl of packed "outdated platelets" containing approximately $6 \times 10^9$ platelets 2. Month 2—250 µl of packed "outdated platelets" ($8 \times 10^9$ platelets)

3. Month 4—250 µl of packed "outdated platelets" ($8 \times 10^9$ platelets)

4. Month 5—"Soluble" fraction of P-selectin, isolated on lentil lectin.

5. Month 6—"Soluble" P-selectin, purified by lentil lectin, gel filtration, heparin-agarose, and ion-exchange chromatography.

Details of the preparation of all agents used for immunization are presented in Example 1.

A. Myeloma Fusion Cell Line

FOX-NY, a mouse myeloma cell line deficient for adenosine phosphoribosyltransferase (APRT) and hypoxanthine phosphoribosyltransferase (HPRT) was obtained from the AMERICAN TYPE CULTURE COLLECTION (CRL 1732) and maintained in RPMI 1640 containing 10% fetal bovine serum (HYCLONE) and 1% L-glutamine.

B. Cell Fusion Procedure

Four days after the final boost the spleen was removed and $1.2 \times 10^8$ splenocytes were recovered. These were fused with FOX-NY myeloma cells using PEG 1500 (BMB) using the following protocol: The isolated splenocytes were washed twice in serum-free cell culture medium. Splenocytes and myeloma cells were combined at a ratio of 1:4.8 (myelomas to spleen cells). The combined cell pellet was washed twice in serum free medium, then aspirated to dryness. The cell pellet was resuspended by gentle tapping and heated in a waterbath at 37° C. for 1 min. The pellet was distributed around the sides and bottom of a 50 ml conical centrifuge tube. One ml of PEG 1500 (50% w/v in 75 mM HEPES, BMB Lot #14702800) previously warmed to 37° C. was added over 60 seconds while rotating the tube to maintain a thin layer of cells. One ml of serum free medium was added slowly over 60 seconds. An additional 1 ml of medium was added slightly faster. A further 8 ml of medium was added and the tube was allowed to stand undisturbed for 8 min and was then centrifuged for 5 min at 300xg. The final pellet was resuspended in RPMI 1640 containing 10% fetal bovine serum HYCLONE), 1% L-glutamine, 1% Sodium Pyruvate, and 1xAAT (SIGMA). The cells were plated in 10 flat bottom 96 well microtiter plates (COSTAR). No feeder cells were used.

EXAMPLE 3

Preparation of Non-blocking Anti-P-selectin Antibody

This example describes preparation of mAB PNB1.6 a monoclonal antibody to P-selectin that does not inhibit binding of thrombin-activated platelets to neutrophils.

One RBF/DnJ male mouse, received from JACKSON LABORATORIES, was used as a source of antibody producing cells and was immunized according to the following schedule (all injections were performed intraperitoneally):

1. Month 1—100 μl of thrombin-activated freshly isolated platelets (approximately $3 \times 10^9$ platelets)

2. Month 2—200 μl of thrombin-activated fresh platelets ($6 \times 10^9$ platelets)

3. Month 4—100 μl of thrombin-activated fresh platelets ($3 \times 10^9$ platelets)

Four days post final boost, the spleen was removed and the splenocytes were recovered. They were fused with FOX-NY myeloma cells using PEG 1500 (Sigma) generally as described in Oi et al., "Immunoglobulin-Producing Hybrid Cell Lines" in *Selected Methods in Cellular Immunology*, eds. Mishell and Shiigi, pp 351–372, 1980, which is incorporated herein by reference.

EXAMPLE 4

Screening for Antibody

This example describes screening of supernatant media from fused cells produced in Examples 2 and 3. Supernatants from Example 2 were tested by ELISA assay against (a) thrombin-activated platelets, (b) purified P-selectin and (c) recombinant P-selectin. Supernatants from Example 2 were tested by ELISA assay against thrombin-activated platelets. Each of these assays is described below. Preparation of the reagents used in each of the assays is described in Example 1.

A. Thrombin-Activated Platelets

1. A 96 well flat bottom COSTAR plate was coated with 0.1% gelatin (2% gelatin-Sigma) by adding 100 μl/well and incubating at 37° C. for 15 min.

2. The gelatin was removed and 100 μl of thrombin activated platelets ($10^8$/ml) were added to each well.

3. The plate was incubated at 37° C. for 15 min.

4. The plate was centrifuged at 800 rpm (90xg) for 2 min.

5. The unbound platelets were removed and the plate was washed x2 with PBS.

6. 100 μl of PBS containing 1% BSA were added to each well and the plate was allowed to stand at room temperature for 60 min.

7. 100 μl of supernatant were added to each well. The plate was placed on a shaker at room temperature for 60 min.

8. The plate was washed x4 with PBS.

9. 100 μl of peroxidase-conjugated goat anti-mouse IgG diluted 1/1000 in PBS containing 1% BSA was added to each well. The plate was allowed to stand at room temperature for 30 min.

10. The plate was washed x7 with PBS.

11. 100 μl of ABTS substrate system (KIRKEGAARD AND PERRY, LABORATORIES, INC.) was added to each well.

12. The plate was allowed to develop at room temperature for up to 30 min.

13. The OD was measured at 414 nm in a TILTERTECK MULTISKAN MCC/340.

B. Purified P-selectin

1. "Soluble" or "membrane-bound" P-selectin, isolated by chromatography on lentil lectin, gel filtration, and DEAE columns, was diluted (1:50 to 1:1000) in DPBS (Dulbecco's Phosphate Buffered Saline is Phosphate-buffered saline (PBS) containing $CaCl_2$ (1 mM) and $MgSO_4$ (0.5 mM)) and coated overnight at 4° C. onto Falcon 96 well microtiter plates.

2. The plates were then blocked for 1 h or longer with DPBS+1% BSA.

3. Supernatants to be assayed were then added to the wells, and incubated for 30–60 min at room temp.

4. The plates were washed with DPBS, and then sheep anti-mouse IgG horseradish peroxidase conjugate (SIGMA A-6782, 1:1000 in DPBS+1% BSA) was added to the wells, and the plates were incubated at room temp. for 1 hr.

5. The plates were then washed with DPBS, and developed with the TMB MICROWELL SUBSTRATE SYSTEM (KIRKEGAARD AND PERRY LABORATORIES, INC.)

C. Recombinant P-selectin

1. Ninety six well flat bottom plates were coated overnight at 4° C. with 100 μl of P-selectin which had been shed into the serum free medium of a pool of 293 cell clones transfected with the recombinant P-selectin gene. This supernatant contained at least 8 ng/ml of P-selectin and was coated onto COSTAR plates either undiluted or diluted 1:8 with media.

2. The plate was washed once with Dulbecco's PBS (DPBS) and blocked with 200 μl DPBS containing 1% BSA for 30 min at room temperature.

3. The plate was then processed for the ELISA Assay according to steps 7–13 in Section A, Page 9.

D. Isotyping Analysis of mABs to P-Selectin

Isotype analysis of mu MAbs PB1.3 and PNB1.6 indicated that both monoclonal antibodies were of the mouse immunoglobulin subclass, IgG1. Isotyping was performed using the capture method of BOEHRINGER MANNHEIM Mouse-Hybridoma-Subtyping Kit.

EXAMPLE 5

Detection of P-selectin

This example describes the detection of P-selectin by western blotting. Samples containing P-selectin were mixed with an equal volume of SDS-PAGE sample buffer (non-reducing), heated at 100° C., run on a NOVEX 8–16% gradient gel, and transferred electrophoretically to nitrocellulose. The nitrocellulose membrane was then blocked for at least 1 h in phosphate-buffered saline (PBS) +1% bovine serum albumin (BSA). The membrane was then incubated at room temperature for 1 h or longer with either tissue culture supernatant from hybridomas expressing the appropriate monoclonal antibody or purified antibody (5 µg/ml) in PBS+1% BSA. The membrane was then washed several times in PBS+1% BSA, and incubated for 1 h with a 1 to 1000 dilution of sheep anti-mouse IgG horseradish peroxidase conjugate (SIGMA A-6782) in PBS+1% BSA. The membrane was then washed, and bands visualized with tetramethylbenzidine/membrane enhancer (KIRKEGAARD AND PERRY LABORATORIES, INC.)

For tissue culture supernatants from both mu MAbs PB1.3 and PNB1.6 a protein was detected having a molecular weight of 140Kd. This was shown in preparations of solubilized platelet membranes as well as in purified P-selectin.

EXAMPLE 6

In Vivo Inhibition of Acute Inflammatory Injury by Blocking P-selectin Antibody This example provides data demonstrating the ability of blocking P-selectin antibody of the invention to treat acute lung injury. In this example, systemic complement activation was produced by vascular infusion of the cobra venom factor (CVF) into rats. Injury in this model develops rapidly and is known to be dependent on toxic oxygen products generated from neutrophils.

For these studies, the two monoclonal antibodies described in Examples 2 and 3 were used. Of particular importance for this study, the blocking P-selectin antibody mu MAb PB1.3 also inhibited adhesion of thrombin-activated rat platelets to human neutrophils (FIG. 1). These data suggest that mu MAb PB1.3 recognizes a conserved functional P-selectin epitope and that a blocking P-selectin antibody might be useful in the treatment of other inflammatory injuries.

For the in vivo experiments 20 units CVF/kg body weight were infused intravenously into 300 gm adult male Long-Evans rats. This results in rapid intrapulmonary, intravascular sequestration of blood neutrophils, with resulting damage of interstitial capillary endothelial cells at points of physical contact of endothelial cells and neutrophils. When employed, mu MAbs PB1.3 and PNB1.6 were infused intravenously in the amounts indicated together with CVF, in total volume of 0.5 ml. Negative control animals received 0.5 ml intravenous infusion of phosphate buffered saline (PBS). In all cases the infusion material also contained trace amounts of ($^{125}$I)-bovine serum albumin and homologous ($^{51}$Cr)-red blood cells (RBC). The parameters of lung injury (leakage of albumin and extravasation of RBC) were determined at 30 min. according to established techniques Mulligan, et al., *J. Clin Invest.* 88:1396 (1991).

Figure 2A:
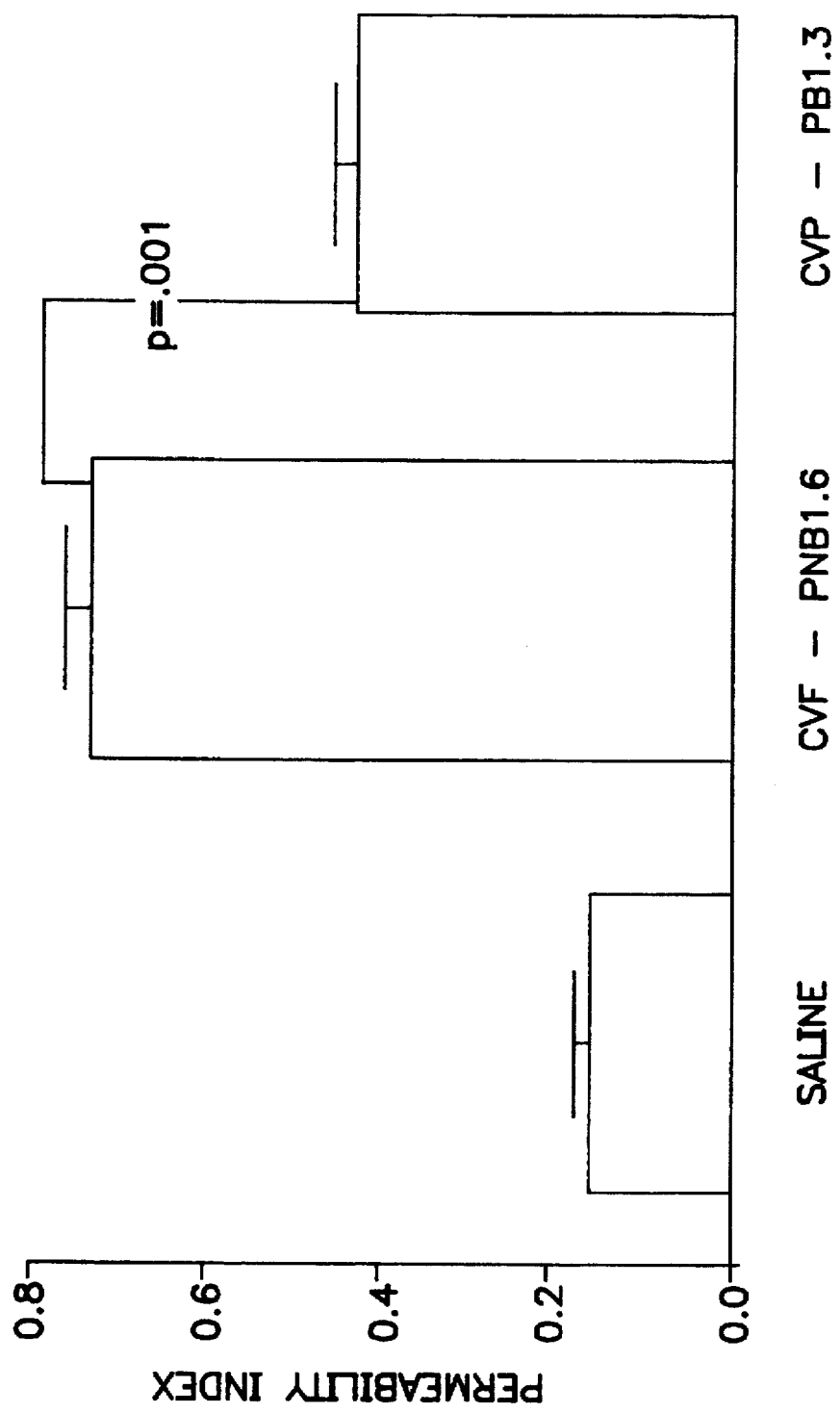
FIGS. 2A and 2B show that anti-inflammatory immunoglobulins of the invention effectively prevent lung injury induced by infusion of cobra venom factor (CVF) as measured by permeability (FIG. 2A) and hemorrhage (FIG. 2B).
Figure 2B:
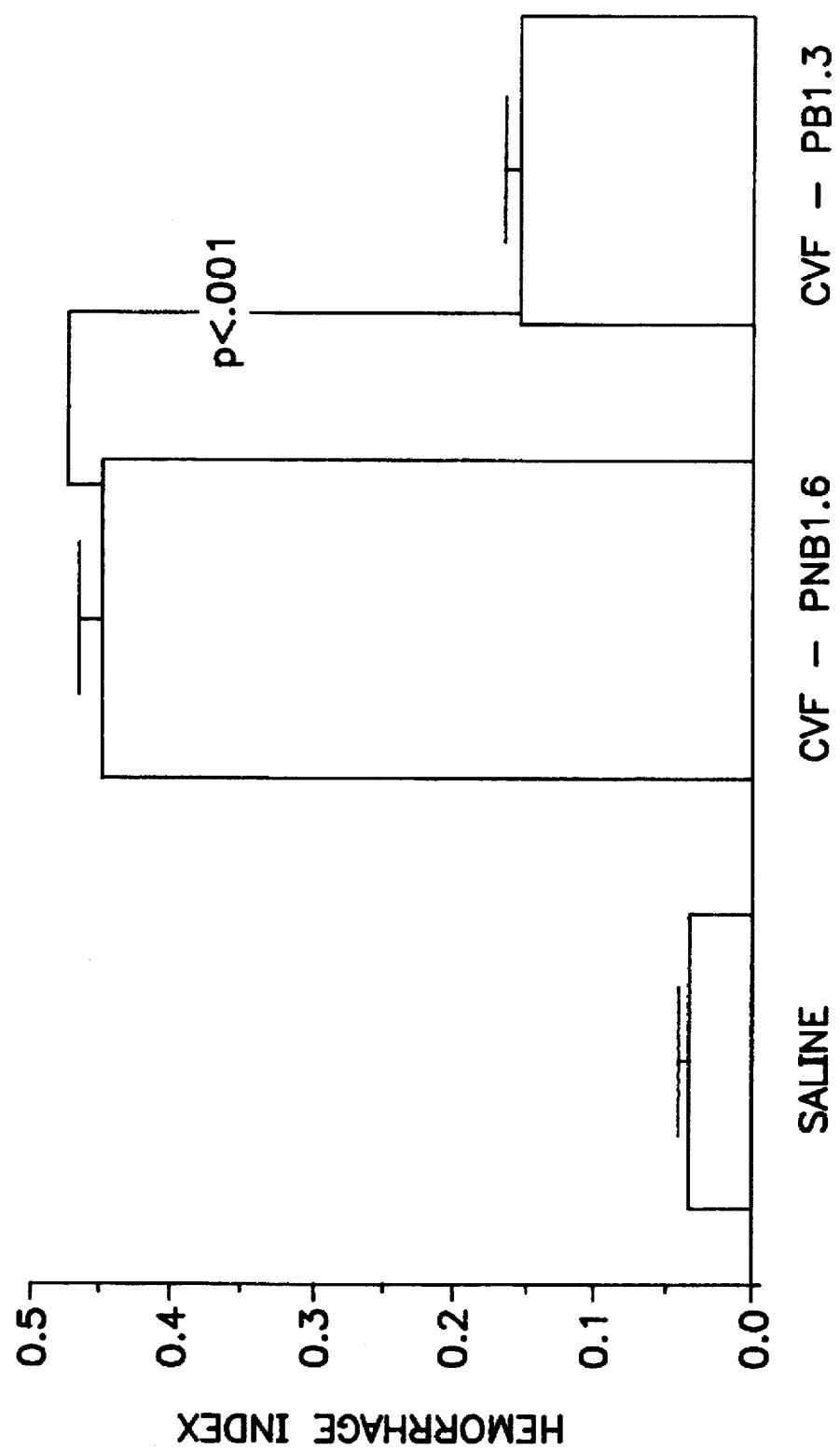

The results of these experiments are shown in FIGS. 2A and 2B. Coinfusion of 200 µg PNB1.6 (the non-blocking anti-P-selectin antibody) together with CVF failed to cause any reduction in lung injury when compared to the values of untreated CVF positive controls. Thus animals receiving CVF PNB1.6 in PBS served as the reference positive control values. When 100 µg mu MAb PB1.3 antibody was infused with the CVF permeability was reduced by 19.2% (p=0.002) and hemorrhage was reduced by 37.5% (p=0.001) (data now shown). When 200 µg mu MAb PB1.3 was added, permeability was reduced by 50.8% (p<0.001) (FIG. 2A) and hemorrhage by 70.0% (p<0.001) and 70.1% (p<0.001), respectively (FIG. 2B).

Figure 3A:
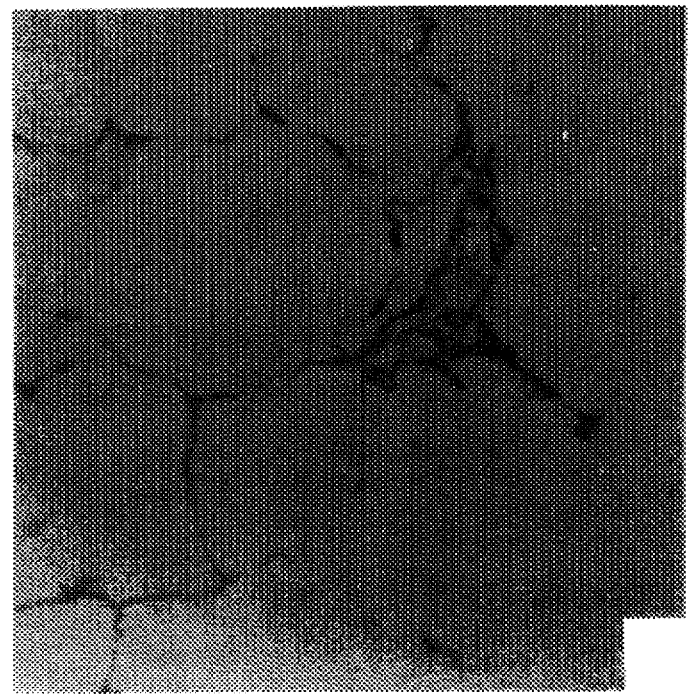
FIGS. 3A, 3B, 3C, 3D, 3E, 3F, 3G, and 3H show that P-selectin expression content in lungs of animals is upregulated in response to cobra venom infusion visualized by horseradish proxidase stain of mu MAb PB1.3.
Figure 3B:
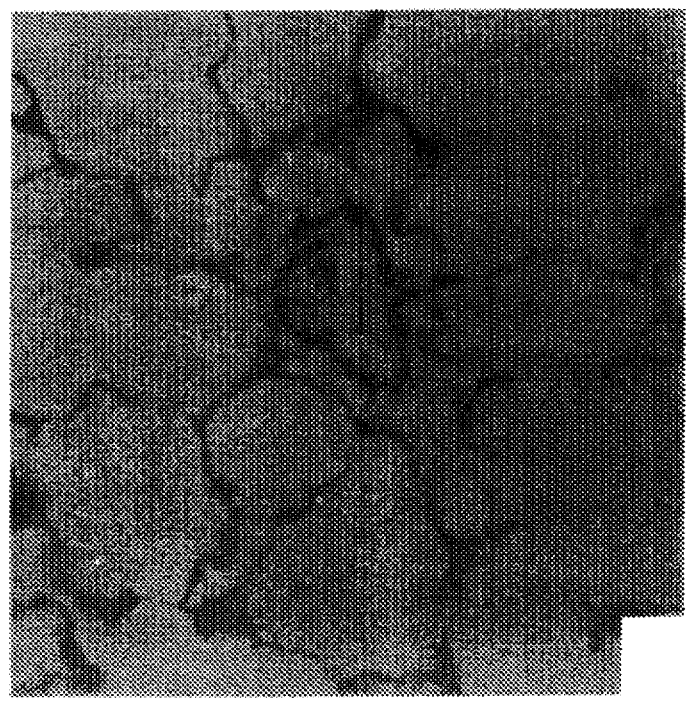
Figure 3C:
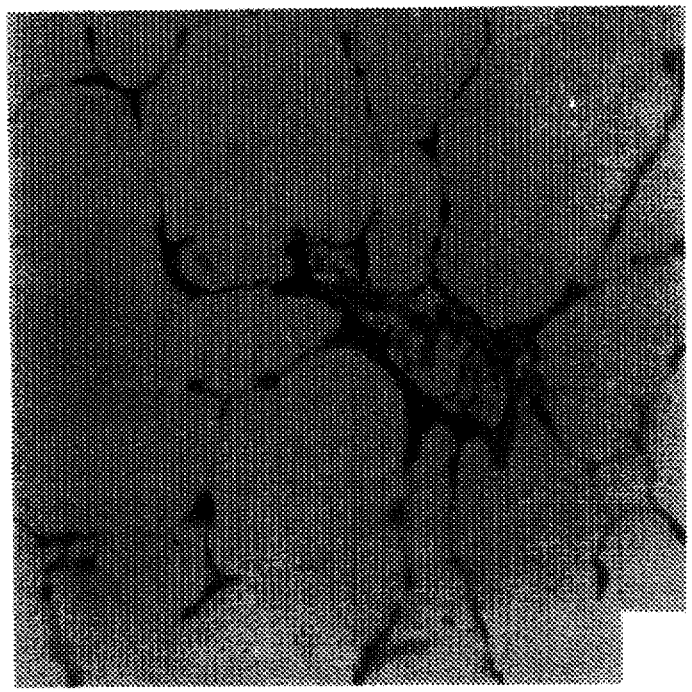
Figure 3D:
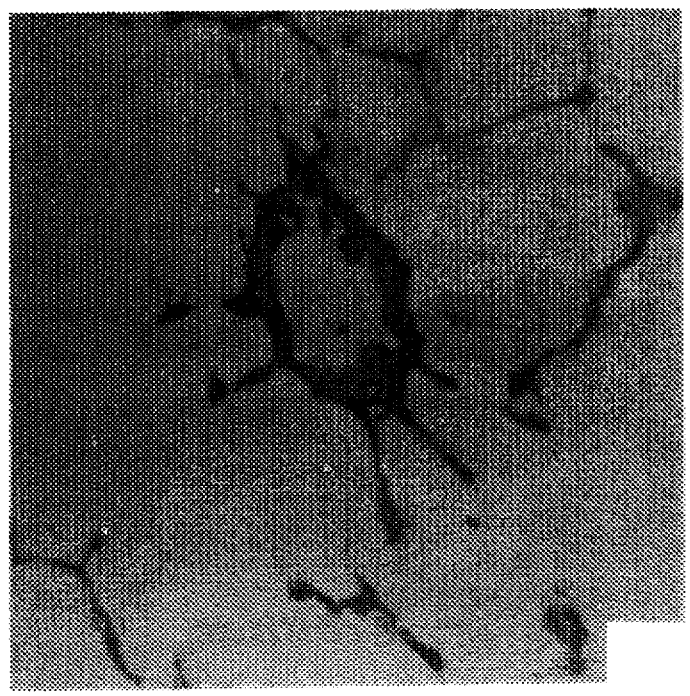
Figure 3E:
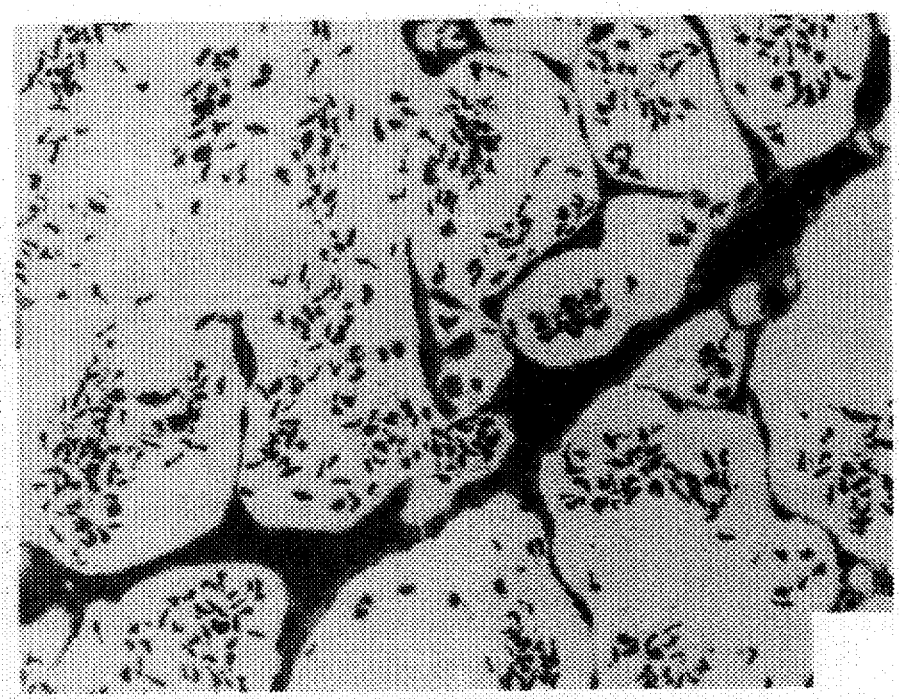
Figure 3F:
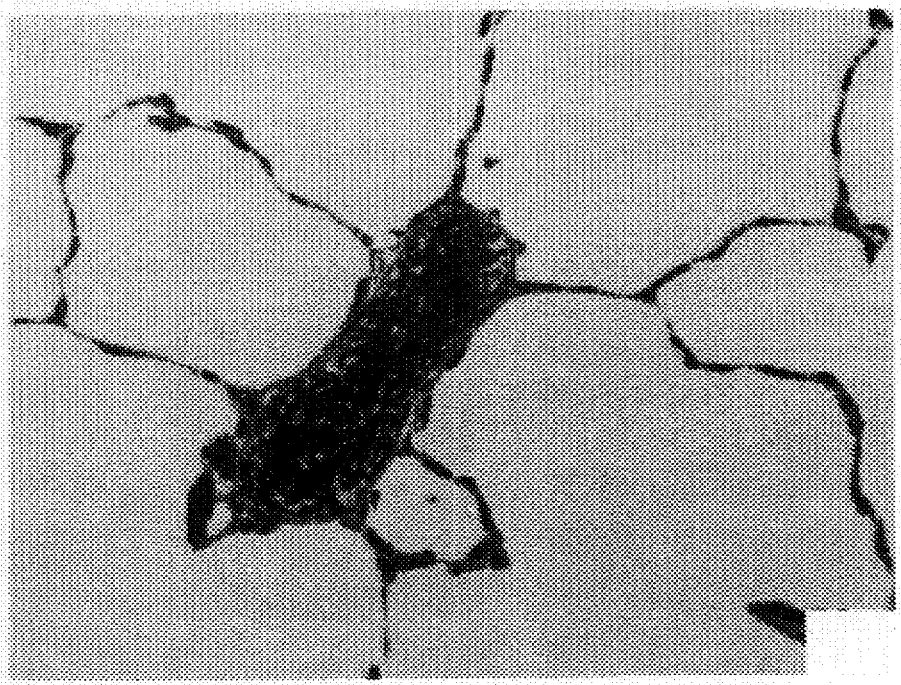
Figure 3G:
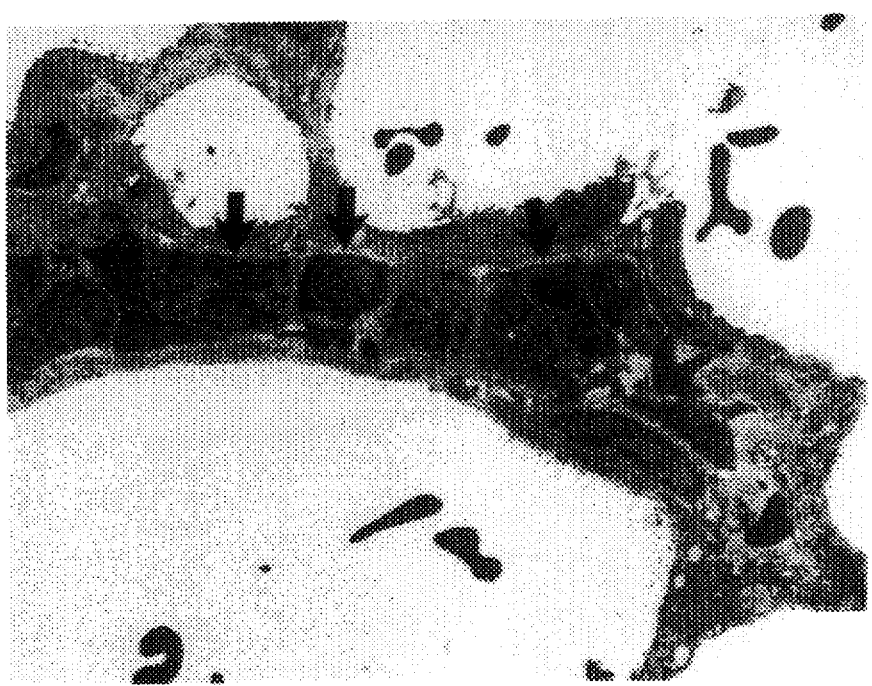
Figure 3H:
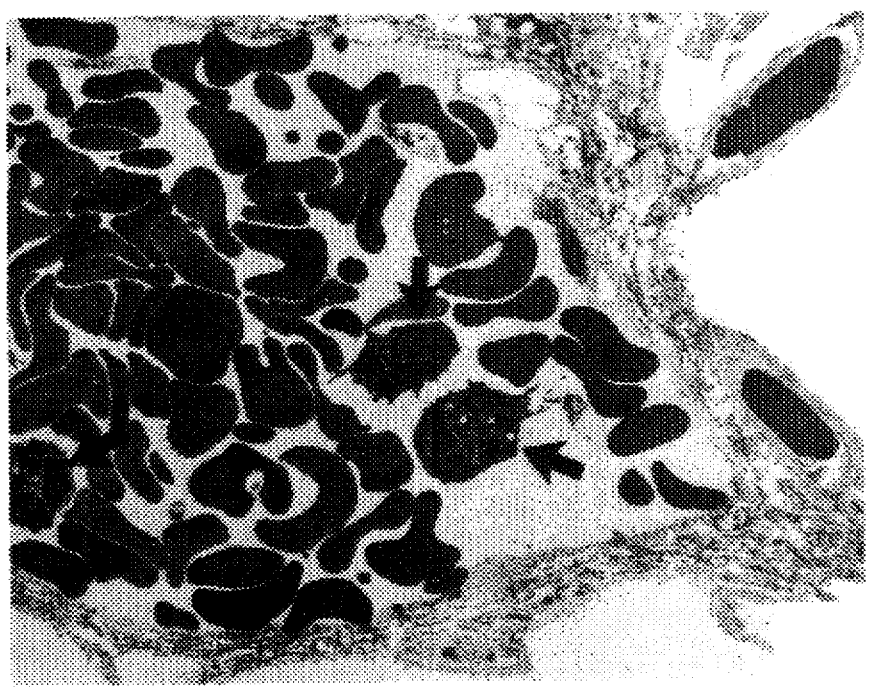

Lungs from companion sets of animals were homogenized sonicated and the myeloperoxidase activity (MPO) measured in order to obtain an estimate of the neutrophil content in lung. MPO was determined by the decomposition of $H_2O_2$ in the presence of o-dianisidine according to standard procedures, Warren et al. *J. Clin. Invest.* 84:1873 (1989). As shown in FIGS. 3A, 3B, 3C and 3D, treatment with 100, 200 or 400 µg mu MAb PB1.3 reduced MPO content below the values in the reference (untreated) positive control group by 26% (p=0.024), 41% (p<0.001) and 50% (p<0.001), respectively. In animals injected with 200 µg of PNB1.6 there was no reduction in MPO content, consistent with the inability of this antibody to protect against CVF-induced lung injury. Thus, the protective effects of the blocking antibody mu MAb PB1.3, correlate with its ability to interfere with neutrophil accumulation in lung tissue. Transmission electron microscopic examination of lung sections confirmed that treatment with mu MAb PB1.3 resulted in reduced accumulation of neutrophils within the pulmonary interstitial capillaries, diminished adherence of neutrophils to endothelial cells, and reduced evidence of damaged endothelial cells (FIGS. 3F and 3H).

In order to investigate lung expression of P-selectin following intravenous injection of CVF, an additional group of rats was infused with CVF and animals sacrificed at times 0, 5, 10, 15, 20 and 60 min later. Lungs were inflated with O.C.T., snap frozen, and sections obtained and examined for presence of P-selectin by immunohistochemical techniques, using mu MAb PB1.3. Little detectable reactivity in the pulmonary vasculature was found at time 0, whereas staining was clearly evident at 5 min and was increased at 15 and 20 min after infusion of CVF. The pattern of staining involved pulmonary venules and septal areas in a pattern consistent with staining of interstitial capillaries. At 60 min. staining had largely disappeared (data not shown). Although P-selectin is presumably present in intracellular storage granules prior to CVF infusion, it is apparent that mobilization of P-selectin to the surface of the endothelium dramatically enhanced its reactivity with mu MAb PB1.3 antibody.

EXAMPLE 7

Competitive Binding Assay

Methods of isolation of platelets from human blood, activation of isolated platelets with thrombin and isolation of PMNs (neutrophils) are described in Example 1 above. INCUBATION OF THROMBIN ACTIVATED PLATELETS WITH MONOCLONAL ANTIBODIES TO P-SELECTIN.

a. Place 20 µl thrombin-activated platelets (2×10$^8$/ml) into each of 24 EPPENDORF tubes (1.5 ml) in duplicate.

b. To 8 of these tubes, add 20 µl of the IgG fraction purified from PNB1.6 at a concentration of 10 µg/ml in Tyrode-Hepes Buffer, pH 7.2 containing 1 mM CaCl$_2$. To a second row of 8 tubes, add 20 µl of the same IgG preparation at a concentration of 1 µg/ml. To the third row of 8 tubes add 20 µl of the buffer alone.

c. Mix and stand at room temperature for 20 min.

d. To each row of 8 tubes add 20 µl of the IgG fraction purified from mu MAb PB1.3 at concentrations ranging from 10 µg/ml to 0.03 µg/ml.

e. Mix and stand at room temperature for 20 min.

f. Add 20 µl neutrophils at 3×10$^6$/ml.

g. Mix and stand at room temperature for 20 min.

h. Evaluate adhesion microscopically as follows: Count 100 neutrophils in each sample. Score a cell as positive if it has bound 2 or more platelets, and as negative if it has bound less than 2. Calculate the percentage of positive cells.

As shown in FIG. 1, pretreatment of thrombin activated platelets with mu MAb PNB1.6 did not affect the ability of mu MAb PB1.3 to block their P-Selectin mediated adhesion to neutrophils.

EXAMPLE 8

Characterization of Binding of Blocking P-selectin Antibodies

I(a) Purification of Monoclonal Antibodies: The monoclonal antibodies PNB1-6 and 84/26 were isolated from tissue culture supernatants by passage over a column of protein G Sepharose 4 Fast Flow (PHARMACIA). The column was washed extensively with phosphate-buffered saline (PBS), and bound antibody was eluted with 0.1M glycine-HCl pH 2.7 into tubes containing 0.2 to 0.5 volume 1M Tris, pH 8.8. The procedure used for isolating mu MAb PB1.3 was identical except that the antibody bound to protein G was eluted with 0.1M acetate-HCl pH 2.5 into tubes containing 0.3 volumes 2M Tris, pH 10. Antibody containing fractions were pooled, and dialyzed against several changes of PBS at 4° C.

(b) Preparation of mu MAb PB1.3 Affinity Column: For use in the purification of P-selectin, mu MAb PB1.3 was coupled to tresyl activated agarose according to the manufacturer's affinity instructions (SCHLEICHER AND SCHUELL).

(c) Purification of P-Selectin: to washed, outdated human platelets, prepared as described above, was added 1/100th volume 5 mg/ml leupeptin, and 1/100th volume 35 mg/ml AEBSF (CALBIOCHEM). After mixing, the platelets were freeze-thawed three times in either a dry-ice/methanol bath or liquid nitrogen, homogenized ten strokes with a DOUNCE homogenizer, and centrifuged for 1 h at 35,000 rpm at 4° C. in a BECKMAN 70TI rotor. The pellet was resuspended in Dulbecco's phosphate-buffered saline (DPBS, WHITTAKER BIOPRODUCTS, which contains approximately 0.9 uM $CA^{++}$ and 0.5 mM $Mg^{++}$), and made 5 mM in benzamidine-HCl, 100 uM in leupeptin, and 2% in Triton X-100. The suspension was resuspended, and homogenized 10 strokes with a DOUNCE homogenizer. After a 1 h incubation at 4° C., the solution was again centrifuged in a BECKMAN 70TI rotor for 1 h at 4° C. at 35,000 rpm. The supernatant was passed over a column of mu MAb PB1.3-agarose that had been equilibrated with DPBS+0.05% RENNEX 30 (ACCURATE CHEMICAL AND SCIENTIFIC CORP.). The column was washed extensively with DPBS+ 0.05% RENNEX 30, and bound P-selectin was eluted with 0.1M triethylamine-HCL, 0.05% RENNEX 30, pH 11.5, into tubes containing 0.1 volume 1M phosphate, pH 6.8. Fractions containing P-selectin were pooled, dialyzed against DPBS+0.05% RENNEX 30, concentrated using either a CENTRICON 30 or CENTRIPREP 30 spin concentrator (AMICON), aliquoted, and stored at -80° C.

(d) Preparation of the Peptide CQNRYTDLVAIQNKNE (SEQ ID No: 1) (Cys-Gln-Asn-Arg-Tyr-Thr-Asp-Leu-Val-Ala-Ile-Gln-Asn-Lys-Asn-Glu-$NH_2$): The peptide was synthesized on an APPLIED BIOSYSTEMS (Foster City, Calif.) 430A peptide synthesizer using Fmoc protected amino acids and 2-(1H-Benzotriazol-1-yl)-1,1,3,3-tetramethyluronium hexafluorophosphate (HBATU) esters for amino acid activation. Each amino acid was routinely double coupled. Fmoc protected amino acids and Hydroxybenzotriazole were purchased from APPLIED BIOSYSTEMS. All solvents were purchased from BURDICK AND JACKSON. HBTU was purchased from RICHELIEU BIO-TECHNOLOGIES (St. Hyacinthe, Canada). Piperidine and trifluoroacetic acid, acetic anhydride, thioanisole, phenol and ethanedithiol were purchased from SIGMA CHEMICAL CORPORATION.

Fmoc-Amide resin (BACHEM BIOSCIENCES) was loaded into the peptide synthesis reaction vessel and washed one time with N-methylpyrrolidone (NMP). The following operations were then sequentially performed:

1. The Fmoc protecting group was removed by treatment of the resin bound amino acid with 25% piperidine in NMP.
2. The resin was washed 5 times with NMP.
3. A mixture containing N-α-Fmoc-L-Glutamic acid γ-t-butylester, diisopropylethylamine, HBTU and NMP was added to the reaction vessel and allowed to react for 30 min, under vortex agitation.
4. The solvent was drained, and the resin was washed three times with NMP.
5. Steps (3) and (4) were repeated two more times.
6. The resin was washed four more times with NMP.

Steps 1-6 were repeated for each amino acid of the peptide. Following the final coupling cycle, the resin-bound peptide was deprotected by reaction with 25% piperidine in NMP, washed 7 times with NMP, and washed 2 times with dichloromethane. The resin was dried in vacuo for 24 h. The peptide was cleaved from the resin by treatment with trifluoroacetic acid containing 2.5% ethanedithiol, 5% thioanisole, 7.5% phenol, and 5% water. The polystyrene resin was separated from the trifluoroacetic acid solution by filtration. Trifluoroacetic acid was removed by evaporation in vacuo. The crude peptide was triturated with diethylether and dissolved in water. The water was removed by lyophilization. The peptide was then purified by reverse phase HPLC on a $C_8$ column (VYDAC) using a gradient of acetonitrile, water, each containing 0.1% TFA as modifier.

(e) Biotinylation of Monoclonal Antibodies: Antibodies were dialyzed against 0.1M sodium bicarbonate, pH 8.5. NHS-LC Biotin (PIERCE) was added to 0.3 mg/ml. After 2 hrs at room temperature, antibodies were dialyzed against several changes of PBS.

(f) Coating of Microtiter Plates for ELISA: 96 well microtiter plates (FALCON MICROTEST III) were coated overnight at 4° C. with 50 µl/well of 2 µg/ml affinity purified P-selectin in DPBS.

(g) Western Blotting: mu MAbs PB1.3, PNB1.6, and 84-26 all bind to a single band of 140 KD when platelets are dissolved in SDS-PAGE running buffer (unreduced), subjected to SDS-PAGE, and transferred to nitrocellulose (data not shown). We have also found that mu MAbs PB1.3 and PNB1.6 no longer recognize P-selectin on western blots when the samples have been reduced with β-mercaptoethanol.

II. Effect of Chelating Divalent Cations on Binding of Monoclonal Antibodies to P-Selectin: Two microtiter plates were coated with affinity purified P-selectin as above. Plate 1 was blocked with 200 µl/well PBS+1% BSA, while plate 2 was blocked with 200 µl/well DPBS+1% BSA (DPBS contains $Ca^{++}$ and $Mg^{++}$). After 1 hr, the plates were washed (all washes for plate 1 were PBS, for plate 2, with DPBS. 25 µl of 25 mM EDTA in PBS+1% BSA was added to the wells of plate 1, and 25 µl of DPBS+1% BSA was added to plate 2. After 1 hr, 25 µl of dilutions of the appropriate antibody were added to the wells of either plate. Dilutions for plate 1 were made in PBS+1% BSA, for plate 2 in DPBS+1% BSA. After 1 hr, the plates were washed, and 50 µl of a 1 to 1000 dilution of sheep anti-mouse IgG horseradish peroxidase conjugate (dilutions for plate 1 were made in PBS+1% BSA, for plate 2 in DPBS+1% BSA) was added. After 1 hr, the plates were washed, and 50 μl of the peroxidase substrate TMB (3,3',5,5'-tetramethylbenzidine, KIRKEGAARD AND PERRY LABORATORIES) was added. After the color had developed to the appropriate level, the substrate reaction was quenched by the addition of 25 μl of 1M phosphoric acid and the absorbance at 450 nm was read.

Figure 4:
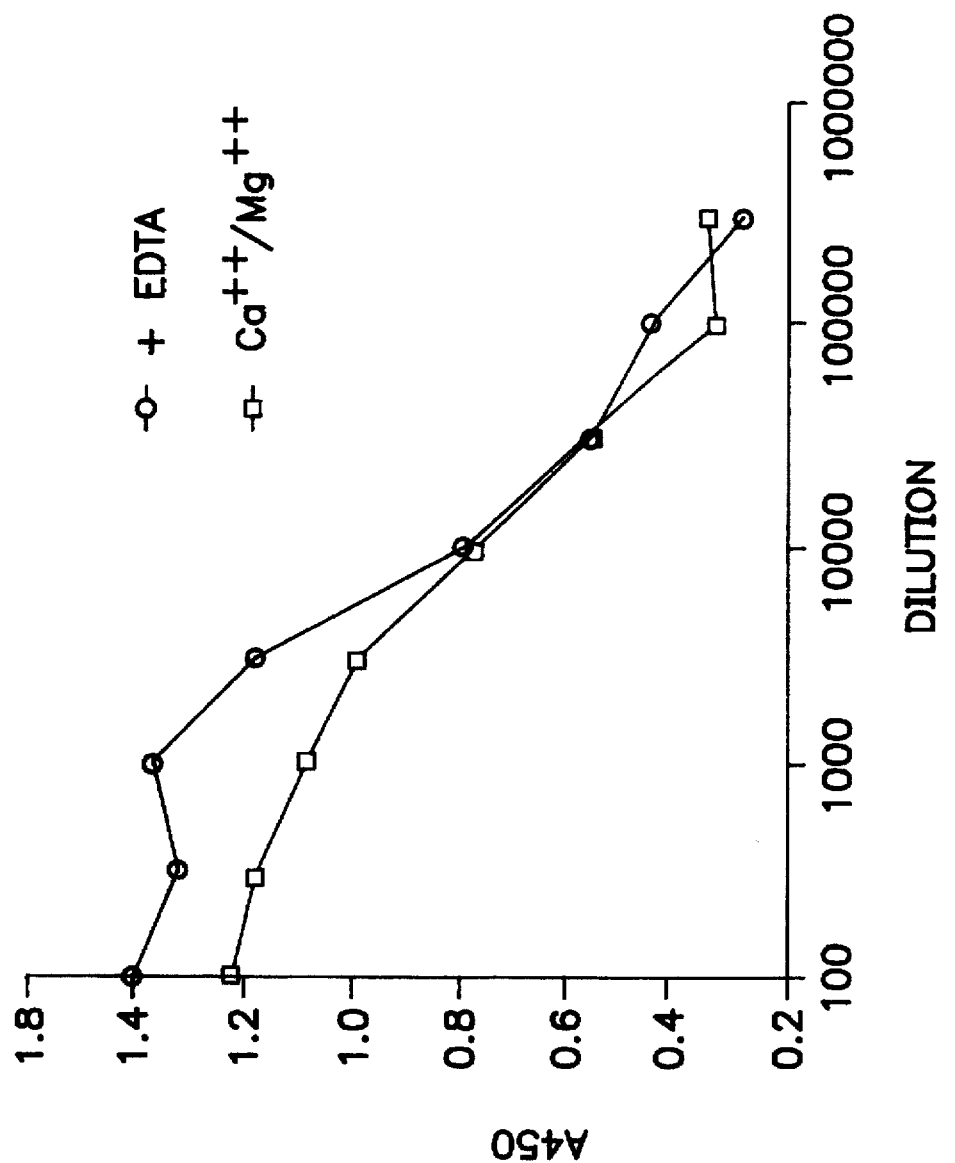
FIG. 4 shows the binding of the monoclonal antibody mu MAb PB1.3 to P-selectin: effect of chelating divalent cations with EDTA. In the plot the open symbols (lower trace) is binding in the presence of $Ca^{++}$ and $Mg^{++}$, while the filled symbols (upper trace) is binding in the presence of EDTA. Antibody was diluted shown at 1.6 mg/ml.

FIG. 4 shows the binding of the anti-P-selectin monoclonal antibodies to P-selectin in the buffer DPBS, which contains CA$^{++}$ and Mg$^{++}$, and in PBS+25 mM EDTA, a chelator of divalent metal cations. The concentration of divalent cations present in DPBS is more than sufficient to support neutrophil adhesion to P-selectin (Geng et al., 1991), while the chelator EDTA, at 25 mM, is more than sufficient to block neutrophil adhesion to P-selectin. The binding of all of the monoclonal antibodies to P-selectin is little affected by the presence of EDTA, demonstrating the Ca$^{++}$ is not required to be present for binding to occur. Mu MAb PB1.3 is a blocking antibody, that is, it is able to block the binding of neutrophils P-selectin, for example on activated platelets. The PNB1.6 is a non-blocking antibody. The ability of 84/26 to block the binding of neutrophils to P-selectin has not yet been fully characterized. In contrast, of the anti-P-selectin monoclonal antibodies described by Geng et al., only the non-blocking antibody S12 is able to bind in the absence of Ca$^{++}$.

III. Effect of the Peptide CQNRYTDLVAIQNKNE (SEQ ID No: 1) on the Binding of mu MAb PB1.3 to P-Selectin: A microtiter plate was coated with affinity purified P-selectin as above, blocked with 200 μl/well DPBS+1% BSA for 1 hr, and washed. Dilutions of mu MAb PB1.3 in DPBS+1% BSA were mixed with either 0.35 mg/ml CQNRYT-DLVAIQNKNE (SEQ ID No: 1) in PBS, or as a control, PBS alone. After 1 hr, 50 μl of each antibody dilution was added to the microtiter plate, and incubated for 1 hr. The plate was washed with DPBS, and a 1 to 1000 dilution of sheep anti-mouse IgG horseradish peroxidase conjugate in DPBS+ 1% BSA was added. After 1 hr, the plate was washed, the substrate TMB was added, and the color development was stopped and the plates read as above.

Figure 5:
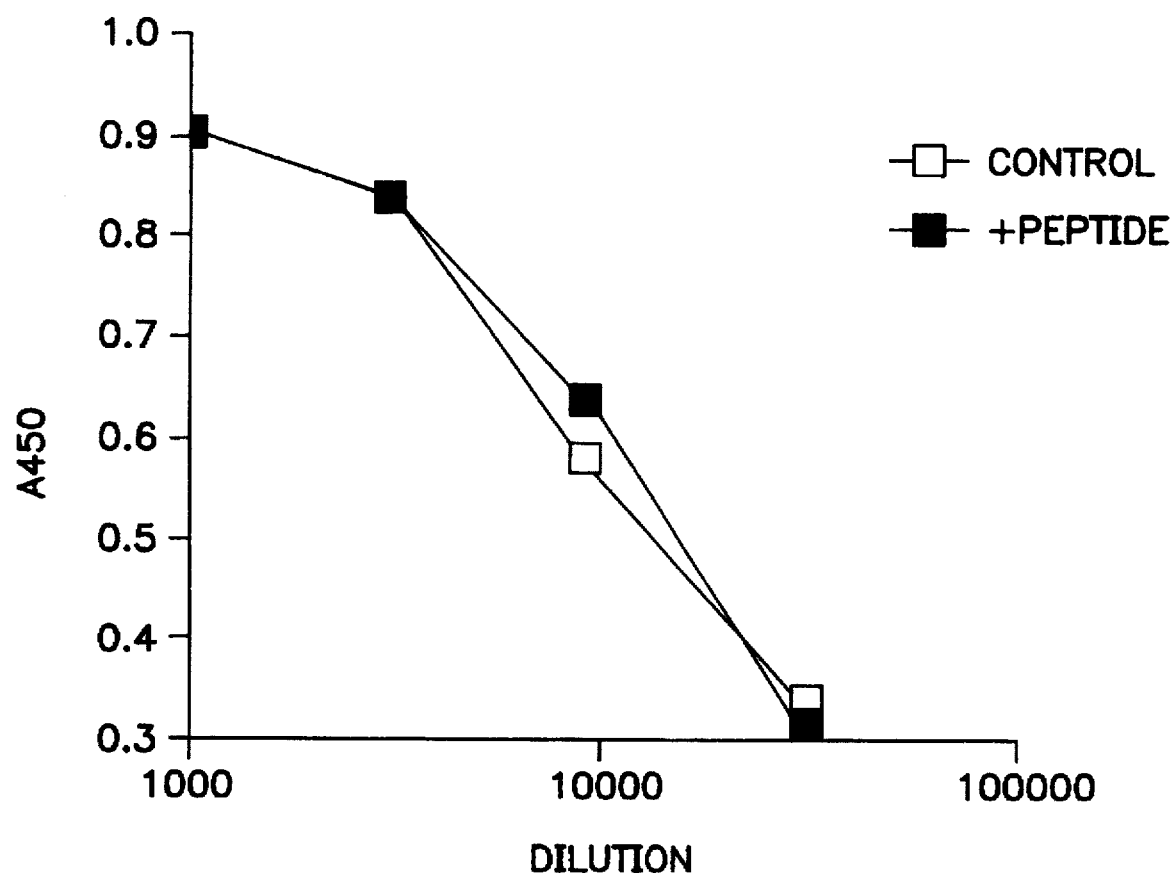
FIG. 5 shows the effect of the peptide CQNRYT-DLVAIQNKNE (SEQ ID No. 1) on the binding of mu MAb PB1.3 to P-selectin. Filled symbols are in the presence of 0.35 mg/ml peptide, open symbols are in the absence of peptides. Indicated dilutions of mu MAb PB1.3 were from a 1.6 mg/ml solution.

FIG. 5 shows that the peptide CQNRYTDLVAIQNKNE (SEQ ID No: 1), homologous to residues 19-34 of the lectin domain of P-selectin, has no effect on the binding of mu MAb PB1.3 to P-selectin when the peptide is present at a concentration of 0.35 mg/ml. This distinguishes this particular monoclonal antibody from the monoclonal antibodies G1, G2, and G3, whose binding to P-selectin is partially or completely blocked by this peptide.

IV. Ability of Cytel Mu MAbs PB1.3, PNB1.6, and 84/26 to Block Binding of Each Other to P-Selectin: Microtiter plates coated with affinity purified P-selectin as above were blocked for 1 h with DPBS+1% BSA, and washed. 25 μl of a 50 μg/ml solution of mu MAbs PB1.3, PNB1.6, or 84/26 in DPBS+1% BSA were added to appropriate wells, and incubated for 1 hr. Then, 25 μl of a dilution (in DPBS+1% BSA) of biotinylated antibody was added. The plate was then incubated on a platform shaker for 1 hr. After washing, 50 μl of a 1 to 1000 dilution of a streptavidin horseradish peroxidase conjugate was added, and incubated for 1 hr. After washing with DPBS, the plate was developed with the substrate TMB as above.

Figure 6A:
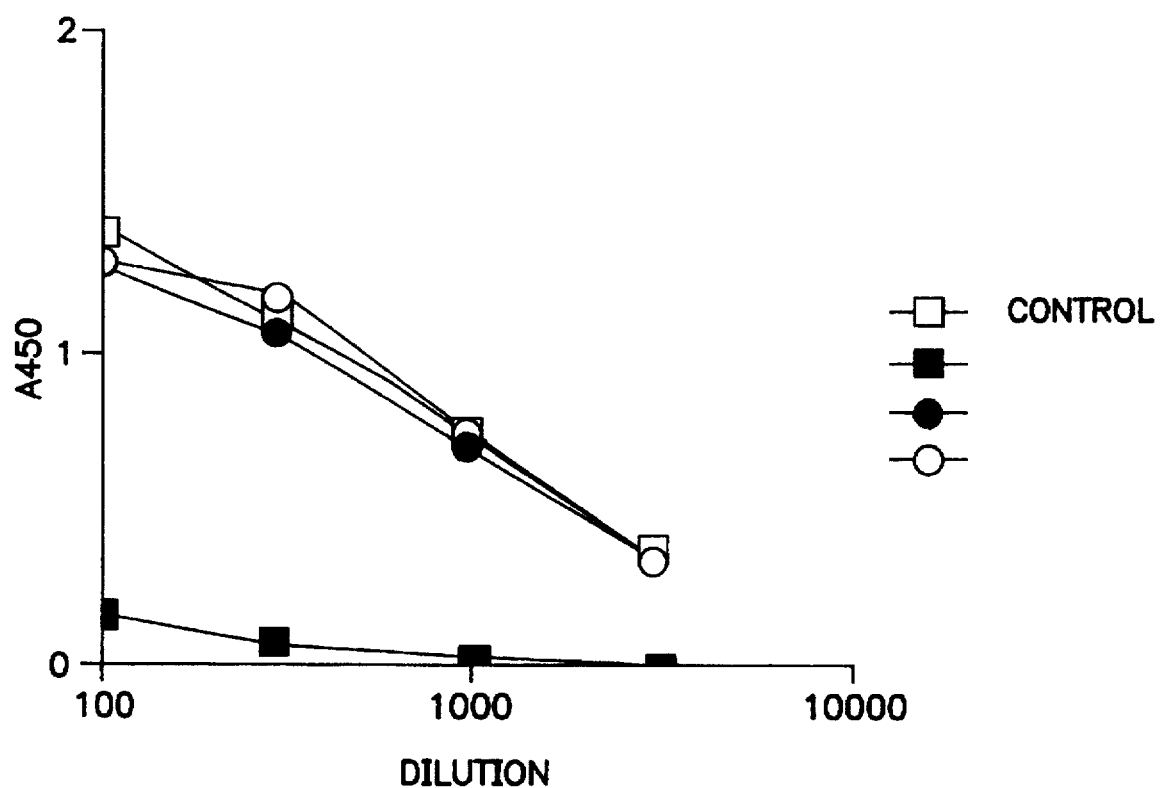
FIGS. 6A, 6B and 6C show the ability of monoclonal antibodies to cross-block binding to P-selectin. Blocking antibodies were present at 50 sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".
Figure 6B:
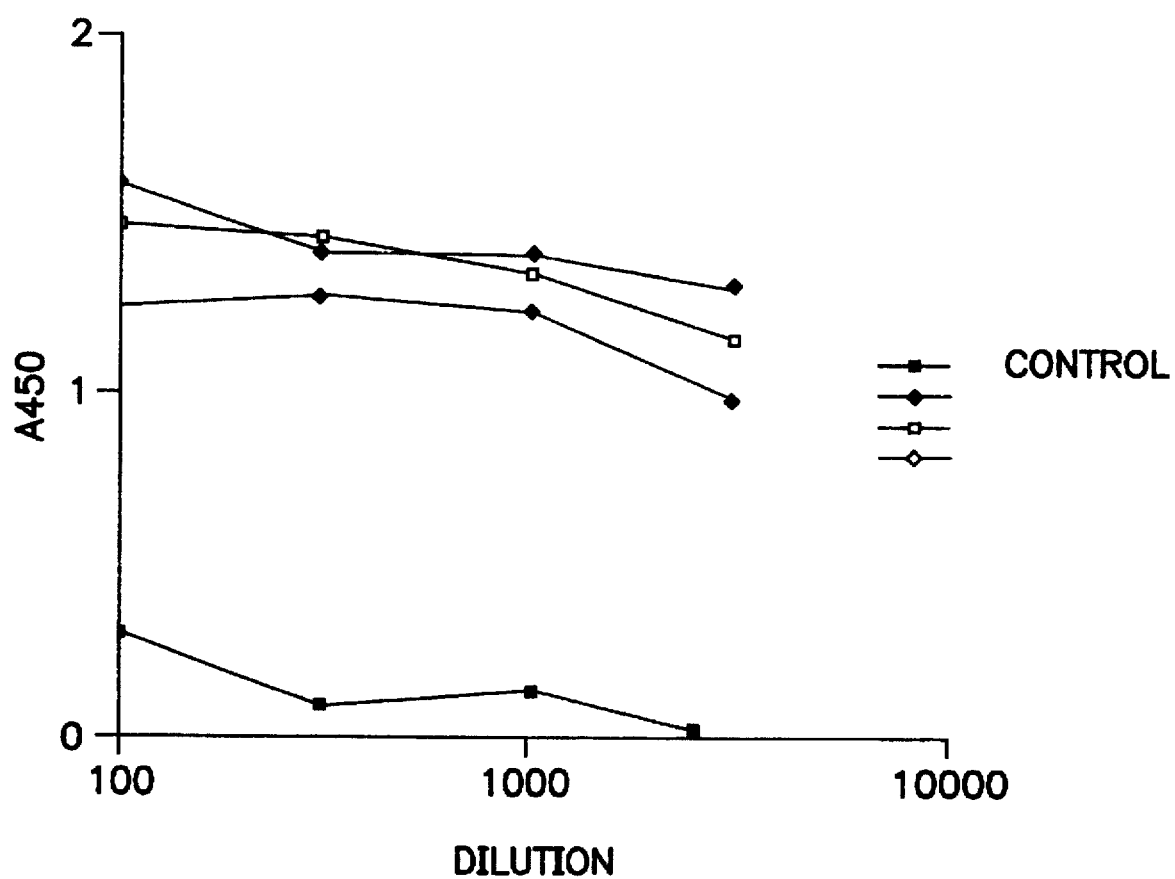
Figure 6C:
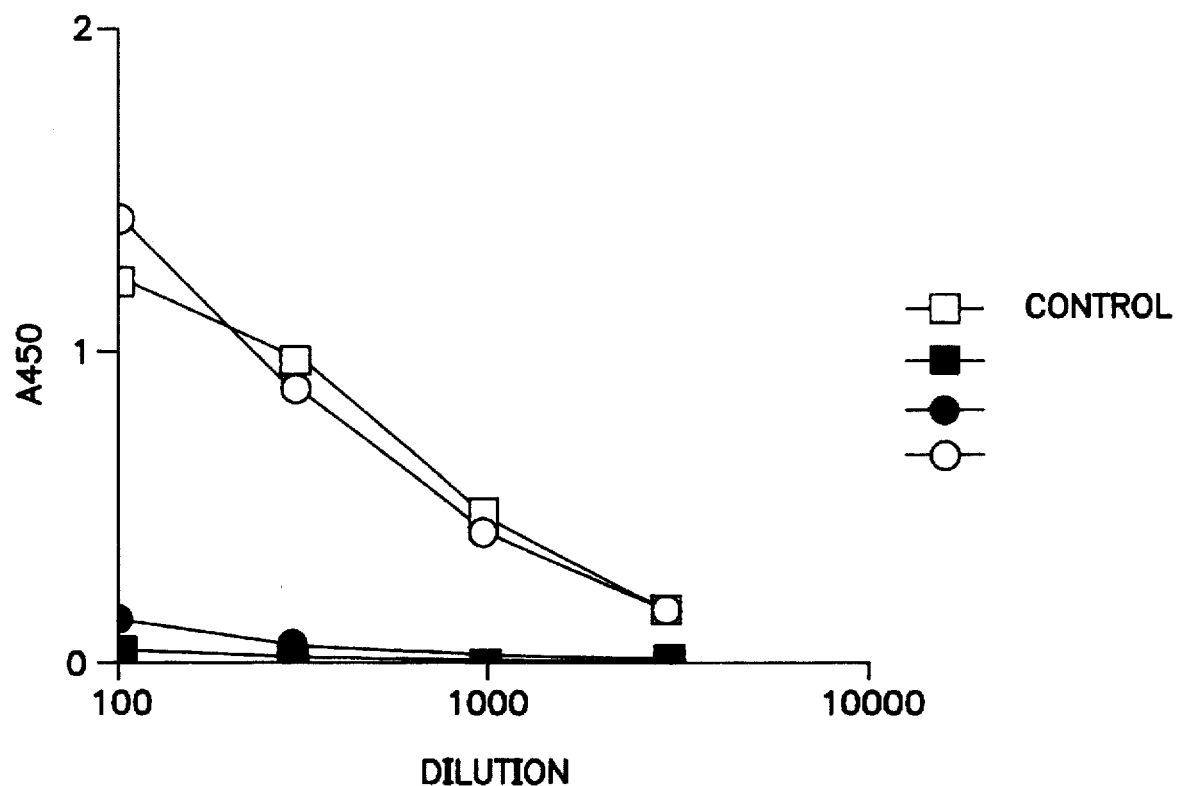
Figure 7A:
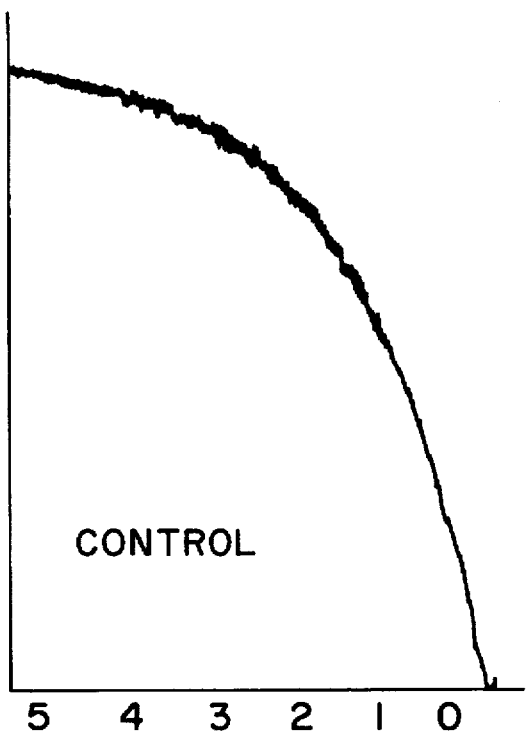
Figure 7B:
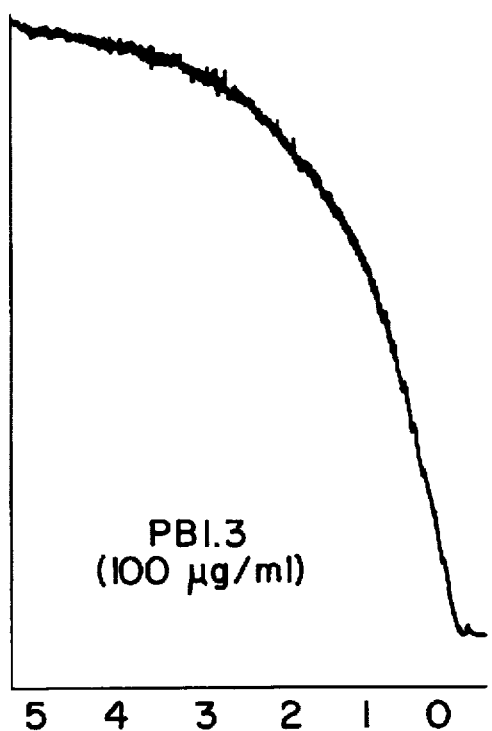
Figure 7C:
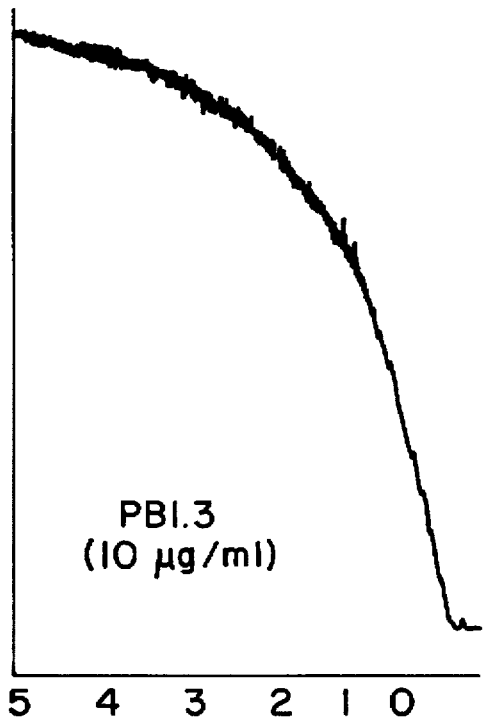
Figure 7D:
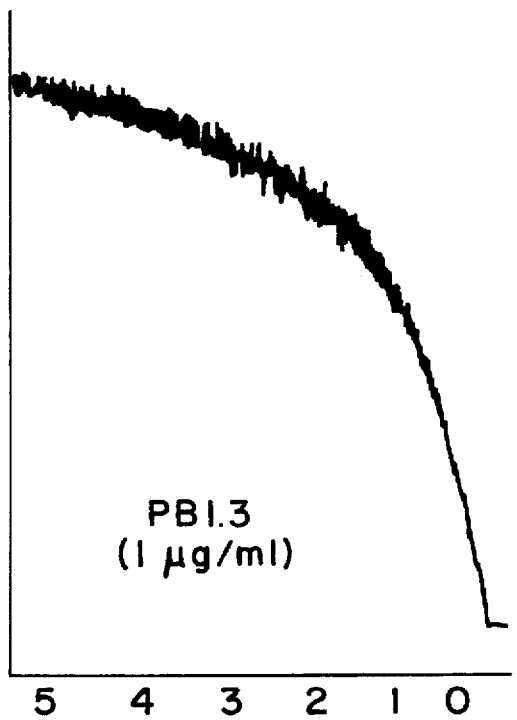

FIG. 6 shows the ability of the mu MAbs PB1.3, PNB1.6, and 84/26 to interfere with the binding of each other to P-selectin. FIG. 6A shows that only mu MAb PNB1.6 is able to block the binding of biotinylated mu MAb PNB1.6 to P-selectin, demonstrating that mu MAbs PB1.3 and 84/26 must recognize different epitopes from mu MAbs PNB1.6. Likewise, In FIG. 6B, mu MAb PB1.3, but not mu MABs PNB1.6 or 84/26, is able to block the binding of biotinylated PB1.3 to selectin, demonstrating that the other two monoclonals must recognize different epitopes. FIG. 6C, both mu MAbs 84/26 and PB1.3, but not mu MAb PNB1.6, are able to block the binding of biotinylated mu MAb 84/26 to P-selectin.

V. Blocking P-selectin Antibodies do not Inhibit Thrombin-Induced Aggregation of Human Platelets:

This example demonstrates that the P-selectin antibodies, mu MAbs PB1.3 and PNB1.6 do not inhibit thrombin-induced aggregation of platelets. Fresh human platelets were isolated as previously described and suspended in Tyrode-Hepes Buffer, pH 7.2 at a concentration of 2×10$^8$/ml.

Platelet aggregometry was performed in a Lumi aggregometer (CHRONO-LOG CORP.). For the assay, 0.45 ml of the platelet suspension was placed in a standard siliconized cuvette. To this was added 10 μl of the antibody or vehicle control. After 5 min. at 37° C., 0.1 unit of thrombin (Human, SIGMA) was added and aggregation was recorded.

When platelet aggregation was measured under control conditions, in the absence of antibody, an aggregation response of 71 units was obtained. An equivalent extent of aggregation was obtained in the presence of 10 μl of undiluted culture supernatants from cells producing mu MAb PB1.3 antibody (FIG. 7). Different concentrations of mu MAb PB1.3 (1–100 μg/ml) were added to the platelet suspension. At no concentration of mu MAb PB1.3 was platelet aggregation different from the response determined in the absence of antibody (FIG. 7).

EXAMPLE 9

In vivo Protective Effects of Blocking P-Selectin Antibody, mu MAb PB1.3 in Feline Myocardial Ischemia and Reperfusion A model of myocardial ischemia and reperfusion injury in cats was performed according to the methods of Tsao et al. (Circulation 82:1402–1412 (1990)). Briefly, male cats (2.5–3.5 Kg) were anesthetized with sodium pentobarbital (30 mg/Kg, i.v.). An intratracheal tube was inserted through a mid-line incision and all cats were given intermittent positive pressure ventilation by a HARVARD small animal respirator. A polyethylene catheter was inserted into the external jugular vein and the right femoral vein was cannulated and connected to a STATHAM P23Ac pressure transducer for the measurement of arterial blood pressure. A midline thoracotomy was performed, the pericardium was opened and the heart was exposed. A 2–0 silk suture was carefully placed around the left anterior descending artery (LAD) 10–12 mm from its origin. After a 30 min period of stabilization myocardial ischemia was initiated by complete ligation of the LAD for 1.5 h of ischemia followed by 4.5 h of reperfusion. Blocking (mu MAb PB1.3) and non-blocking (mu MAb PNB1.6) anti-P-selectin antibodies were administered intravenously at a dose of 1 mg/kg 10 min prior to the initiation of reperfusion.

The ischemic myocardium was determined as that portion of tissue which did not stain with nitroblue tetrazolium and was expressed as a percentage of the area at risk. Area at risk was determined by reocclusion of the LAD at the end of the reperfusion period followed by the injection of Evans blue dye into the left atrium. The area of risk was, therefore, determined by negative staining.

Endothelial dependent relaxation of coronary artery rings was determined by measuring the acetylcholine-induced relaxation of rings previously contracted with the thromboxane A2 mimetic U46619. Data are expressed as percentage relaxation.

Neutrophil accumulation in the myocardium was measured as the myeloperoxidase activity of polytron homogenized myocardial tissue.

Figure 8:
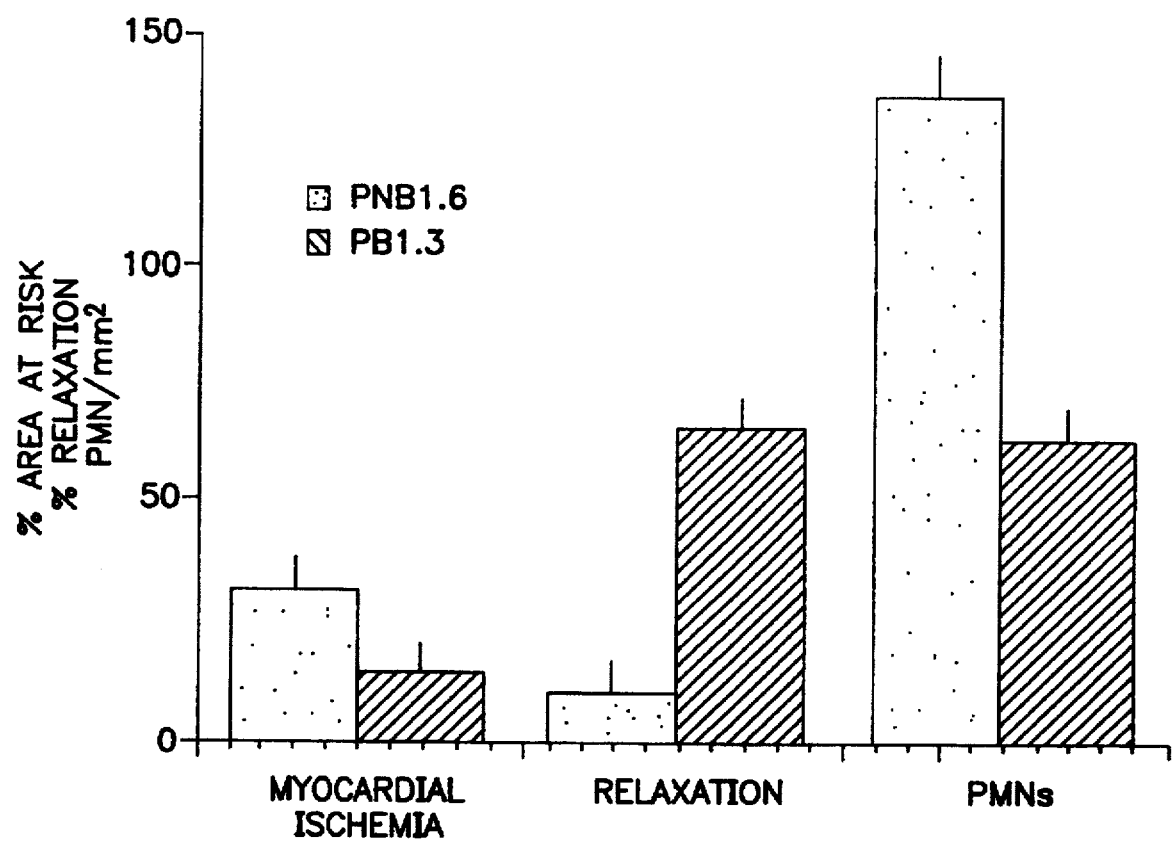

The results of these experiments are shown in FIG. 8. In cats treated with the non-blocking anti-P-selectin antibody mu MAb PNB1.6 the extent of myocardial ischemia was 33±5% of the area at risk. In contrast, the extent of ischemia in PB1.3 treated animals was significantly (P<0.01) less at 15±3% of the area at risk. Endothelial dependent relaxation to acetylcholine was also significantly preserved in ischemic-reperfused coronary arteries taken from cats treated with mu MAb PB1.3 compared to mu MAb PNB1.6 (67±6 vs 11±3%, P<0.01). That these phenomena are attributable to a reduction in myocardial leukocyte infiltration is suggested by a significant (P<0.1) reduction in the number of PMNs in myocardial tissue from mu MAb PB1.3-treated animals (64±7 PMN/mm$^2$) compared with mu MAb PNB1.6 treated animals (136±12 PMN/mm$^2$).

EXAMPLE 10

Production of Humanized Antibodies to P-Selectin

A. Cloning and Sequencing of Mu MAb PB1.3 Variable Regions

The isolation of mu MAb PB1.3 is described in Example 2. Total RNA was isolated from hybridoma cells producing mu MAb PB1.3. The cDNAs encoding the variable regions of the heavy and light chains of mu MAb PB1.3 were amplified by polymerase chain reaction (PCR). The entire mouse variable region was amplified using a mixture of degenerate primers that hybridized within the leader sequence and a single primer that hybridized to the mouse constant region near the V-C junction. See Jones & Bendig, Bio/Technology 9:88–89 (1991) and Bio/Technology 9:579 (1991). The PCR fragments were cloned and sequenced. The nucleotide sequences and the corresponding amino acid sequences for the variable regions of the heavy and light chains of mu MAb PB1.3 are given in FIGS. 9 and 10, respectively.

B. Modelling the Structure of the Mu MAb PB1.3 Variable Regions

A molecular model of the $V_L$ and $V_H$ regions of mu MAb PB1.3 was built. The model was built on a SILICON GRAPHICS IRIS 4D workstation running under the UNIX operating system and using the molecular modelling package QUANTA (POLYGEN CORP., USA). The amino acid sequence of the mu MAb PB1.3 variable regions were compared with the sequences of structurally-solved immunoglobulin variable regions. See Tables 1 and 2.

C. Design of Reshaped MAb PB1.3 Variable Regions

Human variable regions were selected that have framework regions most similar to those found in the mu MAb PB1.3 variable regions. The human mAb DEN light chain variable region and the human mAb 21/28'CL heavy chain variable region were selected as frameworks to join the corresponding complementarity determining regions (CDRs) of mu MAb PB1.3. The human framework regions were modified using the methodology described in Monoclonal Antibodies, 2: Applications in Clinical Oncology (Editor A. Epenetos: Chapman & Hall, 1992, which is incorporated herein by reference; see especially, Bendig et al., The Humanization of Mouse Monoclonal Antibodies by CDR-Grafting: Examples with Anti-Viral and Anti-Tumor Cell Antibodies contained therein, which is incorporated herein by reference). The alignment of amino acids of the variable regions leading to the design of the reshaped humanized PB1.3 variable regions are given in Tables 1 and 2.

Three versions of the heavy chain variable region were modelled and were designated CY1748RH$_A$, CY1748RH$_B$, and CY1748RH$_C$. The nucleotide sequences and corresponding amino acid sequences of these variable regions and signal peptides are given in FIGS. 11, 12, and 13, respectively. In the case of CY1748RH$_B$ the first two mouse residues conserved in CY1748RH$_A$ (glutamic acid and alanine) were changed back to the original human amino acids (glutamine and valine) found in the donor human FR1. In the case of CY1748RH$_C$, computer modelling suggested that the murine lysine at position 73 might form a salt bridge with residue 55 (aspartic acid) in CDR2. If this were the case, then the lysine would be important for the stabilization of the H2 loop. The human threonine residue at this position would be unable to form such a salt bridge. Therefore, version CY1748RH$_C$ substitutes the murine lysine at position 73 of CY1748RH$_A$. Version CY1748RH$_B$ contains the highest number of human amino acid residues. A summary of the amino acid differences among these three versions of the heavy chain is given in Table 3.

Four versions of the light chain variable region were modelled and were designated CY1748RL$_A$, CY1748RL$_B$, CY1748RL$_C$, and CY1748RL$_D$. The nucleotide sequences and corresponding amino acid sequences of these variable regions and signal peptides are given in FIGS. 14, 15, 16 and 17, respectively. Computer modelling suggested that the murine residue glutamic acid at position 60 might be important in P-selectin binding. This residue was incorporated in version CY1748RL$_A$ but replaced with the original human framework residue serine in version CY1748RL$_B$. The murine aspartic acid residue might have a charge interaction with residue 24 in loop 1 (L1), therefore CY1748RL$_C$ is identical to CY1748RL$_A$ except for the replacement of the mouse residue aspartic acid at position 70 for the human framework amino acid glutamic acid. CY1748LR$_D$ incorporates both these amino acid replacements and of the four versions contains the greatest number of human amino acid residues. A summary of the amino acid differences among these four versions of the light chain is given in Table 4.

D. Subcloning of cDNAs Encoding Heavy and Light Chain Variable Regions into Expression Vectors (1) Construction of Expression Vectors (a) pHCMV-1748RL-KR-neo The expression vector contains the human cytomegalovirus (HCMV) enhancer and promoter to drive transcription of the recombinant immunoglobulin light chain, the coding sequences of the bacterial neo gene to act as a dominant selectable marker during stable transformation, and the SV40 origin of replication to give high levels of transient expression in cos cells. To construct the vector, a HindIII-SacII fragment from a pUC8 vector containing the PstI-m fragment of HCMV (Boshart et al., Cell 41:521–530 (1985)) was converted to an EcoRI-HindIII fragment using appropriate adaptor oligonucleotides. In a three-way ligation, the 1.2 kb EcoRI-HindIII fragment containing the HCMV enhancer-promoter was ligated to a 5.05 kb BamH-EcoRI fragment from pSV2neo (Southern and Berg, J. Mol. App. Genet. 1:327–341 (1982)) and a 0.5 kb HindIII-BamHI fragment containing the $V_L$lys kappa light variable region (Foote and Winter, J. Mol. Biol. 224:487–499 (1992)). The HindIII site in pSV2neo had previously been removed by filling-in with Klenow polymerase producing a vector designated pHCMV-V$_L$lys-neo.

A ~2.6 kb EcoRI fragment of the genomic human kappa region was cloned (Rabbitts et al., Curr. Top. Microbiol. Immunol. 113:166–171 (1984)) and subcloned into a pUC vector, pUCKR17 (Mengle-Gaw and Rabbitts, EMBO J.

6:1959–1965 (1987)). BamHI sites were added to both ends of the fragment using EcoRI-BamHI adapters. This fragment was then inserted into the BamHI site of pHCMV-$V_L$lys-neo, in the appropriate orientation, to create pHCMV-$V_L$lys-$K_R$-neo. To facilitate insertion of reshaped human variable regions, the BamHI site on the 3'-side of the human kappa constant region was removed by filling-in with Klenow polymerase. In the resulting vector, designated pHCMV-1748RL-KR-neo, the HindIII-BamHI fragment containing the $V_L$lys is easily replaced with the VL of a reshaped antibody.

(b) pHCMV-1748-γ1C-neo

The construction of this vector began with the same three way ligation as described above for generation of pHCMV-$V_L$lys-neo above save for the insertion of a 0.7 kb HindIII-BamHI fragment containing the $V_H$lys heavy variable region (Verhoeyen et al., *Science* 239:1534–1536 (1988)); Foote and Winter, supra) in place the 0.5 kb HindIII-BamHI fragment containing the $V_L$lys kappa light chain. The cDNA coding for human γ1 constant region was inserted into the BamHI site to produce a vector designated pHCMV-$V_H$lys-γ1C-neo. cDNA coding for human γ1 constant region was cloned from a human cell line secreting a human γ1 antibody by PCR amplification. BamHI sites were created at each end of the cDNA, and a splice acceptor site and a 65 bp intron sequence were introduced at the 5'-end of the cDNA sequence. The BamHI fragment (1176 bp) containing the human γ1 cDNA plus the splice acceptor site and intron sequence was then cloned into the expression vector. As with the light chain expression vector, the BamHI site at the 3'-side of the human γ1 constant region was removed by filling-in with Klenow polymerase. With this vector, designated pHCMV-1748-γ1C-neo, the HindIII-BamHI fragment containing the unwanted $V_H$lys is easily replaced with the $V_H$ of a reshaped antibody.

(2) Insertion of Immunoglobulin Coding Sequences

Figure 18:
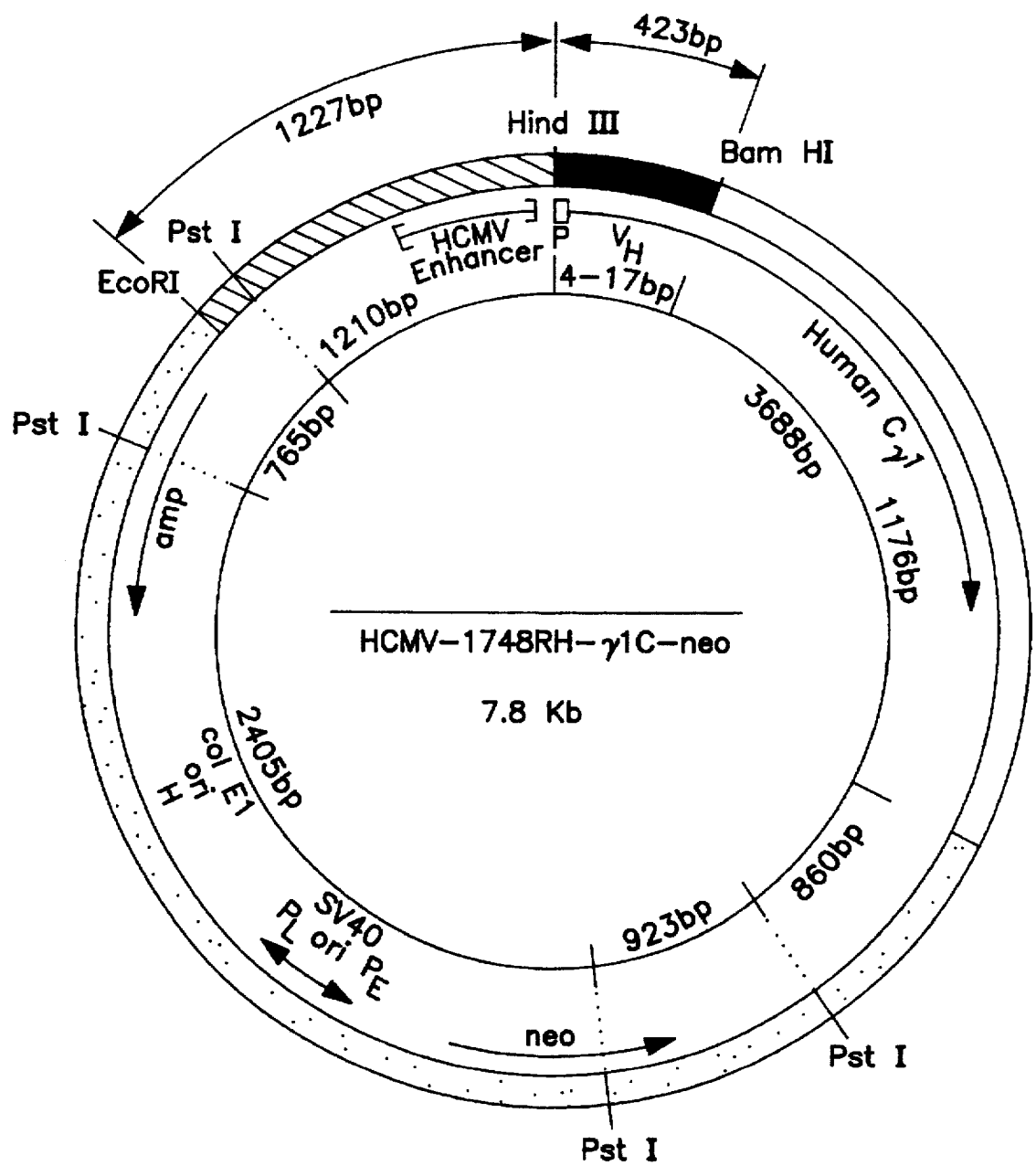
Figure 19:
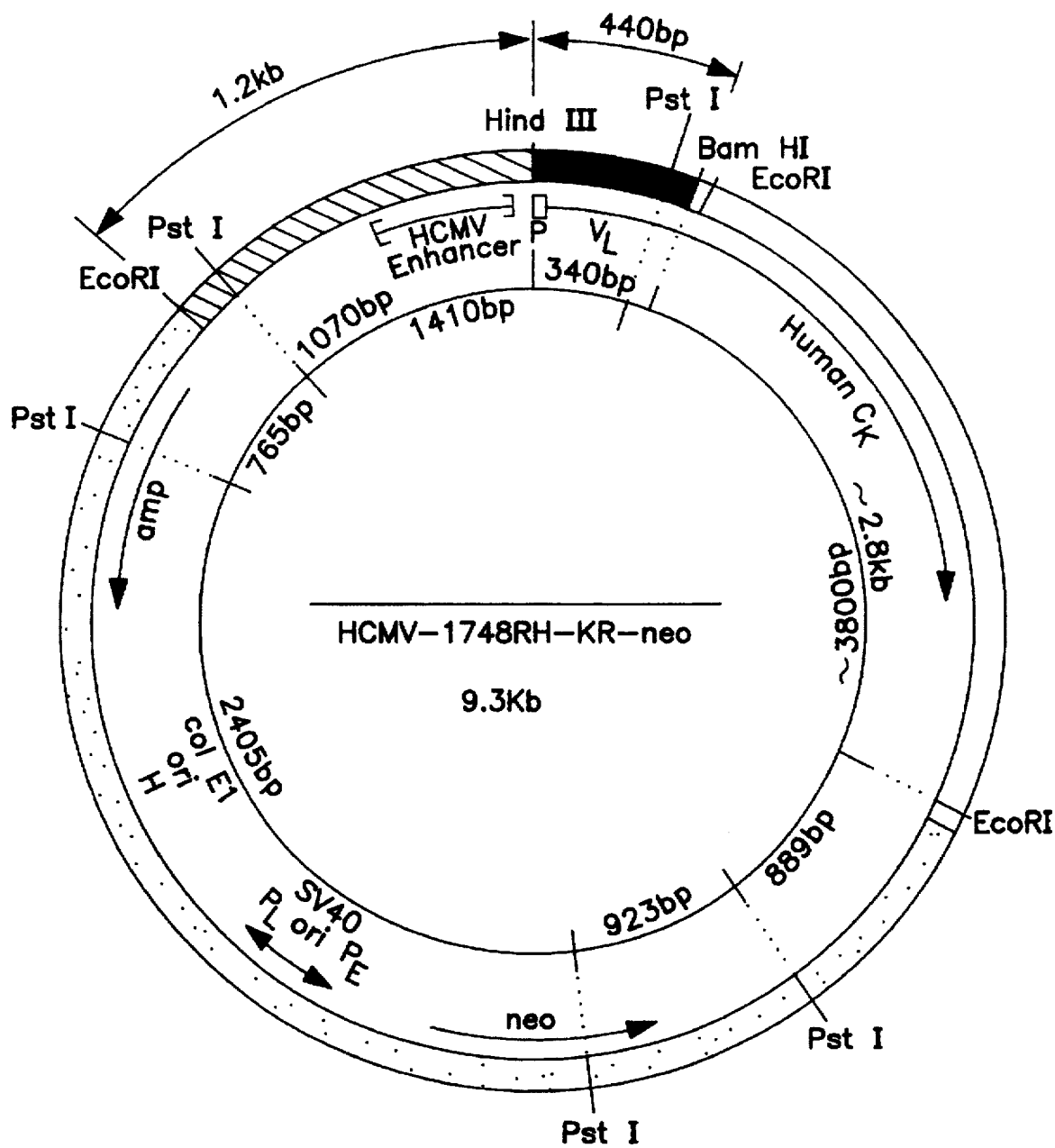

The cDNAs encoding the heavy chain variable region of mu MAb PB1.3 and the three humanized versions were inserted into the expression vector HCMV-γ1C-neo by standard techniques generating expression plasmids HCMV-1747CH-γ1C-neo, HCMV-1748RH$_A$-γ1C-neo, HCMV-1748RH$_B$-γ1C-neo, and HCMV-1748RH$_C$-γ1C-neo. The nucleotide sequence of the human IgG1 constant region cDNA and corresponding protein sequence is given in Ellison et al., *Nuc. Acids Res.*, 10:4071–4079 (1982). The cDNAs encoding the light chain variable regions of CY1747 (PB1.3) and the four humanized versions were inserted into the expression vector HCMV-KR-neo generating plasmids HCMV-1747CL-KR-neo, HCMV-1748RL$_A$-KR-neo, etc. The nucleotide sequence of the human kappa constant region gene and corresponding protein sequence is shown in Hieter et al., *Cell* 22:197–207 (1980) (incorporated by reference in its entirety for all purposes). Schematic maps of the heavy chain and light chain expression vectors are given in FIGS. 18 and 19. By coexpressing appropriate combinations of heavy and light chains, several antibodies can be expressed. For example, coexpression of HCMV-1748RH$_A$-γ1C-neo and HCMV-1748RL$_A$-KR-neo gives rise to the reshaped MAb PB1.3 (H$_A$/L$_A$). Coexpression of HCMV-1747CH-γ1C-neo and HCMV-1747CL-KR-neo gives rise to the chi MAb PB1.3 (i.e., chimeric antibody comprising murine variable domains and human constant domains).

E. Electroporation of COS Cells.

The DNA constructions were tested in COS cells for the transient expression of chi MAb PB1.3 and various reshaped versions of MAb PB1.3 antibodies. DNA was introduced into the COS cells by electroporation using the GENE PULSER apparatus (BIORAD). COS cells were trypsinized and washed once in phosphate buffered saline (PBS). DNA (10 μg of each heavy chain plasmid and appropriate light chain plasmid) and a 0.8 ml aliquot of $1 \times 10^7$ cells/ml in PBS were placed in a sterile GENE PULSER CUVETTE (BIORAD, 0.4 cm gap). A pulse was delivered at 1900 volts, 25 microfarads capacitance. After a 10 minute recovery period at ambient temperature, the electroporated cells were added to 20 ml of DMEM media (GIBCO/BRL) containing 10% fetal bovine serum. After a 48 h incubation, the medium was collected, centrifuged to remove cellular debris, and stored under sterile conditions at 4° C. for short periods of time.

EXAMPLE 11

Analysis of Humanized Antibodies

Media from the transfected COS cells were assayed by ELISA to quantify levels of human antibody produced and analyze capacity to bind to recombinant soluble P-selectin (rsP-selectin). Immulon microtiter plates (DYNATECH, #011-010-3355) were coated with 100 μl/well of a solution of goat anti-human IgG (whole molecule, SIGMA #I-1886) to a final concentration of 12.5 μg/ml or a solution of rsP-selectin (1.2 mg/ml) diluted in Dulbecco's phosphate buffered saline (DPBS). Plates were coated overnight at 4° C. or for 2 h at 37° C. The plates were then washed three times with DPBS. The plates were then blocked with 400 μl/well of DPBS+1% bovine serum albumin (BSA, SIGMA, #A-7888) for one h or longer at room temperature. The plates were then washed three times with DPBS.

Serial dilutions of the monoclonal antibodies in DPBS+ 1% BSA were added to the plates (100 μl/well), and the plates were incubated for 1 h at room temperature. The plates were then washed three times with DPBS. 100 μl/well of a second antibody (goat anti-human IgG peroxidase conjugate, SIGMA #A-8867) diluted 1 to 1000 in DPBS+ 1% BSA was added to the plates, and the plates were incubated for one h at room temperature. The plates were then washed three times with DPBS. 100 μl/well of tetramethylbenzidine peroxidase substrate/$H_2O_2$ (TMB, KIRKEGAARD AND PERRY LABORATORIES #50-76-00) was added to the plates, and the color was allowed to develop for an appropriate period of time (usually 3 to 15 min), and the reaction was quenched by the addition of 100 μl/well of 1-M phosphoric acid. The plates were read at 450 nm in a TILTERTECK MULTISKAN MCC/340.

The concentration of the antibodies produced in all COS cell supernatants was determined by comparing the IgG ELISA results to a human IgG1 antibody (kappa light chain, Sigma #I-3889) of known concentration.

Figure 20:
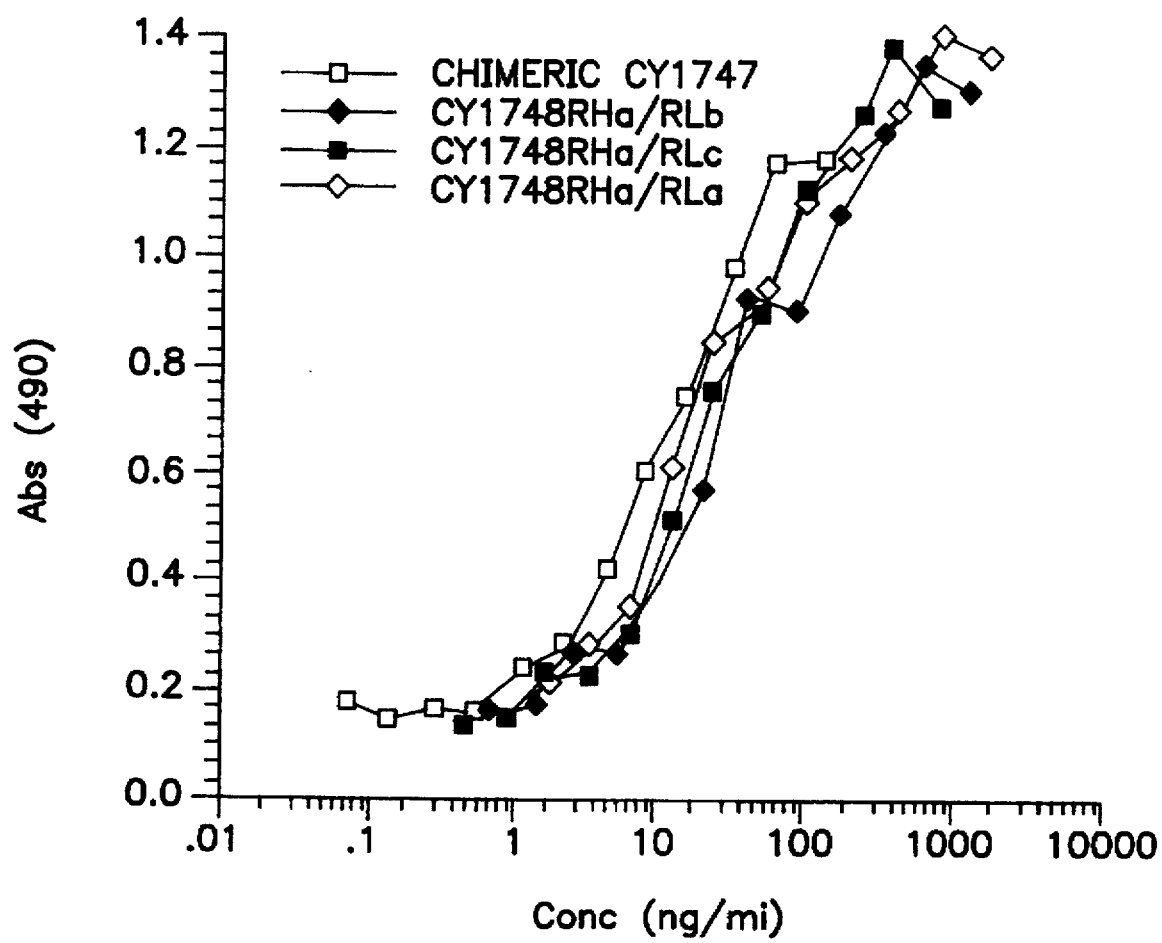
Figure 21:
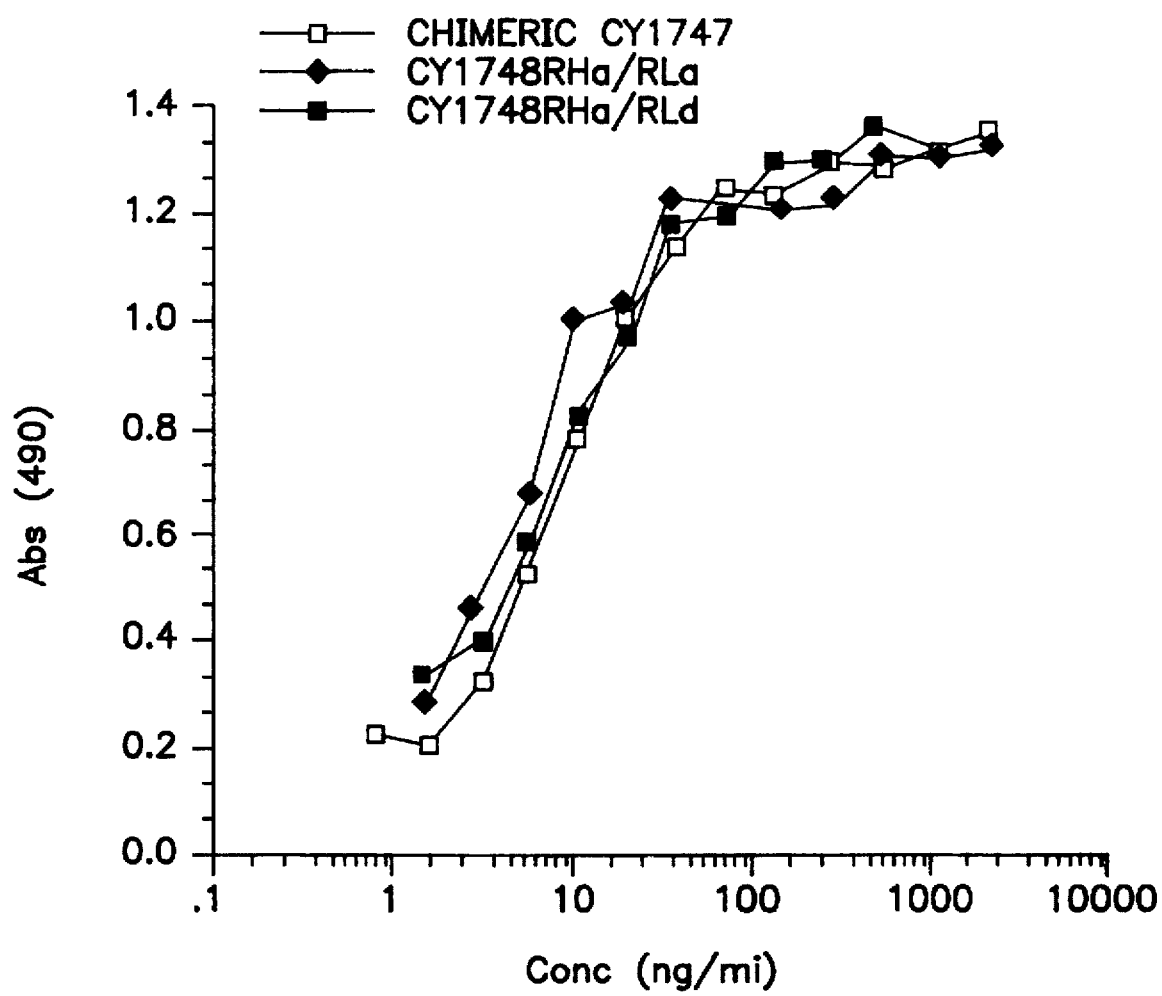
Figure 22:
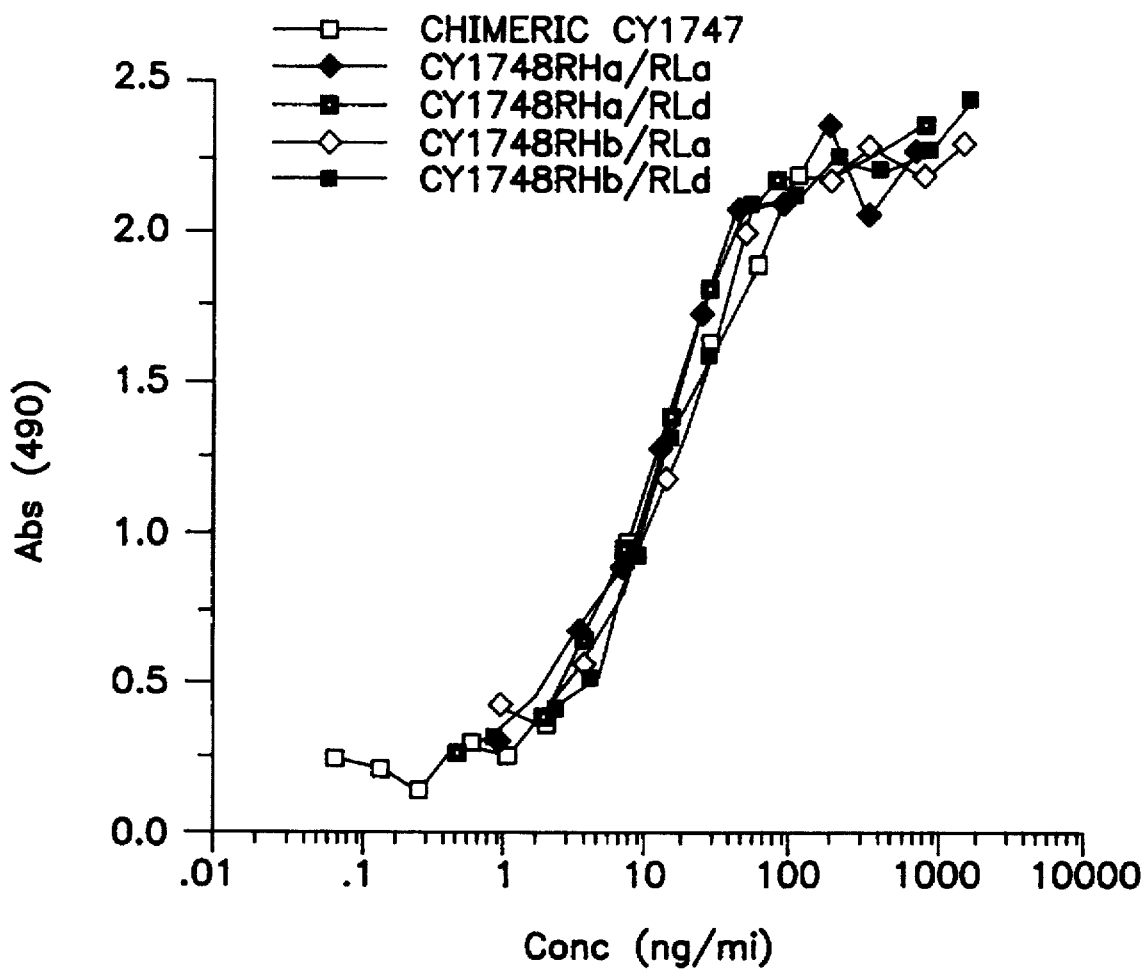

P-selectin binding was plotted as optical density against the concentration of IgG. Binding curves of chi PB1.3 and various reshaped versions of reshaped MAb PB1.3 are given in FIGS. 20, 21, and 22. The objective was to select a humanized antibody showing substantially indistinguishable binding characteristics from chi MAb PB1.3. If more than one humanized antibodies showed such characteristics, the one containing the most human amino acid residues (or the fewest murine amino acids) would be preferred, because this version would be least likely to induce a HAMA response in clinical use. All four of the reshaped light chains coexpressed with heavy chain CY1748RH$_A$ generated antibodies that bound to rsP-selectin as well as the chi MAb PB1.3. Of these, light chain variable region CY1748RL$_D$ was selected for further experiments, because it contains the most human amino acid residues. The heavy chain variable regions CY1748RH$_A$ and CY1748RH$_B$ when coexpressed with light chain variable regions CY1748RL$_A$ and CY1748RL$_D$ also generated antibodies that bound to rsP-selectin to the same extent as chi MAb PB1.3 (FIG. 22). Of these heavy chains, the CY1748RH$_B$ heavy chain is preferable because it contains the most human amino acid residues. Thus, a preferred humanized antibody is formed from light chain D and heavy chain B and is designated reshaped MAb PB1.3 (H$_B$/L$_D$).

EXAMPLE 12

Stable Expression of Reshaped MAb PB1.3 (H$_B$/L$_D$) in CHO Cells

A. Introduction of Humanized Immunoglobulin chains in CHO Cells (1) Construction of Vectors (a) pHCMV-1748RH-γ1C-dhfr This vector is identical to pHCMV-1748RH-γ1C-neo described in Example 11 except that the neo gene is replaced by the dihydrofolate reductase (dhrf) gene linked to a defective SV40 promoter-enhancer sequence. In order to remove the enhancer sequence from the SV40 early promoter, the plasmid DNA, pSV2-dhfr (Subramani et al., Mol. Cell. Biol. 1:854–864 (1981)) was digested with SphI and PvuII, filled-in with Klenow polymerase, and self-ligated to yield pSV2-dhfr-ΔE. A ~3.7 kb EcoRI fragment containing the HCMV promoter, the V$_H$lys heavy chain variable region, and a genomic DNA clone of the human γ1 constant region was excised from the plasmid pHCMV-V$_H$lys-γ1-neo with EcoRI. This fragment was ligated to EcoRI-digested pSV2-dhfr-ΔE to create pHCMV-V$_H$lys-γ1-dhfr. The genomic clone of the γ1 constant region was replaced with a BamHI fragment containing the cDNA clone of the human γ1 constant region-described in Example 11. The BamHI site on the 3'-side of the human γ1 constant region was then removed by filling in with Klenow polymerase as in Example 11. The resulting vector was designated pHCMV-1748RH-γC-dhfr. The HindIII-BamHI fragment of this vector containing the unwanted V$_H$lys is easily replaced with the V$_H$ of a reshaped antibody.

(b) pHCMV-1748RH-γ4-dhfr

This vector is identical to pHCMV-1748RH-γ1C-dhfr described above, but for the replacement of the cDNA clone of the human γ1 constant region with a genomic clone of the human γ4 constant region. To construct the vector, a ~7.0 HindIII fragment of DNA containing the genomic clone of the human γ4 constant region (Brüggeman et al., J. Exp. Med. 166:1351–1361 (1987)) was subcloned into the HindIII site of pUC19 to create a plasmid called 428D. Because the human γ4 fragment already had a BamHI site near its 3'-end, the subclone was inserted into pUC19 in the orientation that placed this site distal to the BamHI site in the polylinker of pUC19. The 7.0 kb human γ4 fragment was excised from 428D using BamHI and ligated into pHCMV-V$_H$lys-neo to create the plasmid pHCMV-V$_H$lys-γ4-neo.

The final plasmid was constructed by a three-way ligation of a 5.4 kb BamHI-HindIII fragment containing the HCMV enhancer-promoter and the pSV2-dhfr-ΔE plasmid sequence, a 0.5 kb HindIII-BamHI fragment containing the VH of reshaped human 1748 antibody and the 7.0 kb BamHI-BamHI fragment containing the genomic clone of the human γ4 constant region.

(2) Insertion of Immunoglobulin Coding Sequences

Figure 23:
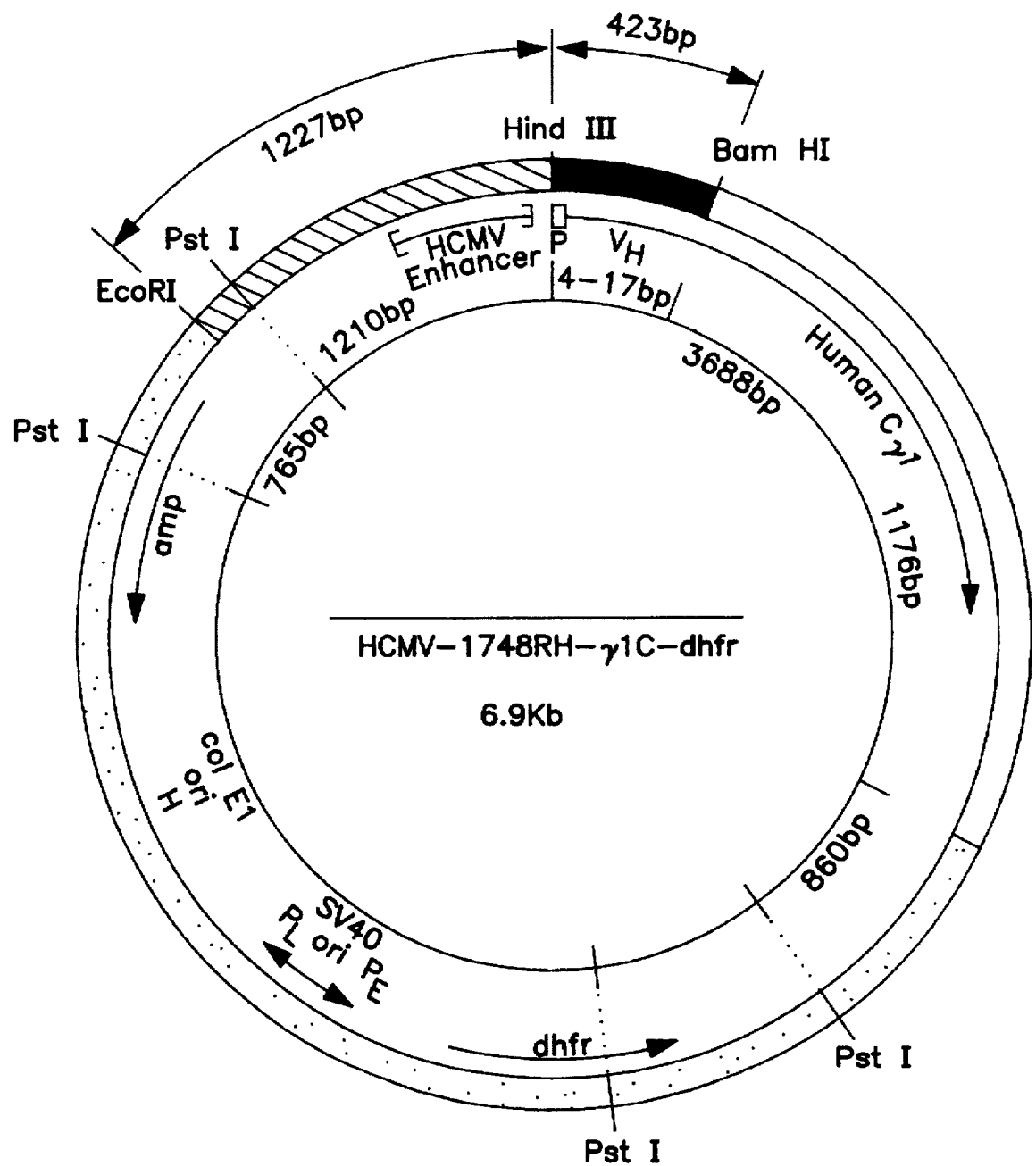
Figure 24:
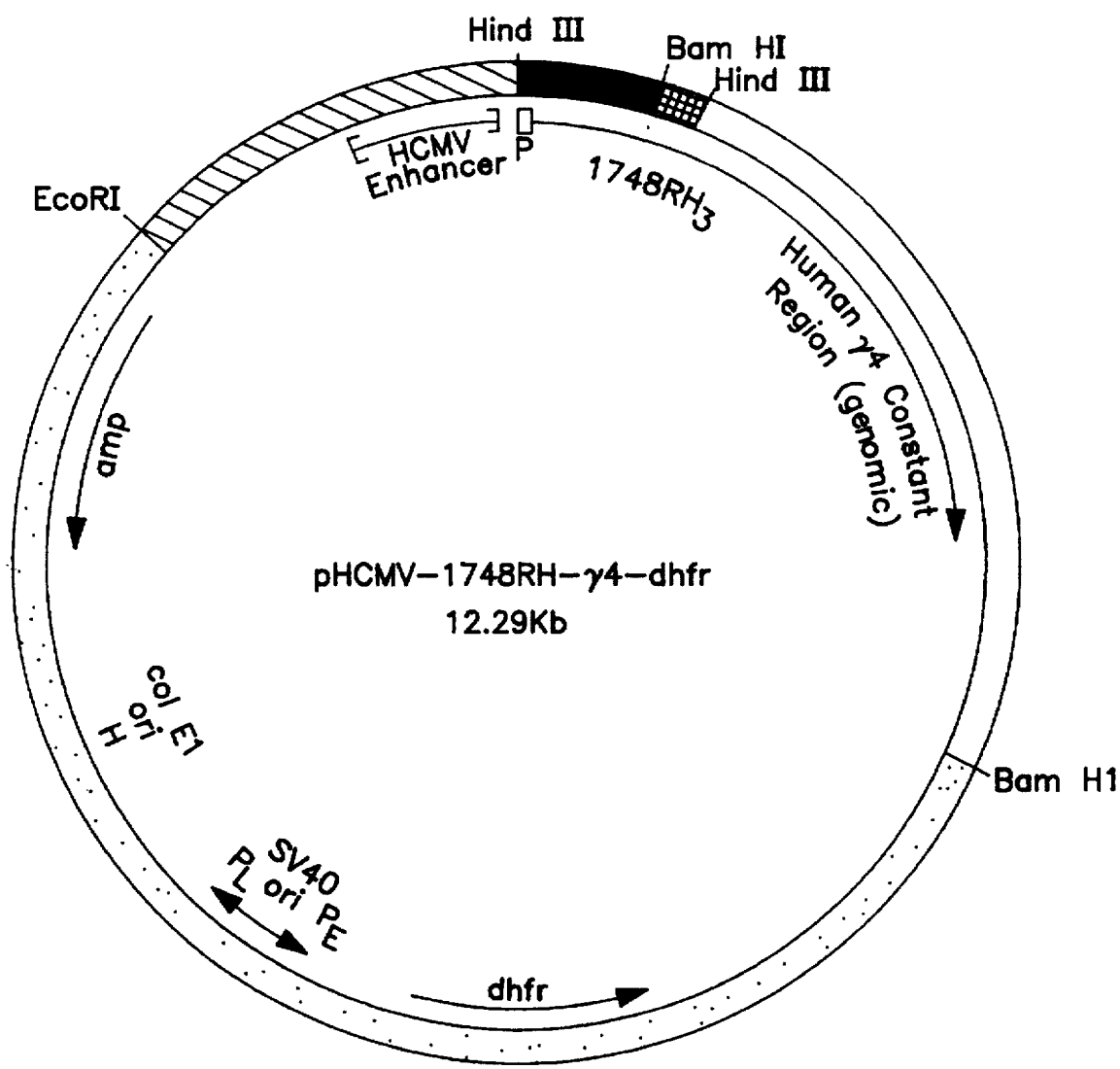

The cDNA encoding 1748RH$_A$ heavy chain variable region was cloned into expression vector HCMV-γ1C-dhfr generating HCMV-1748RH$_A$-γ1C-dhfr. The cDNA encoding 1748RH$_B$ was cloned into expression vectors. HCMV-γ1C-dhfr and HCMV-γ4C-dhfr generating the plasmids HCMV-1748RH$_B$-γ1C-dhfr and HCMV-1748RH$_B$-γ4C-dhfr, respectively. The nucleotide sequence of the human IgG4 constant region gene and corresponding amino acid sequence is given by Ellison et al., DNA, 1:11–18 (1981). The vector HCMV-γ1C-dhfr expresses an IgG1 isotype antibody and vector HCMV-γ4C-dhfr expresses an IgG4 isotype antibody when they are each coexpressed with the kappa light chain vector. The schematic maps of the dhfr-expression vectors are given in FIGS. 23 and 24, respectively.

CHO dhfr-deficient cells were grown in αMEM (+ nucleosides, GIBCO/BRL) and 10% fetal bovine serum. Plasmid DNA was introduced into the COS cells by electroporation using the GENE PULSER apparatus. CHO cells were trypsinized and washed once in phosphate buffered saline (PBS). DNA (10 μg of each heavy chain plasmid and appropriate light chain plasmid) and a 0.8 ml aliquot of 1×10$^7$ cells/ml in PBS were placed in a sterile GENE PULSER CUVETTE (0.4 cm gap). A pulse was delivered at 1900 volts, 25 microfarads capacitance. After a 10 minute recovery period at room temperature, the electroporated cells were added to 20 ml of αMEM (+ nucleosides)/10% FBS. After a 24–48 h incubation cells were trypsinized and plated into 100 mm dishes in αMEM (– nucleosides)/10% dialyzed FBS (to select for the expression of the dhfr-containing plasmid) supplemented with 500 μg/ml G418 (GIBCO/BRL, to select for the expression of the neo-containing plasmid). Media was changed every 3–4 days until colonies emerged. Single clones were isolated via cloning cylinders, expanded and analyzed for IgG production via ELISA.

Three sets of DNAs were introduced into the CHO dhfr-deficient cells: 1) HCMV-1748RH$_A$-γ1C-dhfr and HCMV-1748RL$_A$-KR-neo expressing reshaped MAb PB1.3 (H$_A$/L$_A$), IgG1 isotype; 2) HCMV-1748RH$_B$-γ1C-dhfr and HCMV-1748RL$_D$-KR-neo expressing reshaped MAB PB1.3 (H$_B$/L$_D$) IgG1 isotype; and HCMV-1748RH$_B$-γ4C-dhfr and HCMV-1748RL$_D$-KR-neo expressing a reshaped MAb PB1.3 (H$_B$/L$_D$), IgG4 isotype.

CHO cells were expanded and seeded into 10-chamber (6000 cm$^2$ total surface area) Nunc cell factories. The medium was harvested at 72 h and passed over a protein-A SEPHAROSE FAST FLOW (PHARMACIA) column. The column was washed and bovine IgG was eluted at pH 4.5. The humanized antibodies were eluted at pH 3.5, dialyzed in PBS or 20 mM acetate, 0.15M NaCl, pH 5.5. Antibody concentration was determined spectrophotometrically and confirmed by an ELISA for human IgG. (A purified human IgG4 antibody (kappa, SIGMA #I-4639) was used as the control for mu MAb PB1.3 (H$_B$/L$_D$) IgG4 isotype.) Purity was confirmed by SDS-PAGE.

B. Competitive Binding Assay

The relative binding affinities of the various versions of reshaped MAb PB1.3 to P-selectin were determined by competitive ELISA assay. The assay measures the concentration of unlabelled antibody that inhibits by 50% the binding of labelled mu MAb PB1.3 to P-selectin.

Two ml of purified MAb PB1.3 (1 mg/ml) was mixed with 100.8 μl of NHS-LC-biotin (1 mg/ml, PIERCE) and incubated overnight at 4° C. The 2.1 ml sample was loaded on a NAP 25 column (size exclusion column, PHARMACIA). The column was eluted with 0.3 ml fractions with PBS. Each fraction was read at 280 nm. The highest O.D. 280 nm fractions were pooled. The biotinylated-MAb PB1.3 was titered against rsP-selectin to select an appropriate concentration to use for the competitive binding assay.

A 96-well plate (MICROTEST III, FALCON #3912) was coated with 50 μl/well of rsP-selectin (diluted to 2 μg/ml in DPBS) overnight at 4° C. or 90 min at 37° C. The plate was inverted and residual fluid was tapped away.

The coated plate and an additional blank plate were blocked with 200 µl/well of DPBS+1% bovine serum albumin (BSA, SIGMA #A-7888), for 1 h at room temperature. The blank plate was inverted and the residual blocking fluid was tapped away. The rsP-selectin coated plate was allow to continue blocking during the antibody dilution period. Serially diluted sample antibodies (in DPBS+1% BSA) were added to the blank plate at 50 µl/well. The initial concentrations of the antibodies were 100 µg/ml. Biotinylated-PB1.3 (diluted to 0.3 µg/ml in DPBS+1% BSA) was added to the sample antibodies in the blank plate, 50 µl/well, and mixed by pipetting up and down. The rsP-selectin coated plate was washed three times with DPBS. The sample antibody/biotinylated -PB1.3 mixture was pipetted into the plate coated with rsP-selectin, 50 µl/well, and allowed to incubate for one h at room temperature. The plate was then washed three times with DPBS.

Streptavidin horse radish peroxidase conjugate (PIERCE #21124) diluted 1:2000 in DPBS+1% BSA was added to the plate, 50 µl/well and allowed to incubate for 1 h at room temperature. The plate was then washed three times with DPBS.

50 µl/well of tetramethylbenzidine peroxidase substrate/ $H_2O_2$ (TMB, KIRKEGAARD AND PERRY LABORATORIES, INC. #50-76-00) was added to the plates, and the color was allowed to develop for an appropriate period of time (usually 3 to 15 min), and the reaction was quenched by the addition of 50 µl/well 1M phosphoric acid. The plates were read at 450 nm in a TILTERTECK MULTISKAN MCC/340.

Apparent binding affinity is expressed as the concentration of antibody that binds rsP-selectin at one-half maximum optical density at 450 nm. The ratio of concentrations at one-half maximum binding of the sample antibody to that of the control (unlabelled PB1.3) antibody provides an estimate of the relative binding affinity of a test antibody to rP-selectin.

Figure 25:
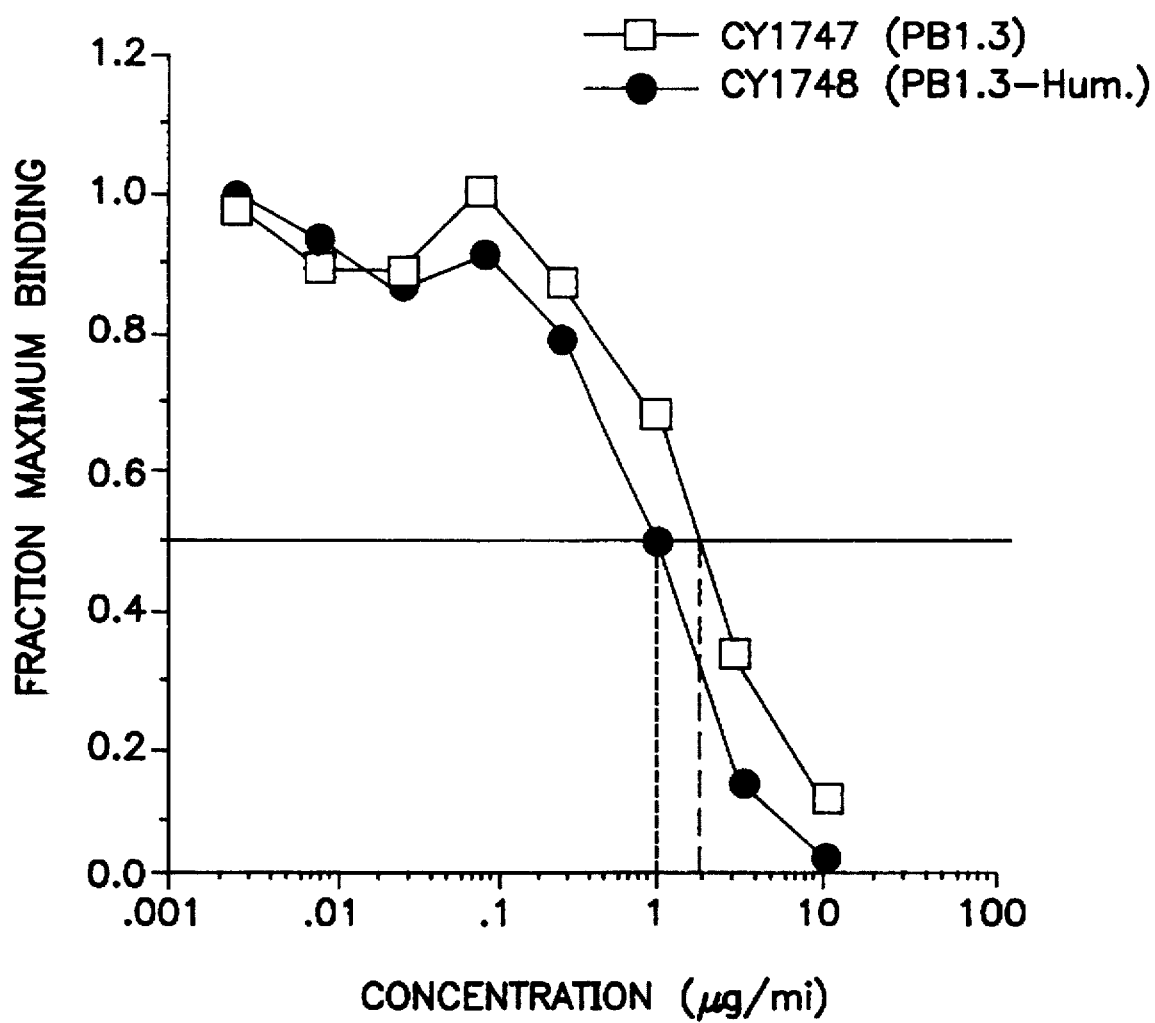
Figure 26:
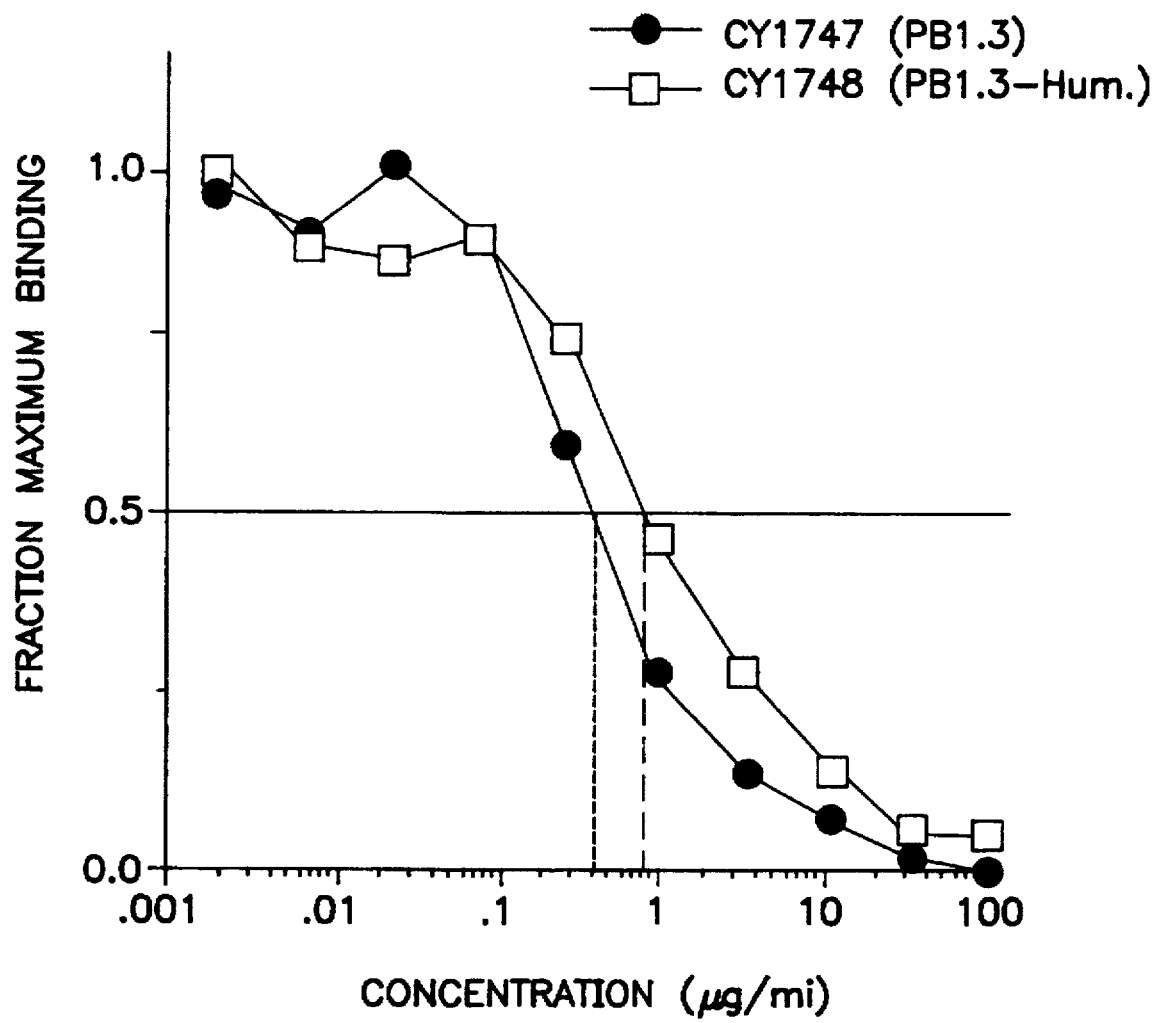

Results from two typical competitive binding experiments are given in FIGS. 25 and 26. In the first experiment, twice as much reshaped MAb PB1.3 ($H_AL_A$), IgG1 isotype (2.0 µg/ml) as PB1.3 (1.0 µg/ml) is needed to inhibit the binding of labelled PB1.3 to 50% of maximum. Therefore this humanized antibody binds rsP-selectin 50% as well as PB1.3. Similarly, in the second experiment PB1.3/($H_BL_D$) (IgG4 isotype) binds to rsP-selectin 50% as well as PB1.3.

EXAMPLE 13

Increasing Antibody Production in CHO Cells Via DHFR Amplification

CHO cells were plated into flasks and allowed to reach confluence before changing media (8 ml for a T-25 cm² flask or 20 ml for a T-75 cm² flask). After incubating the cells for 48–72 h the media was harvested and assayed for IgG production by ELISA. The cells were trypsinized and counted. Antibody production rate was expressed as the amount of antibody in micrograms secreted by one million cells in a 24 h period.

The three to six highest-producing clones were amplified separately, and the remaining seven best clones were pooled and amplified. Cells were plated at a density of $1 \times 10^5$ cells/100 mm dish in selection media. For the first round of amplification cells were plated in three sets of dishes containing αMEM(– nucleosides)/10% dialyzed FBS supplemented with 500 µg/ml G418 and either 10, 20 or 50 nM methotrexate (Sigma #A-6770). Cultures were fed every four days. At 10–14 days single colonies were isolated by cloning cylinders, expanded, and assayed for IgG production by ELISA. Additional rounds of amplification were performed on single clones or pools of clones at methotrexate concentrations 5–10 times the initial methotrexate concentration.

Table 5 provides a summary of the antibody production for the CHO cells expressing three humanized versions of PB1.3. One amplified clone expressing reshaped MAb PB1.3 ($H_BL_D$) (IgG4 isotype) arose from a pool of clones that expressed less than $0.2 \mu g/10^6$ cells/day, amplified to $2.0 \mu g/10^6$ cells/day in the first round, and reached $33.0 \mu g/10^6$ cells/day after the third round. This clone was selected to be grown for large scale production of reshaped MAb PB1.3.

EXAMPLE 14

Bioreactor Run 160-g collagen-coated microcarrier beads (150–200 microns, JRH BIOSCIENCES #60142-100) were hydrated in 800-ml of sterile water for 30 min and the water decanted. The beads were resuspended in 800-ml water and autoclaved for 30 min. After cooling to room temperature the beads were washed twice with sterile serum free αMEM(–nucleosides) and resuspended in 1—1 complete media αMEM(–nucleosides)/5% dialyzed FBS.

The cell line CHO-48B4, which expresses reshaped MAb PB1.3 ($H_BL_D$) (IgG4 isotype) at $33.0 \mu g/10^6$ cells/day, was expanded into 36 T-225 cm² in αMEM(–nucleosides)/10% dialyzed FBS/500 nm methotrexate. When the cells reached confluence they were trypsinized and resuspended in 2–1 complete media (no methotrexate) at a final concentration of $5.0-8.0 \times 10^4$ cells/ml.

1—1 beads, 2–1 cell suspension, and 2–1 fresh complete media were aseptically added to the 10–1 autoclaved vessel of a PROTEUS 2000 BIOREACTOR (WHEATON). The headspace was continuously perfused with air and 5% $CO_2$. Cells were allowed to attach to the microcarriers by programming the Proteus to stir the cell/microcarrier suspension at 70 rpm for 1 min and 0 rpm for 59 min. After a total of 48 cycles, 5–1 media was added to the bioreactor, which was programmed to maintain the suspension at 37° C., pH at 7.0, dissolved oxygen at 30% that of air, and stirred continuously at 50 rpm.

After 3 days the bioreactor was programmed to replace complete media at 5–1/day utilizing a gravity filter attached to the harvest port (to leave microcarriers in the bioreactor). The harvested media was stored at 4° C. until processing. The bioreactor was run for 5–7 days until accumulated cell debris clouded the media harvest (due to aeration damage).

The media harvest was clarified by passing though a MILLIPAK-60 0.45 micron filter (MILLIPORE). 20–1 filtered supernatant was passed over a column (2.5×12 cm) of protein-A SEPHAROSE FAST FLOW (PHARMACIA) at a flow rate of 0.55 1/hr. After all of the supernatant had passed through the column, the column was washed with 1.5–1 PBS (BIOWHITTAKER, #17-516Y) The column was pre-eluted with 8×40-ml 0.2-M sodium acetate, pH 4.5, and eluted with 8×40-ml 0.2-M glycine, 0.5-M NaCL, pH 3.5, both into tubes containing 10 ml 2-M Tris-HCl, pH 8.0. The single fraction with the highest absorbance at 280 nm was dialyzed into 20-mM acetate, 0.15-M NaCl, pH 5.5, and stored at 4° C.

200-mg antibody was harvested per day for 5–7 days. The purification yield was approximately 50%. Therefore, one bioreactor run yields 500–700 mg purified antibody.

EXAMPLE 15

The Effect of Mu MAb PB1.3 on Tissue Injury Produced by Ischemia Reperfusion Following Replantation of the Rabbit Ear New Zealand White rabbits were anesthetized with a combination of ketamine and xylazine followed by infiltration of lidocaine into the base of the ear. The left ear was partially amputated leaving the central artery, vein and a bridge of cartilage intact. All nerves were divided to render the ear totally anesthetic. The ear was then reattached and a microvascular clip was placed across the artery to produce total ischemia. Rabbits were kept in a room maintained at 23.5° C. for 6 h then the microvascular clamp was removed and the ear allowed to reperfuse. Treatment was administered immediately prior to reperfusion with either mu MAb PB1.3 (2 mg/kg) or with either saline or an isotype (IgG1) matched murine monoclonal antibody designated PNB1.6 (2 mg/kg). Ear volume was measured daily for 7 days by water displacement to quantify tissue edema. On day 7 necrosis was estimated as a percentage of total surface area.

Figure 27:
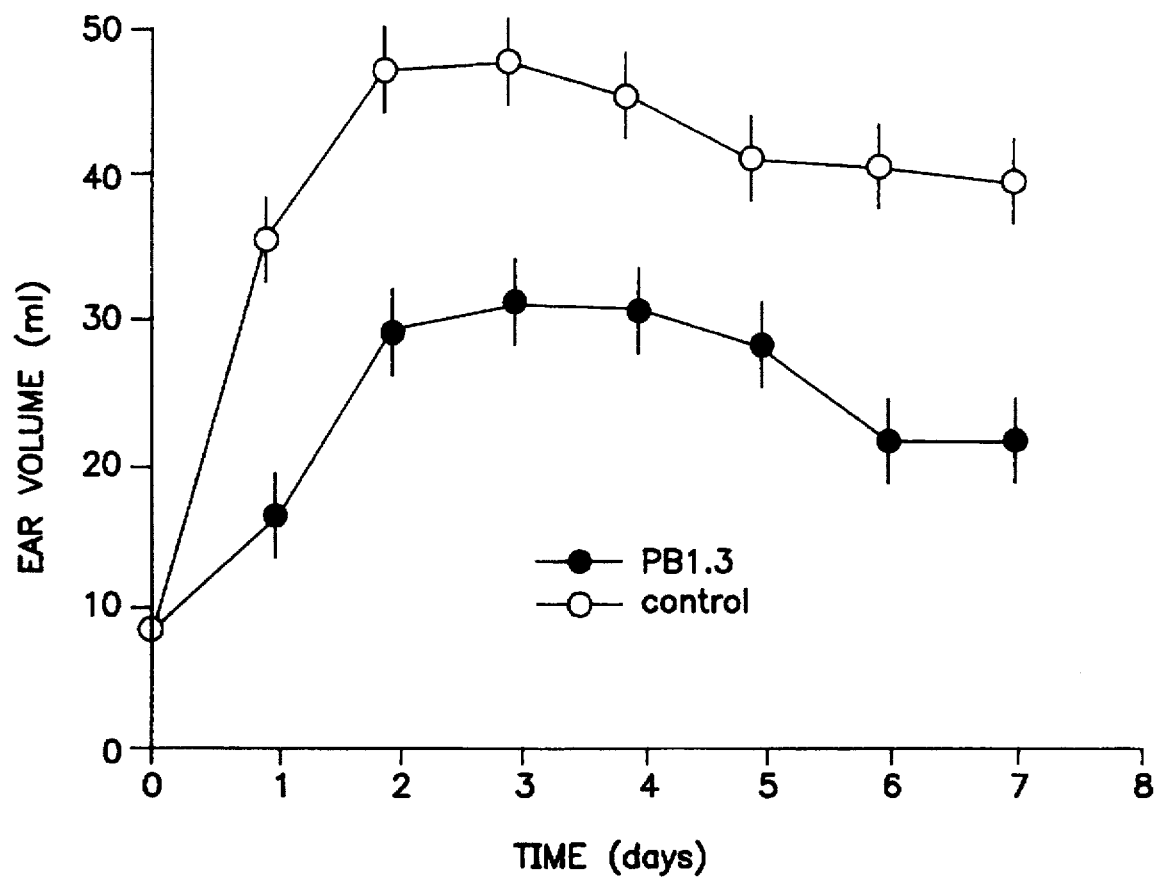
Figure 28:
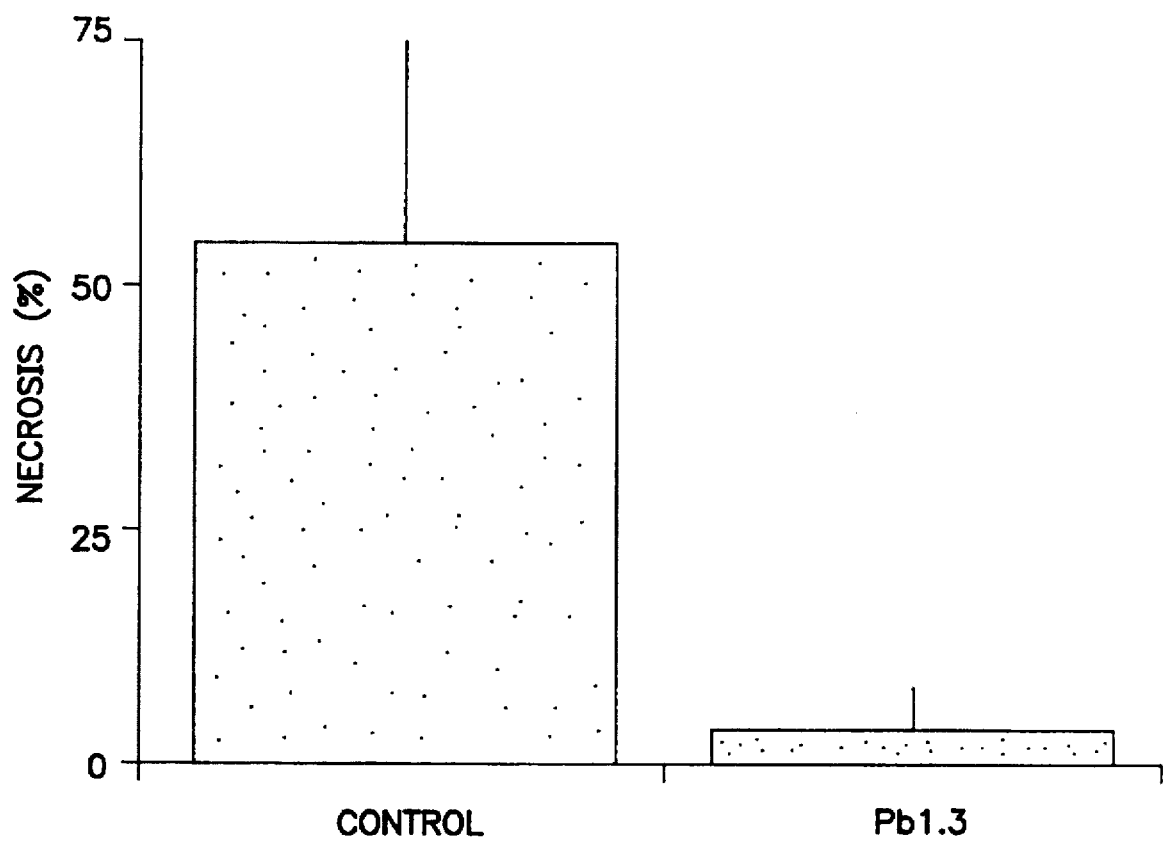

A significant increase in ear volume was determined in control animals administered either saline or PNB1.6 following reperfusion of the ears (FIG. 27). Because no differences between the two control groups were noted, their data have been combined. An increase in edema was also seen in animals treated with MAb PB1.3, the magnitude of the increase was significantly less than that observed in the control group at all time points measured. The extent of necrosis (FIG. 28), measured on day 7, was also significantly reduced in mu MAb PB1.3-treated animals compared with control animals.

Thus, ischemia followed by reperfusion of the replanted rabbit ear produces an edematous response initially followed by extensive tissue necrosis. These two manifestations of tissue injury are substantially and significantly reduced in animals pre-treated with the anti-P-selectin antibody mu MAb PB1.3.

EXAMPLE 16

The Effect of Mu MAb PB1.3 on Vascular Patency Following Ischemia and Reperfusion of the Canine Skeletal Muscle This experiment utilizes a model of ischemia and reperfusion of the isolated canine gracilis muscle. One aspect of the reperfusion injury is a phenomenon referred to as the "no-reflow" phenomenon in which blood flow through the microcirculation of a previously ischemic tissue is absent or severely reduced following reperfusion.

An isolated canine gracilis muscle preparation was utilized as described previously (Carden et al. *Circ. Res.* 66:1436–1444 (1990)). Briefly, adult mongrel dogs were anesthetized with pentobarbital sodium. The skin overlying the gracilis muscle was divided and the muscle was freed from connective tissue by blunt dissection. The obturator nerve was sectioned. The proximal caudal artery and vein were cannulated and all other collateral vessels ligated. The femoral artery cannula was connected to a constant flow perfusion pump and the outflow from the femoral vein drained in to a reperfusion reservoir. Arterial and venous pressures were monitored via side branches and blood flow was adjusted to maintain perfusion pressure at 100 mm Hg. Vascular isolation was assumed complete if arterial perfusion pressure decreased to less than 20 mm Hg when the perfusion pump was switched off.

Microvascular patency was assessed by perfusion of the isolated gracilis muscle with contrast media (india ink) at the end of the experimental protocol. Computerized video imaging was used to quantitate the number of ink-containing microvessels (<10 μm diameter) per muscle fiber in histologic sections obtained from isolated canine gracilis muscles subjected to 4.5 h of continuous perfusion, 4 h of ischemia followed by 0.5 h of reperfusion or ischemia reperfusion in the presence of the anti-P-selectin antibody mu MAb PB1.3 at a concentration of 40 μg/ml in the perfusate.

The ischemia and reperfusion protocol reduced the number of patent microvessels to 36±3% of the value determined in control animals. When mu MAb PB1.3 was included in the perfusate the number of patent microvessels following ischemia and reperfusion was 119±18% of control.

Thus, the anti-P-selectin antibody, mu MAb PB1.3, completely prevented the development of the "no-reflow" phenomenon, determined by the number of patent microvessels, in the ischemic and reperfused canine gracilis muscle.

EXAMPLE 17

The Effect of Mu MAb PB1.3 on Leukocyte Endothelial Cell Interactions Induced by the Degranulation of Tissue Mast Cells I. Methods a) Intravital Microscopy Male Wistar rats (200–250 g) were obtained from Harlan Sprague Dawley, Indianapolis, and were fasted for 12–24 hrs before the surgical procedure. Surgical anaesthesia was induced by an intramuscular injection of ketamine/rompun/acepromazine. A catheter was placed in the left jugular vein, and a tracheostomy was performed to facilitate spontaneous breathing. The abdomen was shaved and washed, and a ¾ inch long incision was made through the midline into the peritoneal cavity, taking care to avoid any bleeding. The rat was placed on a microscope stage specifically designed for the intravital microscopy procedure. A well-vascularized posterior loop of the ileum was exteriorized, and the mesentery draped over a viewing pedestal heated to 37° C. Throughout the experiment, the mesentery was superfused at 2 ml/min with a heated bicarbonate-buffered saline solution (37° C., pH 7.4). Additionally, small pieces of SARAN-WRAP (previously soaked in alcohol and rinsed in saline) were placed over the ileum and mesenteric areas peripheral to the viewed area, in order to keep these areas moist. The microcirculatory beds were observed through an intravital microscope (MIKRON INSTRUMENTS, San Diego) equipped with 10x oculars and a 20x objective (water immersion, numerical aperture 0.4). A high-resolution video system, consisting of a video camera (HITACHI color CCD) clamped onto the microscope, a video timer (AMERICAN VIDEO EQUIPMENT), a VCR (SONY SVO-9500MD) and a monitor (SONY TRINITRON), permitted video recordings of the microscope image. In each mesentery preparation, 3 postcapillary venular segments of approximately 180 μm length were selected for repeated recordings according to the following criteria: (1) A true postcapillary venule receiving blood from confluent capillaries, diameter 15–30 μm; (2) Brisk blood flow, so that individual red blood cells could not be distinguished; (3) Some baseline rolling of leukocytes (less than 8 leukocytes present at any given time in the vascular segment), but no firmly adhering leukocytes. A leukocyte was defined as being firmly adhering if it stayed immobile at the vessel wall for more than 30 seconds.

b) Experimental Protocol

One-minute video recordings of the baseline leukocyte interaction in the selected venules were made at 20 and 25 min after completion of the surgical procedure. All treatments were administered intravenously before the second baseline recording. At 30 min after surgery, infusion of compound 48/80 (SIGMA, catalog #C4257) into the superfusion buffer was begun, and continued throughout the rest of the experiment. This yielded a final concentration of 10 µg/ml at the mesentery, and was done in order to induce mast cell degranulation. Venules were recorded again at 20 and 30 min after the beginning of 48/80 application. The extent of leukocyte-endothelial cell interactions was determined at the end of the experiment by analyzing the recorded video tapes. The number of clearly visible leukocytes (i.e., cells interacting with the vessel wall) was determined from frames frozen at exactly 0, 15, 30, 45, and 60 seconds of the recorded sequence, and the mean from these five determinations was calculated. Hence, counted leukocytes included rolling cells as well as those firmly adherent.

c) Statistics

Each experimental group contained 5–6 animals with 2–3 venules from each animal. The mean and its standard error is given. Significant differences among group means were tested through analysis of variance followed by the Tukey-Kramer's HSD test. Differences before and after treatments in individual venules were studied by paired t-tests. All tests were run using JMP software running on a MACINTOSH IIsi, and significance was accepted at p<0.05.

II. Results

Topical application of compound 48/80 to the rat mesentery resulted in visible degranulation of more than 90% of the mast cells, which took place within 3 min after application. Subsequently, an increase in leukocyte rolling and adhesion was seen. No significant difference in leukocyte accumulation was detected between the 20 and 30 minute timepoints post 48/80 application, the mean of these two timepoints was therefore used in the statistical analysis. The venule-to venule variability in the model was quite high, with baseline interaction ranging from 0 to 4.8 leukocytes present in individual venules, and mast cell-induced interaction ranging from 2.8 to 25.6 leukocytes present in the PBS-treated group (coefficient of variability, CV, 37%). Animal means showed much lower variability (CV, 16%); hence, each individual venule was treated as a separate experimental entity for statistical purposes.

Figure 29:
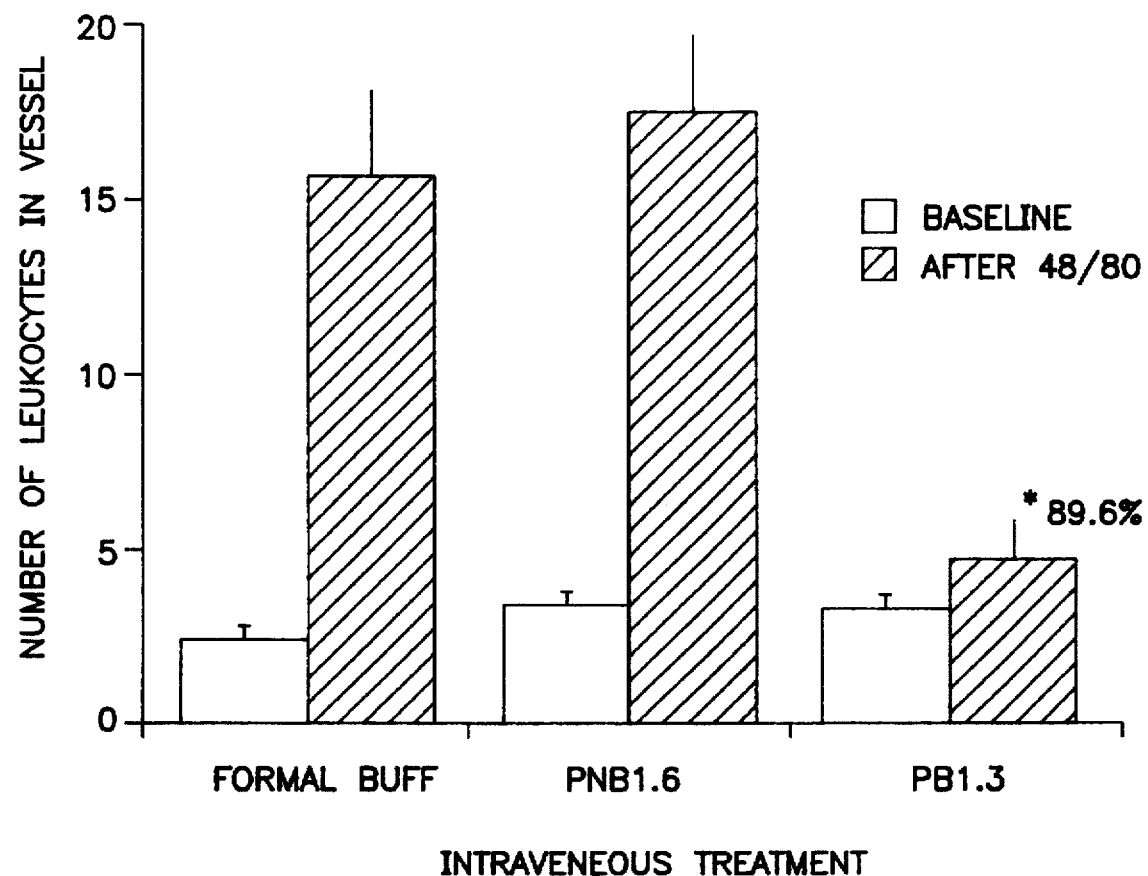

As seen in FIG. 29, intravenous treatment with mu MAb PB1.3 inhibited the mast cell-induced intravascular leukocyte accumulation by 90% when compared with the formulation buffer control group. The non-reactive antibody P6H6 did not have any effect in this model.

Thus, administration of the anti-P-selectin antibody, mu MAb Pb1.3, to rats completely prevents the interaction of leukocytes with the vascular endothelium and their subsequent migration into the tissues induced by application of the mast cell degranulating agent 48/80.

EXAMPLE 18

Mapping the Epitope of Mu MAb PB1.3

Figure 30:
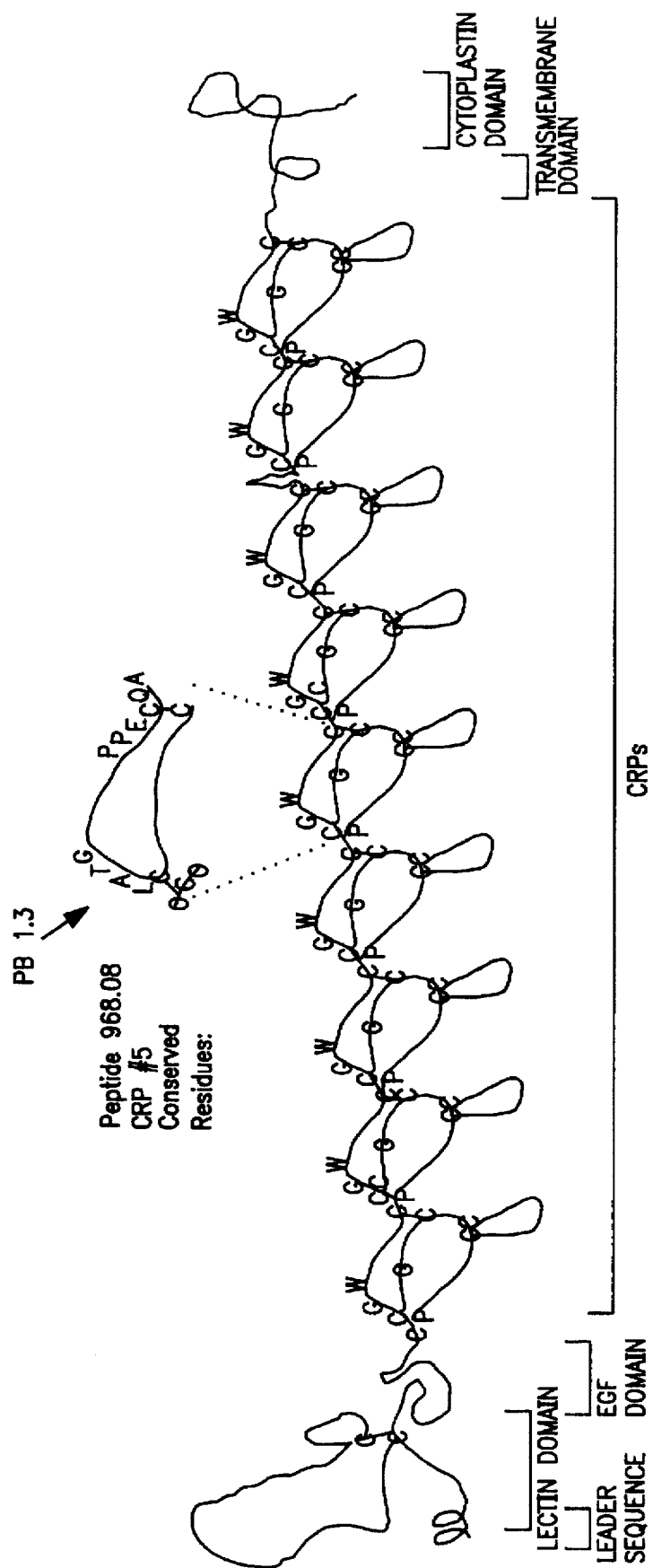

P-selectin is an integral membrane glycoprotein found in secretory granules of platelets and endothelial cells. After cellular activation, P-selectin is rapidly redistributed to the plasma membrane. The mature molecule is a protein with multiple domains, including a "lectin" region, "EGF" region, nine tandem consensus "C3b–C4b Regulatory Protein" (CRP) repeats, a transmembrane region, and a cytoplasmic domain. See Johnston et al., Cell, 56:1033–1044 (1989) (herein incorporated by reference in its entirety for all purposes) for the cloning and description of P-selectin. FIG. 30 shows a proposed folding pattern of the domains of P-selectin.

P-Selectin Deletion Analyses

Figure 31:
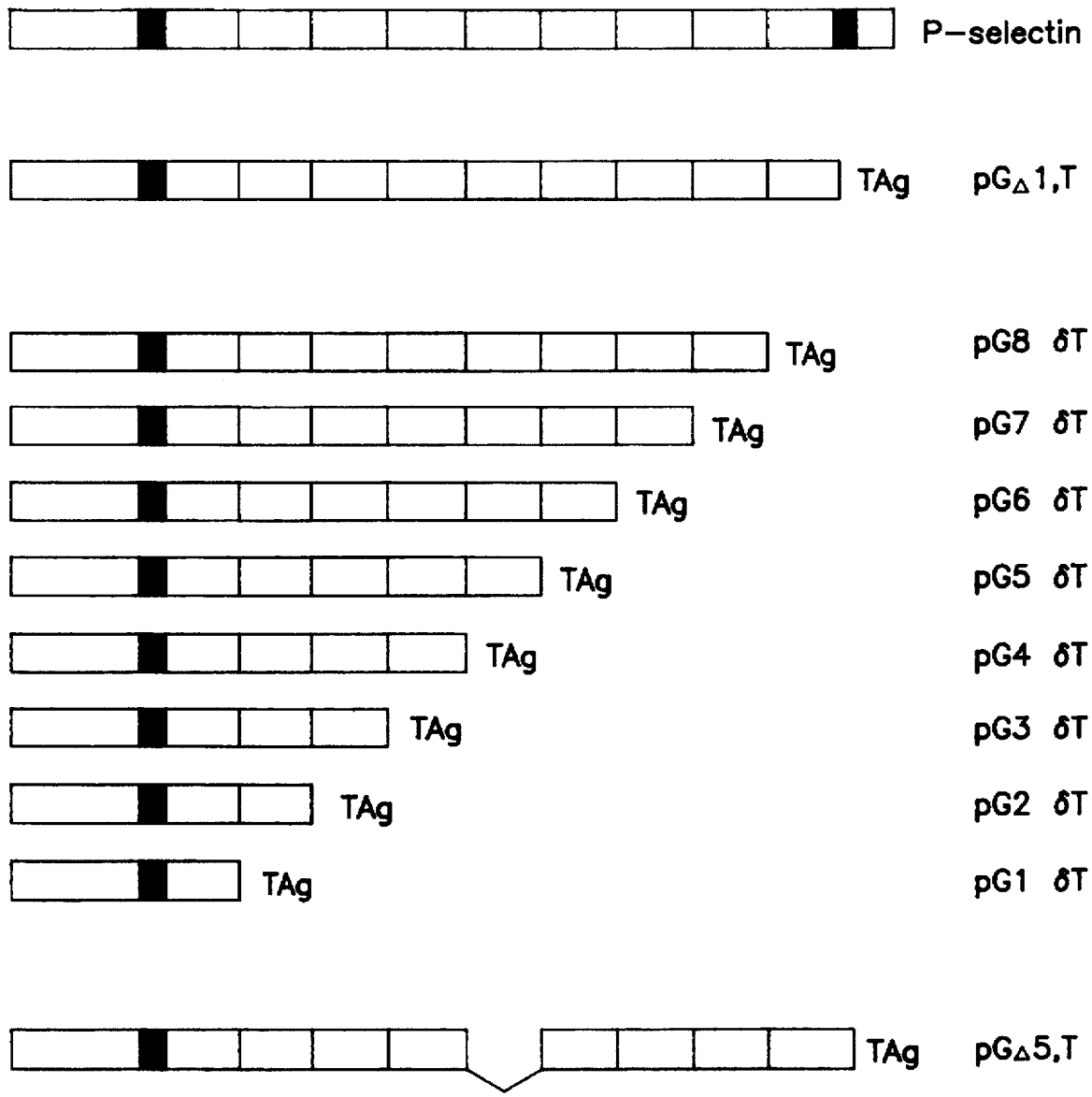

In order to map the epitope specifically bound by mu MAb PB1.3, mutants of recombinant P-selectin were constructed by deleting consecutive CRP domains (FIG. 31). This site-specific mutagenesis was accomplished by PCR amplification using primers specific to each CRP domain (Table 6, SEQ ID Nos. 27–45). The template used for PCR-mutagenesis was a pUC DNA clone of P-selectin which was truncated and mutated at DNA sequence position 2354 (sequence positions are in accordance with the published sequence of P-selectin of Johnston et al., supra. This template plasmid pGΔ1,T which was derived initially by in vitro mutagenesis, lacks the trans-membrane domain and the cytoplasmic carboxy-terminus of P-selectin, and encodes instead the carboxy-terminal 11 amino acid residues of SV40 Large T antigen. This SV40-derived C-terminus is recognized by the monoclonal antibody KT-3. (See MacArthur et al., Journal of Virology 52:483–491 (1984)). After PCR amplification, the deleted DNA molecules were purified, ligated, transformed into bacteria, cloned and sequenced as described below. DNAs with the appropriate linkage of CRP to the T-antigen tag sequence were subcloned into the pcDNA1 expression vector (INVITROGEN) and transfected into COS cells.

PCR mutagenesis was performed on plasmid pGMPΔ1,T. After phosphorylation at the 5'-end, the primers in Table 6 were added to individual PCR reactions at 1 µM, together with the T-antigen sequence primer lys-1. The PCR was performed in a PERKIN ELMER-CETUS machine for 30 cycles at 95° C. for 50 sec, 50° C. for 1 min. and 73° C. for 4 min. using Pfu polymerase (STRATAGENE) according to the manufacturer's recommended conditions. After purification by agarose gel electrophoresis and elution by QIAEX (QIAGEN CORP.), the mutated pUC DNAs were ligated and transformed into E. coli InvF'α cells (INVITROGEN). Cloned DNAs carrying the desired mutation were identified by DNA sequence analysis and the SalI-HpaI fragments containing the mutated P-selectin gene cloned into the XhoI and XbaI sites of the expression vector, pcDNAI (INVITROGEN). The pcDNA clones were transformed into E. coli strain MC1061 (INVITROGEN) and purified plasmid DNAs used for transfection into COS.

DEAE-Dextran Transfection Method

This method is described in Kriegler, M., Gene Transfer and Expression: A Laboratory Manual, W. H. Freeman and Company (1990). COS cells were seeded at 1×10$^6$ cells/100 mm dish in DMEM (BIOWHITTAKER), 10% fetal bovine serum (FBS). On day two, plasmid DNA was ethanol precipitated, and resuspended at a concentration of 20 µg/mL in sterile TE (10 mM Tris, pH 8.0, 1 mM EDTA). 150 µL of DNA was mixed with 300 µl of sterile TBS (Tris Buffered Saline, 140 mM NaCl, 5 mM KCl, 1.4 mM Na$_2$HPO$_4$, 25 mM Tris-base, pH 7.5, 1.0 mM CaCl$_2$, and 0.5 mM MgCl$_2$) and with 300 µl of sterile DEAE dextran (SIGMA, #D-9885, 1 mg/ml in TBS). The growth media was aspirated, and the cell monolayers were washed once with PBS, and once with TBS. 750 µl of the DNA/DEAE dextran/TBS mixture was added to the monolayer. The dish was incubated at ambient temperature inside a laminar flood hood rocking the dish every 5 min for 1 h. After the 1 h incubation, the DNA solution was aspirated and the cells were washed once with TBS and then once with PBS. The cells were incubated in a complete medium supplemented with 100 μM chloroquine (SIGMA, #C-6628), 37° C., 5% $CO_2$. After 4 h, the medium was replaced with complete media, and the cells were incubated at 37° C. and 5% $CO_2$. After 48 h post-transfection, the cells were fed with DMEM growth medium lacking serum. 24 h later the medium was harvested, the cell debris removed by centrifugation at 1500 rpm for 5 min in a tabletop clinical centrifuge.

Capture ELISA to Analyze Secreted P-Selectin Mutant Proteins

Figure 32:
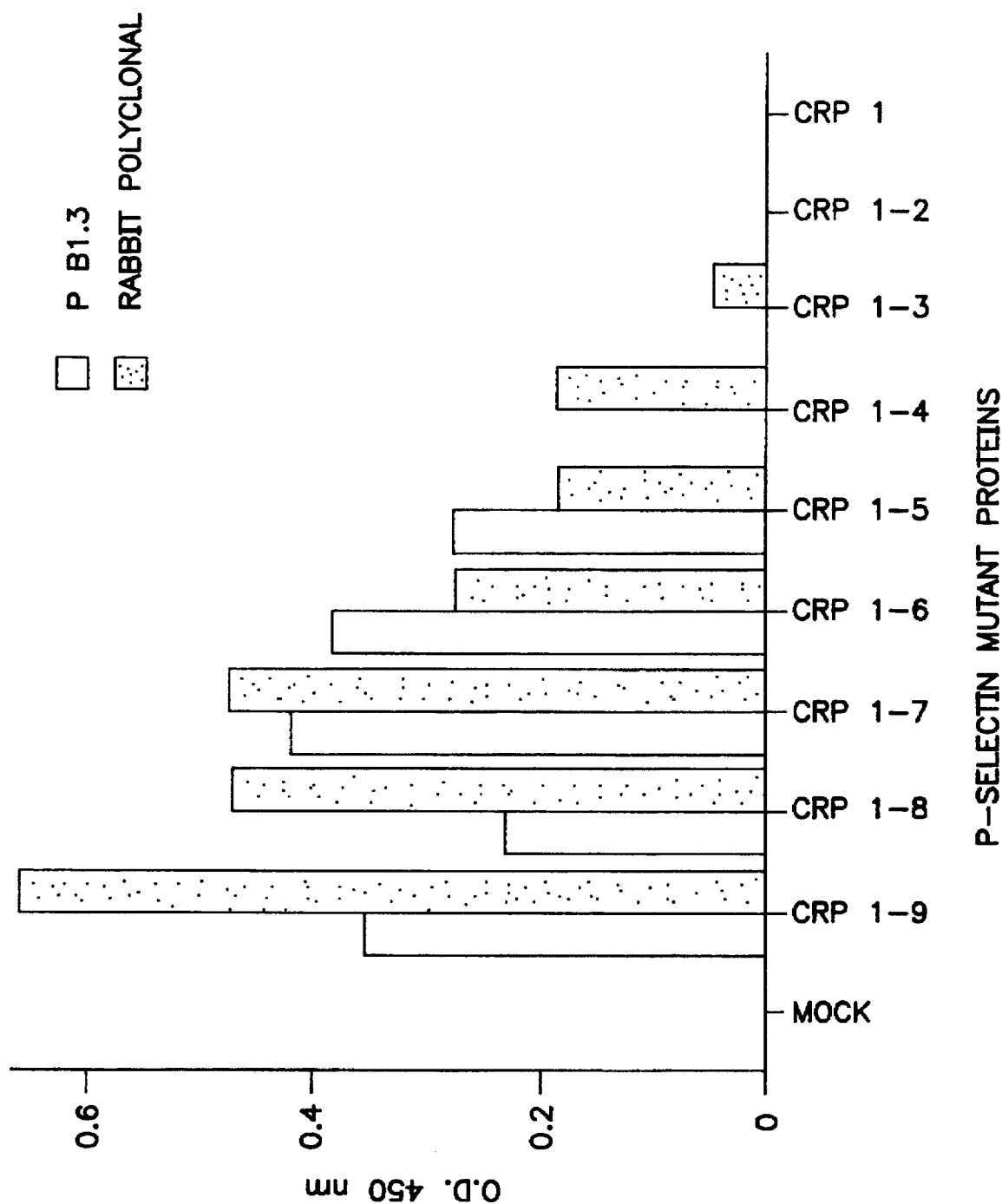

A 96-well COSTAR plate was coated with KT-3 antibody (produced in ascites and purified by Protein G SEPHAROSE, PHARMACIA) 100 μl/well at 40 μg/ml at 4° C. overnight. The plate was washed 3x with DPBS, blocked for 1 h at ambient temperature with 250 μl/well of DPBS+ 1% BSA. The plate was washed 3x with DPBS, and incubated with COS cell supernatants 100 μl/well for 2 h at ambient temperature. After washing the plate 3x with DPBS the bound P-selectin was detected by adding either 100 μl/well of (a) 1 ng/ml rabbit anti-P-selectin polyclonal Ig, or (b) biotinylated mu MAb PB1.3, or (c) biotinylated P6H6 diluted in DPBS/1% BSA for 1 h at ambient temperature. After washing the plate 3x with DPBS the rabbit antibody was detected using 100 μl/well of a 1:1000 dilution of HRP-conjugated goat anti-rabbit antibody (BIORAD), blocked with tissue culture media from the KT-3 cell line (10%) in DPBS/1% BSA for 30 min at ambient temperature. The biotinylated antibodies were detected using 100 μl/well of a 1:1000 dilution of HRP-streptavidin (PIERCE) for 30 min at ambient temperature. The bound HRP was incubated with TMB and quenched with 1M phosphoric acid. FIG. 32 shows the signal less the background from supernatants of mock transfected COS cells. The "Mock" column is the supernatant from cells transfected with a full length form of P-selectin, which lacks the SV40 T-antigen tag, and therefore is not detected in this KT-3 capture ELISA. The X-axis specifies the number of CRPs expressed by the various mutant P-selectin cDNAs, from all 9 CRPs in column 2 to one CRP in column 10. The results show that, although P-selectin mutants lacking the carboxy-terminal 5 CRPs can be detected by the polyclonal rabbit Ig, these molecules do not react with PB1.3. This suggests that the binding site for PB1.3 lies within the fifth CRP repeat domain.

Figure 33:
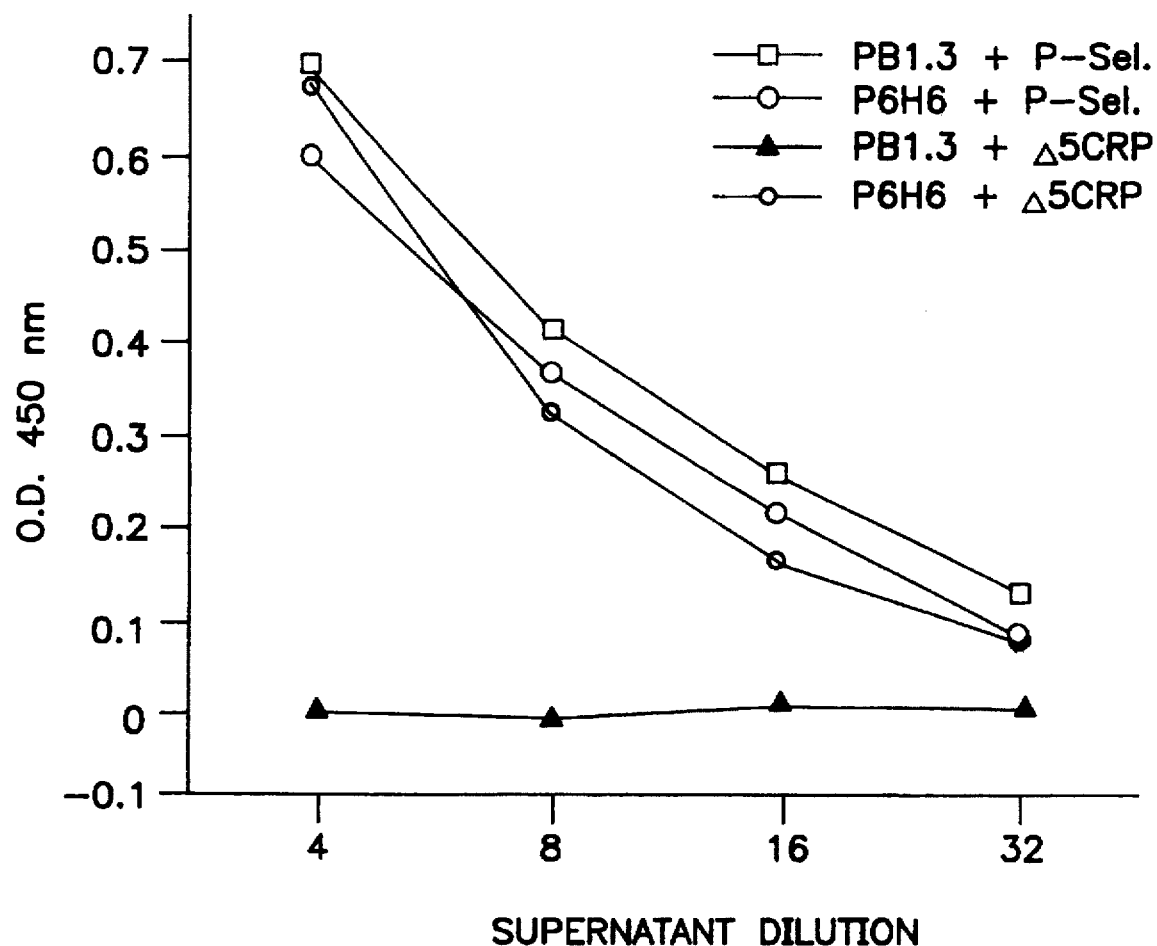

In order to confirm the results from epitope mapping, the deletion analysis was extended to delete only the fifth CRP domain, leaving the carboxy-terminal sequences of P-selectin intact (see FIG. 30). PCR amplimers were designed to remove the region of P-selectin encoding amino acids 407 to 468 (Table 6) using the same protocols described above. Cell supernatants were analyzed directly by ELISA with antibodies Mu MAb PB1.3 and P6H6 (FIG. 33). Although mu MAb PB1.3 binds the intact P-selectin, it fails to bind the deleted molecule. P6H6 binds both molecules equivalently.

Synthetic Peptide Analyses

Figure 34:
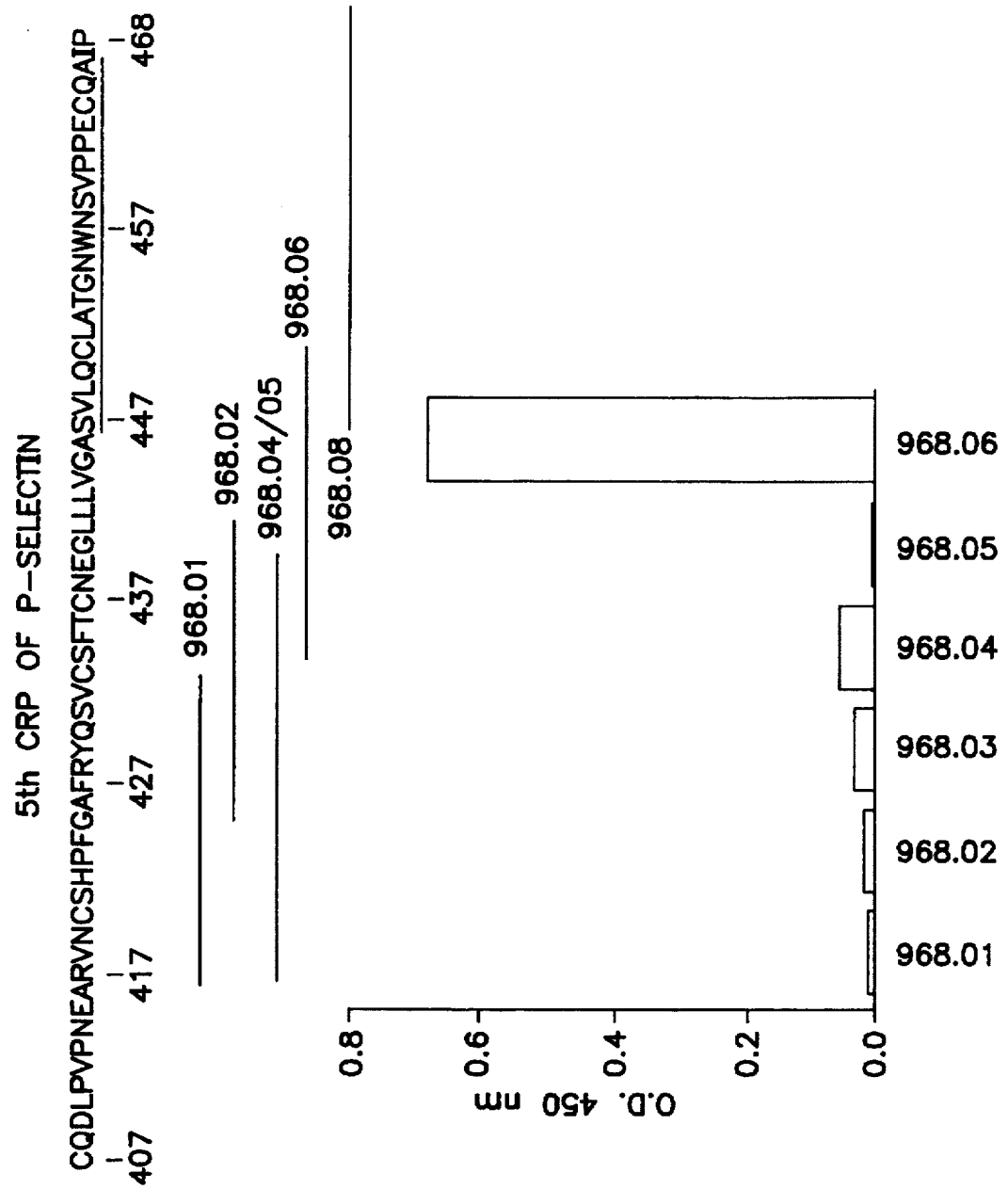

The mu MAb PB1.3 epitope was further characterized by synthesizing peptides spanning the 62 amino acid region of the fifth CRP of P-selectin (FIG. 34) and screening for mu MAb PB1.3 binding by ELISA. The fifth CRP extends from amino acid sequence 407 to 468 according to the nomenclature of Johnston, et al. The peptide sequences are 968.01, a.a. #408–426; 968.02, a.a. #418–436; 968.04, a.a. #408–433; 968.05, an oxidized version of 968.04; 968.06, a.a. #428–447; and 968.08, a.a. #448–467. Each peptide was dissolved to 2 mg/ml in dimethyl sulfoxide (DMSO) and coated onto a 96-well microtiter plated by dilution of 1 microgram into 100 μl PBS and dried at 37° C. overnight. Coated wells were washed with PBS and blocked with 250 μl/well of a solution of PBS/1% BSA for 30 min at ambient temperature. The wells were washed with PBS and incubated with 100 μl/well of PB1.3 diluted to 1 μg/ml in PBS/1%BSA for 1 h at room temperature. Bound mu MAb PB1.3 was detected with HRP-conjugated goat anti-mouse antibody reagent and TMB substrate as described before. FIG. 34 shows a comparison PB1.3 reactivity with the peptides. The carboxy-terminal peptide, number 968.08 reacted strongly with PB1.3. Therefore the epitope recognized by PB1.3 maps to amino acids 448 to 467 in the fifth CRP of human P-selectin.

For the purposes of clarity and understanding, the invention has been described in these examples and the above disclosure in some detail. It will be apparent, however, that certain changes and modifications may be practiced within the scope of the appended claims. All publications and patent applications cited above are hereby incorporated by reference in their entirety for all purposes to the same extent as if each were so individually denoted.

TABLE 1

ALIGNMENT OF AMINO ACID SEQUENCES LEADING TO THE DESIGN OF RESHAPED HUMAN PB1.3 HEAVY CHAIN VARIABLE REGION

| Kabat # | | FR or CDR | mouse 1747 | mouse II A | human I | human 21/28'CL | RH $V_a$* 1747 | Comment |
|---|---|---|---|---|---|---|---|---|
| 1 | 1 | FR1 | E | E | Q | PCA | E | close to H1, possible role in antigen binding |
| 2 | 2 | l | A | V | V | V | A | unusual AA, close to H1, possible role in antigen binding |
| 3 | 3 | l | Q | Q | Q | Q | Q | |
| 4 | 4 | l | L | L | L | L | L | |
| 5 | 5 | l | Q | Q | V | V | V | |
| 6 | 6 | l | Q | Q | Q | Q | Q | |
| 7 | 7 | l | S | S | S | S | S | |
| 8 | 8 | l | G | G | G | G | G | |
| 9 | 9 | l | P | P | A | A | A | |
| 10 | 10 | l | E | E | E | E | E | |
| 11 | 11 | l | L | L | V | V | V | |
| 12 | 12 | l | V | V | K | K | K | |

TABLE 1-continued

ALIGNMENT OF AMINO ACID SEQUENCES LEADING TO THE DESIGN OF RESHAPED HUMAN PB1.3 HEAVY CHAIN VARIABLE REGION

| Kabat | # | FR or CDR | mouse 1747 | mouse II A | human I | human 21/28'CL | RH $V_H$* 1747 | Comment |
|---|---|---|---|---|---|---|---|---|
| 13 | 13 | \| | E | K | K | K | K | |
| 14 | 14 | \| | P | P | P | P | P | |
| 15 | 15 | \| | G | G | G | G | G | |
| 16 | 16 | \| | A | A | A | A | A | |
| 17 | 17 | \| | S | S | S | S | S | |
| 18 | 18 | \| | V | V | V | V | V | |
| 19 | 19 | \| | K | K | K | K | K | |
| 20 | 20 | \| | V | I | V | V | V | |
| 21 | 21 | \| | S | S | S | S | S | |
| 22 | 22 | \| | C | C | C | C | C | |
| 23 | 23 | \| | K | K | K | K | K | |
| 24 | 24 | \| | A | A | A | A | A | |
| 25 | 25 | \| | S | S | S | S | S | |
| 26 | 26 | \| | G | G | G | G | G* | |
| 27 | 27 | \| | Y | Y | Y | Y | Y* | |
| 28 | 28 | \| | T | T | T | T | T* | |
| 29 | 29 | \| | F | F | F | F | F* | |
| 30 | 30 | FRI | T | T | T | T | T* | |
| 31 | 31 | CDR1 | N | D | S | S | N* | |
| 32 | 32 | \| | Y | Y | Y | Y | Y* | |
| 33 | 33 | \| | V | Y | A | A | V | |
| 34 | 34 | \| | M | M | I | M | M* | |
| 35 | 35 | \| | H | N | S | H | H | |
| 35A | | \| | — | — | — | — | — | |
| 35B | | CDR1 | — | — | — | — | — | |
| 36 | 36 | FR2 | W | W | W | W | W | |
| 37 | 37 | \| | V | V | V | V | V | |
| 38 | 38 | \| | K | K | R | R | R | |
| 39 | 39 | \| | Q | Q | Q | Q | Q | |
| 40 | 40 | \| | K | S | A | A | A | |
| 41 | 41 | \| | P | P | P | P | P | |
| 42 | 42 | \| | G | G | G | G | G | |
| 43 | 43 | \| | Q | K | Q | Q | Q | |
| 44 | 44 | \| | G | S | G | R | R | |
| 45 | 45 | \| | L | L | L | L | L | |
| 46 | 46 | \| | E | E | E | E | E | |
| 47 | 47 | \| | W | W | W | W | W | |
| 48 | 48 | \| | I | I | M | M | M | |
| 49 | 49 | FR2 | G | G | G | G | G | |
| 50 | 50 | CDR2 | F | D | W | W | F | |
| 51 | 51 | \| | I | I | I | I | I | |
| 52 | 52 | \| | N | N | N | N | N | |
| 52A | 53 | \| | P | P | P | A | P* | |
| 52B | | \| | — | — | Y | — | — | |
| 52C | | \| | — | — | — | — | — | |
| 53 | 54 | \| | S | G | G | G | S* | |
| 54 | 55 | \| | N | N | N | N | N* | |
| 55 | 56 | \| | D | G | G | G | D* | |
| 56 | 57 | \| | G | G | D | N | G | |
| 57 | 58 | \| | P | T | T | T | P | |
| 58 | 59 | \| | K | S | N | K | K | |
| 59 | 60 | \| | Y | Y | Y | T | Y | |
| 60 | 61 | \| | N | N | A | S | N | |
| 61 | 62 | \| | E | Q | Q | Q | E | |
| 62 | 63 | \| | R | K | K | K | R | |
| 63 | 64 | \| | F | F | F | F | F | |
| 64 | 65 | \| | K | K | Q | Q | K | |
| 65 | 66 | CDR2 | N | G | G | G | N | |
| 66 | 67 | FR3 | K | K | R | R | R | |
| 67 | 68 | \| | A | A | V | V | V | |
| 68 | 69 | \| | T | T | T | T | T | |
| 69 | 70 | \| | L | L | I | I | I | |
| 70 | 71 | \| | T | T | T | T | T | |
| 71 | 72 | \| | S | V | A | R | S* | H2 canonical structure, may be supporting H2 |
| 72 | 73 | \| | D | D | D | D | D | |
| 73 | 74 | \| | K | K | T | T | T | |
| 74 | 75 | \| | S | S | S | S | S | |
| 75 | 76 | \| | S | S | T | A | A | |
| 76 | 77 | \| | S | S | S | S | S | |

TABLE 1-continued

ALIGNMENT OF AMINO ACID SEQUENCES LEADING TO THE DESIGN OF RESHAPED HUMAN PB1.3 HEAVY CHAIN VARIABLE REGION

| Kabat # | | FR or CDR | mouse 1747 | mouse II A | human I | human 21/28'CL | RH $V_n{}^a$ 1747 | Comment |
|---|---|---|---|---|---|---|---|---|
| 77 | 78 | ı | T | T | T | T | T | |
| 78 | 79 | ı | A | A | A | A | A | |
| 79 | 80 | ı | Y | Y | Y | Y | Y | |
| 80 | 81 | ı | M | M | M | M | M | |
| 81 | 82 | ı | E | Q | E | E | E | |
| 82 | 83 | ı | L | L | L | L | L | |
| 82A | 84 | ı | S | S | S | S | S | |
| 82B | 85 | ı | S | S | S | S | S | |
| 82C | 86 | ı | L | L | L | L | L | |
| 83 | 87 | ı | T | T | R | R | R | |
| 84 | 88 | ı | S | S | S | S | S | |
| 85 | 89 | ı | E | E | E | E | E | |
| 86 | 90 | ı | V | D | D | D | D | |
| 87 | 91 | ı | S | S | T | T | T | |
| 88 | 92 | ı | A | A | A | A | A | |
| 89 | 93 | ı | V | V | V | V | V | |
| 90 | 94 | ı | Y | Y | Y | Y | Y | |
| 91 | 95 | ı | F | Y | Y | Y | Y | |
| 92 | 96 | ı | C | C | C | C | C | |
| 93 | 97 | ı | A | A | A | A | A | |
| 94 | 98 | FR3 | R | R | R | R | R* | |
| 95 | 99 | CDR3 | A | G | A | G | A | |
| 96 | 100 | ı | R | X | P | — | R | |
| 97 | 101 | ı | P | Y | G | — | P | |
| 98 | 102 | ı | G | Y | Y | — | G | |
| 99 | 103 | ı | F | S | G | G | F | |
| 100 | 104 | ı | D | S | S | — | D | |
| 100A | | ı | — | S | G | — | — | |
| 100B | | ı | — | Y | G | — | — | |
| 100C | | ı | — | M | G | — | — | |
| 100D | | ı | — | X | C | — | — | |
| 100E | | ı | — | A | Y | — | — | |
| 100F | | ı | — | X | R | Y | — | |
| 100G | | ı | — | X | G | Y | — | |
| 100H | | ı | — | Y | D | G | — | |
| 100I | 105 | ı | W | Y | Y | S | W | |
| 100J | 106 | ı | Y | A | — | G | Y | |
| 100K | 107 | ı | F | F | F | S | F | |
| 101 | 108 | ı | D | D | D | N | D | |
| 102 | 109 | CDR3 | V | Y | Y | Y | V | |
| 103 | 110 | FR4 | W | W | W | W | W | |
| 104 | 111 | ı | G | G | G | G | G | |
| 105 | 112 | ı | A | Q | Q | Q | Q | |
| 106 | 113 | ı | G | G | G | G | G | |
| 107 | 114 | ı | T | T | T | T | T | |
| 108 | 115 | ı | T | T | L | L | L | |
| 109 | 116 | ı | V | V | V | V | V | |
| 110 | 117 | ı | T | T | T | T | T | |
| 111 | 118 | ı | V | V | V | V | V | |
| 112 | 119 | ı | S | S | S | S | S | |
| 113 | 120 | FR4 | S | S | S | S | S | |

TABLE 2

ALIGNMENT OF AMINO ACID SEQUENCES LEADING TO THE DESIGN OF RESHAPED PB1.3 LIGHT CHAIN VARIABLE REGION

| Kabat # | | FR or CDR | mouse 1747 | mouse κV | human κ-I | human DEN | RH $V_L$ 1747 | Comment |
|---|---|---|---|---|---|---|---|---|
| 1 | 1 | FR1 | D | D | D | D | D | |
| 2 | 2 | ı | I | I | I | I | I* | |
| 3 | 3 | ı | V | Q | Q | Q | Q | |
| 4 | 4 | ı | M | M | M | M | M | |
| 5 | 5 | ı | T | T | T | T | T | |
| 6 | 6 | ı | Q | Q | Q | Q | Q | |
| 7 | 7 | ı | S | S | S | S | S | |
| 8 | 8 | ı | Q | P | P | P | P | |
| 9 | 9 | ı | K | S | S | S | S | |
| 10 | 10 | ı | F | S | S | T | T | |

TABLE 2-continued

ALIGNMENT OF AMINO ACID SEQUENCES LEADING TO THE DESIGN OF RESHAPED PB1.3 LIGHT CHAIN VARIABLE REGION

| Kabat | # | FR or CDR | mouse 1747 | mouse κV | human κ-I | human DEN | RH $V_L$ 1747 | Comment |
|---|---|---|---|---|---|---|---|---|
| 11 | 11 | \| | M | L | L | L | L | |
| 12 | 12 | \| | S | S | S | S | S | |
| 13 | 13 | \| | T | A | A | A | A | |
| 14 | 14 | \| | S | S | S | S | S | |
| 15 | 15 | \| | V | L | V | V | V | |
| 16 | 16 | \| | G | G | G | G | G | |
| 17 | 17 | \| | D | D | D | D | D | |
| 18 | 18 | \| | R | R | R | R | R | |
| 19 | 19 | \| | V | V | V | V | V | |
| 20 | 20 | \| | S | T | T | T | T | |
| 21 | 21 | \| | V | I | I | I | V | supporting L1, I may disrupt the core |
| 22 | 22 | \| | T | T | T | T | T | |
| 23 | 23 | FR1 | C | C | C | C | C | |
| 24 | 24 | CDR1 | K | R | R | R | K | |
| 25 | 25 | \| | A | A | A | T | A | |
| 26 | 26 | \| | S | S | S | S | S* | |
| 27 | 27 | \| | Q | Q | Q | Q | Q* | |
| 27A | 28 | \| | N | D | S | S | N | |
| 27B | | \| | — | — | L | — | — | |
| 27C | | \| | — | — | V | — | — | |
| 27D | | \| | — | — | — | — | — | |
| 27E | | \| | — | — | — | — | — | |
| 27F | | \| | — | — | — | — | — | |
| 28 | 29 | \| | V | D | S | I | V* | |
| 29 | 30 | \| | A | I | I | S | A* | |
| 30 | 31 | \| | T | S | S | R | T* | |
| 31 | 32 | \| | N | N | N/S | W | N* | |
| 32 | 33 | \| | V | Y | Y | L | V* | |
| 33 | 34 | \| | V | L | L | A | V* | |
| 34 | | CDR1 | — | N | A | — | — | |
| 35 | 35 | FR2 | W | W | W | W | W | |
| 36 | 36 | \| | Y | Y | Y | Y | Y | |
| 37 | 37 | \| | Q | Q | Q | Q | Q | |
| 38 | 38 | \| | Q | Q | Q | Q | Q | |
| 39 | 39 | \| | R | K | K | K | K | |
| 40 | 40 | \| | P | P | P | P | P | |
| 41 | 41 | \| | G | G | G | G | G | |
| 42 | 42 | \| | Q | Q | K | E | E | |
| 43 | 43 | \| | S | S | A | A | A | |
| 44 | 44 | \| | P | P | P | P | P | |
| 45 | 45 | \| | K | K | K | K | K | |
| 46 | 46 | \| | A | L | L | L | A | may be supporting L2, L may alter the orientation of L2 |
| 47 | 47 | \| | L | L | L | L | L | |
| 48 | 48 | \| | I | I | I | I | I* | |
| 49 | 49 | FR2 | Y | Y | Y | Y | Y | |
| 50 | 50 | CDR2 | T | Y | A | G | T* | |
| 51 | 51 | \| | A | A | A | A | A* | |
| 52 | 52 | \| | S | S | S | S | S* | |
| 53 | 53 | \| | Y | R | S | N | Y | |
| 54 | 54 | \| | R | L | L | L | R | |
| 55 | 55 | \| | F | H | E | E | F | |
| 56 | 56 | CDR2 | S | S | S | S | S | |
| 57 | 57 | FR3 | G | G | G | G | G | |
| 58 | 58 | \| | V | V | V | V | V | |
| 59 | 59 | \| | P | P | P | P | P | |
| 60 | 60 | \| | E | S | S | S | E | close to residue 54 in L2, on the surface and may bind Ag |
| 61 | 61 | \| | R | R | R | R | R | |
| 62 | 62 | \| | F | F | F | F | F | |
| 63 | 63 | \| | S | S | S | S | S | |
| 64 | 64 | \| | G | G | G | G | G* | |
| 65 | 65 | \| | S | S | S | S | S | |

TABLE 2-continued

ALIGNMENT OF AMINO ACID SEQUENCES LEADING TO THE DESIGN OF
RESHAPED PB1.3 LIGHT CHAIN VARIABLE REGION

| Kabat # | # | FR or CDR | mouse 1747 | mouse κV | human κ-I | human DEN | RH $V_L$ 1747 | Comment |
|---|---|---|---|---|---|---|---|---|
| 66 | 66 | I | G | G | G | G | G | |
| 67 | 67 | I | S | S | S | S | S | |
| 68 | 68 | I | G | G | G | G | G | |
| 69 | 69 | I | T | T | T | T | T | |
| 70 | 70 | I | D | D | D | E | D | may have charge interaction with residue 24 in L1. |
| 71 | 71 | I | F | Y | F | F | F* | |
| 72 | 72 | I | T | S | T | T | T | |
| 73 | 73 | I | L | L | L | L | L | |
| 74 | 74 | I | T | T | T | T | T | |
| 75 | 75 | I | I | I | I | I | I | |
| 76 | 76 | I | T | S | S | S | S | |
| 77 | 77 | I | N | N | S | S | S | |
| 78 | 78 | I | V | L | L | L | L | |
| 79 | 79 | I | Q | E | Q | Q | Q | |
| 80 | 80 | I | S | Q | P | S | S | |
| 81 | 81 | I | E | E | E | D | D | |
| 82 | 82 | I | D | D | D | D | D | |
| 83 | 83 | I | L | I | F | F | F | |
| 84 | 84 | I | A | A | A | A | A | |
| 85 | 85 | I | D | T | T | T | T | |
| 86 | 86 | I | Y | Y | Y | Y | Y | |
| 87 | 87 | I | F | F | Y | Y | Y | |
| 88 | 88 | FR3 | C | C | C | C | C | |
| 89 | 89 | CDR3 | Q | Q | Q | Q | Q | |
| 90 | 90 | I | Q | Q | Q | Q | Q* | |
| 91 | 91 | I | Y | G | Y | Y | Y* | |
| 92 | 92 | I | N | N | N | DN | N* | |
| 93 | 93 | I | N | T | S | S | N* | |
| 94 | 94 | I | Y | L | L | F | Y* | |
| 95 | 95 | I | P | P | P | P | P* | |
| 95A | | I | — | — | E | — | — | |
| 95B | | I | — | — | — | — | — | |
| 95C | | I | — | — | — | — | — | |
| 95D | | I | — | — | — | — | — | |
| 95E | | I | — | — | — | — | — | |
| 95F | | I | — | — | I | — | — | |
| 96 | 96 | I | Y | R | W | Y | Y* | |
| 97 | 97 | CDR3 | T | T | T | T | T | |
| 98 | 98 | FR4 | F | F | F | F | F | |
| 99 | 99 | I | G | G | G | G | G | |
| 100 | 100 | I | G | G | Q | Q | Q | |
| 101 | 101 | I | G | G | G | G | G | |
| 102 | 102 | I | T | T | T | T | T | |
| 103 | 103 | I | K | K | K | K | K | |
| 104 | 104 | I | V | L | V | L | L | |
| 105 | 105 | I | E | E | E | E | E | |
| 106 | 106 | I | I | I | I | I | I | |
| 106A | | I | — | — | — | — | — | |
| 107 | 107 | FR4 | Q | K | K | K | K | |

TABLE 3

DIFFERENCES IN AMINO ACID SEQUENCES FOR THE
HEAVY CHAIN VARIABLE DOMAINS FOR THE
THREE RESHAPED VERSIONS OF PB1.3

| | AMINO ACID | | |
|---|---|---|---|
| CONSTRUCT | 1 | 2 | 73 |
| 1748R

TABLE 5

ANTIBODY PRODUCTION RATES FOR AMPLIFIED CHO CELL LINES PRODUCING THREE DIFFERENT VERSIONS OF HUMANIZED PB1.3 (CY1748)
(micrograms/10⁶ cells/day)

| Antibody | Unamplified | 1st round | 2nd round | 3rd round |
|---|---|---|---|---|
| 1748A-IgG1 | 0.36 | 2.1 | 8.2 | 29.6 |
|  | 0.36 | 2.1 | 13.7 | 21.8 |
|  | 0.36 | 0.90 | 9.9 | 19.7 |
| 1748B-IgG1 | 0.10 | 1.6 | 23.9 |  |
|  | 0.24 | 1.5 | 21.1 |  |
|  | <0.2 | 7.3 | 18.6 |  |
|  | 0.10 | 1.6 | 17.8 |  |
| 1748B-IgG4 | <0.3 | <2.0 | 33.0 |  |
|  | <0.3 | <2.0 | 26.9 |  |
|  | 0.75 | 2.6 | 23.2 |  |
|  | <0.3 | 3.0 | 20.8 |  |
|  | 0.80 | 6.5 | 20.8 |  |
|  | <0.3 | <2.0 | 19.4 |  |
|  | 0.78 | 2.5 | 18.6 |  |
|  | 0.78 | 8.8 | 17.8 |  |

TABLE 6

DNA SEQUENCE OF THE PCR AMPLIMERS USED TO GENERATE HUMAN P-SELECTIN CRP DELETION MUTANTS

| PCR 3'-amplimer to remove CRP Number: |  | Predicted amino acid sequence of mutant | |
|---|---|---|---|
|  |  | CRP⁻ | TAg |
| 9 | 5'-TTTCACAGCTCTGCATGC-3' | ...CRAVK | TIQEA LK... |
| 8-9 | 5'-TGCTATGCCTTTGCAGGT-3' | ...CKGIA | TIQEA LK... |
| 7-9 | 5'-CTTGATGGCTTCACACAT-3' | ...CEAIK | TIQEA LK... |
| 6-9 | 5'-GGGAATGGCTTGGCATTC-3' | ...CQAIP | TIQEA LK... |
| 5-9 | 5'-CTGCAAAGCTTGACAGAC-3' | ...CQALQ | TIQEA LK... |
| 4-9 | 5'-CGAAATAGCCTCACAGGT-3' | ...CEAIS | TIQEA LK... |
| 3-9 | 5'-CTGCACAGCTTTACACAC-3' | ...VKAVQ | TIQEA LK... |
| 2-9 | 5'-CTGGGCAGCTAAACACTG-3' | ...CLAAQ | TIQEA LK... |
| 5'-amplimer, lys-1 | 5'-AAACCTCCCACACCCCCT-3' |  |  |
| To Delete only CRP#5 these two amplimers were used: |  |  |  |
| 5'-amplimer | 5'-TGCACACCTTTGCTAAGC-3' |  |  |
| 3'-amplimer | 5'-CTGCAAAGCTTGACAGAC-3' |  |  |

---

SEQUENCE LISTING ( 1 ) GENERAL INFORMATION:

( i i i ) NUMBER OF SEQUENCES: 45

( 2 ) INFORMATION FOR SEQ ID NO:1:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

```
Cys Gln Asn Arg Tyr Thr Asp Leu Val Ala Ile Gln Asn Lys Asn Glu
 1               5                  10                  15
```

( 2 ) INFORMATION FOR SEQ ID NO:2:

( i ) SEQUENCE CHARACTERISTICS:
        ( A ) LENGTH: 417 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..417

( i x ) FEATURE:
        ( A ) NAME/KEY: misc_feature
        ( B ) LOCATION: 1..417
        ( D ) OTHER INFORMATION: /note= "Sequence encoding
                CY1747(PB1.3) Heavy Chain Signal Peptide and
                Variable Region"

( x i ) SEQUENCE DESCRIPTION: SEQ ID NO:2:

```
ATG GGA TGG AGC GGG GTC TTT CTC TTT CTC CTG TCA GGA ACT GCA GGT     48
Met Gly Trp Ser Gly Val Phe Leu Phe Leu Leu Ser Gly Thr Ala Gly
 1               5                  10                  15

GTC CAC TCT GAG GCC CAG CTG CAG CAG TCT GGA CCT GAG CTG GTA GAG     96
Val His Ser Glu Ala Gln Leu Gln Gln Ser Gly Pro Glu Leu Val Glu
             20                  25                  30

CCT GGG GCT TCA GTG AAG GTG TCC TGC AAG GCT TCT GGA TAC ACA TTC    144
Pro Gly Ala Ser Val Lys Val Ser Cys Lys Ala Ser Gly Tyr Thr Phe
         35                  40                  45

ACC AAC TAT GTT ATG CAC TGG GTG AAG CAG AAG CCT GGG CAG GGC CTT    192
Thr Asn Tyr Val Met His Trp Val Lys Gln Lys Pro Gly Gln Gly Leu
     50                  55                  60

GAG TGG ATT GGA TTT ATT AAC CCA TCC AAT GAT GGT CCT AAG TAC AAT    240
Glu Trp Ile Gly Phe Ile Asn Pro Ser Asn Asp Gly Pro Lys Tyr Asn
 65                  70                  75                  80

GAG AGG TTC AAA AAC AAG GCC ACA CTG ACT TCA GAC AAA TCC TCC AGC    288
Glu Arg Phe Lys Asn Lys Ala Thr Leu Thr Ser Asp Lys Ser Ser Ser
                 85                  90                  95

ACA GCC TAC ATG GAG CTC AGC AGC CTG ACC TCT GAG GTC TCT GCG GTC    336
Thr Ala Tyr Met Glu Leu Ser Ser Leu Thr Ser Glu Val Ser Ala Val
            100                 105                 110

TAT TTC TGT GCA AGA GCC CGC CCG GGG TTC GAC TGG TAC TTC GAT GTC    384
Tyr Phe Cys Ala Arg Ala Arg Pro Gly Phe Asp Trp Tyr Phe Asp Val
        115                 120                 125

TGG GGC GCA GGG ACC ACG GTC ACC GTC TCC TCA                        417
Trp Gly Ala Gly Thr Thr Val Thr Val Ser Ser
    130                 135
```

( 2 ) INFORMATION FOR SEQ ID NO:3:

( i ) SEQUENCE CHARACTERISTICS:
        ( A ) LENGTH: 139 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met Gly Trp Ser Gly Val Phe Leu Phe Leu Leu Ser Gly Thr Ala Gly
 1               5                  10                  15

Val His Ser Glu Ala Gln Leu Gln Gln Ser Gly Pro Glu Leu Val Glu
             20                  25                  30

Pro Gly Ala Ser Val Lys Val Ser Cys Lys Ala Ser Gly Tyr Thr Phe
```

|   |   |   |   |   | 35 |   |   |   |   | 40 |   |   |   |   | 45 |   |
|---|---|---|---|---|---|---|---|---|---|---|---|---|---|---|---|---|

Thr Asn Tyr Val Met His Trp Val Lys Gln Lys Pro Gly Gln Gly Leu
      50                 55                60

Glu Trp Ile Gly Phe Ile Asn Pro Ser Asn Asp Gly Pro Lys Tyr Asn
65               70               75              80

Glu Arg Phe Lys Asn Lys Ala Thr Leu Thr Ser Asp Lys Ser Ser Ser
            85               90              95

Thr Ala Tyr Met Glu Leu Ser Ser Leu Thr Ser Glu Val Ser Ala Val
         100             105           110

Tyr Phe Cys Ala Arg Ala Arg Pro Gly Phe Asp Trp Tyr Phe Asp Val
      115             120           125

Trp Gly Ala Gly Thr Thr Val Thr Val Ser Ser
   130            135

( 2 ) INFORMATION FOR SEQ ID NO:4:

( i ) SEQUENCE CHARACTERISTICS:
        ( A ) LENGTH: 393 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..393

( i x ) FEATURE:
        ( A ) NAME/KEY: misc_feature
        ( B ) LOCATION: 1..393
        ( D ) OTHER INFORMATION: /note= "Sequence encoding
            CY1747(PB1.3) Light Chain Signal Peptide and
            Variable Region"

( x i ) SEQUENCE DESCRIPTION: SEQ ID NO:4:

ATG GGC ATC AAG ATG GAG TCA CAG ATT CAG GTC TTT GTA TAC ATG TTG    48
Met Gly Ile Lys Met Glu Ser Gln Ile Gln Val Phe Val Tyr Met Leu
 1             5               10              15

CTG TGG TTG TCT GGT GTT GAT GGA GAC ATT GTG ATG ACC CAG TCT CAA    96
Leu Trp Leu Ser Gly Val Asp Gly Asp Ile Val Met Thr Gln Ser Gln
          20               25              30

AAA TTC ATG TCC ACA TCA GTA GGA GAC AGG GTC AGC GTC ACC TGC AAG  144
Lys Phe Met Ser Thr Ser Val Gly Asp Arg Val Ser Val Thr Cys Lys
      35               40             45

GCC AGT CAG AAT GTG GCT ACT AAT GTA GTC TGG TAT CAA CAG AGA CCA  192
Ala Ser Gln Asn Val Ala Thr Asn Val Val Trp Tyr Gln Gln Arg Pro
     50              55             60

GGA CAA TCT CCT AAA GCG CTT ATT TAT ACG GCA TCC TAC CGG TTC AGT  240
Gly Gln Ser Pro Lys Ala Leu Ile Tyr Thr Ala Ser Tyr Arg Phe Ser
65              70             75             80

GGA GTC CCT GAA CGC TTC TCA GGC AGT GGA TCT GGG ACA GAT TTC ACT  288
Gly Val Pro Glu Arg Phe Ser Gly Ser Gly Ser Gly Thr Asp Phe Thr
            85              90           95

CTC ACC ATC ACC AAT GTG CAG TCT GAA GAC TTG GCA GAC TAT TTC TGT  336
Leu Thr Ile Thr Asn Val Gln Ser Glu Asp Leu Ala Asp Tyr Phe Cys
        100            105           110

CAA CAA TAT AAC AAC TAT CCC TAC ACG TTC GGA GGG GGG ACC AAG GTG  384
Gln Gln Tyr Asn Asn Tyr Pro Tyr Thr Phe Gly Gly Gly Thr Lys Val
     115              120           125

GAA ATT CAA  393
Glu Ile Gln
 130

( 2 ) INFORMATION FOR SEQ ID NO:5:

( i ) SEQUENCE CHARACTERISTICS:
        ( A ) LENGTH: 131 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Gly Ile Lys Met Glu Ser Gln Ile Gln Val Phe Val Tyr Met Leu
 1               5                  10                  15
Leu Trp Leu Ser Gly Val Asp Gly Asp Ile Val Met Thr Gln Ser Gln
                20                  25                  30
Lys Phe Met Ser Thr Ser Val Gly Asp Arg Val Ser Val Thr Cys Lys
                35                  40                  45
Ala Ser Gln Asn Val Ala Thr Asn Val Val Trp Tyr Gln Gln Arg Pro
        50                  55                  60
Gly Gln Ser Pro Lys Ala Leu Ile Tyr Thr Ala Ser Tyr Arg Phe Ser
 65                 70                  75                  80
Gly Val Pro Glu Arg Phe Ser Gly Ser Gly Ser Gly Thr Asp Phe Thr
                85                  90                  95
Leu Thr Ile Thr Asn Val Gln Ser Glu Asp Leu Ala Asp Tyr Phe Cys
                100                 105                 110
Gln Gln Tyr Asn Asn Tyr Pro Tyr Thr Phe Gly Gly Gly Thr Lys Val
                115                 120                 125
Glu Ile Gln
    130
```

( 2 ) INFORMATION FOR SEQ ID NO:6:

( i ) SEQUENCE CHARACTERISTICS:
        ( A ) LENGTH: 417 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..417

( i x ) FEATURE:
        ( A ) NAME/KEY: misc_feature
        ( B ) LOCATION: 1..417
        ( D ) OTHER INFORMATION: /note= "Sequence encoding CY1748
        ( P B 1 . 3 - H u m a n i z e d ) Heavy Chain-A Signal Peptide and
        Variable Region"

( x i ) SEQUENCE DESCRIPTION: SEQ ID NO:6:

```
ATG GAG TTT GGG CTG AGC TGG CTT TTT CTT GTG GCT ATT TTA AAA GGT        48
Met Glu Phe Gly Leu Ser Trp Leu Phe Leu Val Ala Ile Leu Lys Gly
 1               5                  10                  15

GTC CAG TGT GAG GCC CAG CTG GTG CAG TCT GGA GCT GAG GTG AAA AAG        96
Val Gln Cys Glu Ala Gln Leu Val Gln Ser Gly Ala Glu Val Lys Lys
                20                  25                  30

CCT GGG GCT TCA GTG AAG GTG TCC TGC AAG GCT TCT GGA TAC ACA TTC       144
Pro Gly Ala Ser Val Lys Val Ser Cys Lys Ala Ser Gly Tyr Thr Phe
                35                  40                  45

ACC AAC TAT GTT ATG CAC TGG GTG CGC CAA GCT CCC GGG CAG AGG CTT       192
Thr Asn Tyr Val Met His Trp Val Arg Gln Ala Pro Gly Gln Arg Leu
        50                  55                  60

GAG TGG ATG GGA TTT ATT AAC CCA TCC AAT GAT GGT CCT AAG TAC AAT       240
```

|  |  |  |  |  |  |  |  |  |  |  |  |  |  |  |  |
|---|---|---|---|---|---|---|---|---|---|---|---|---|---|---|---|
| Glu | Trp | Met | Gly | Phe | Ile | Asn | Pro | Ser | Asn | Asp | Gly | Pro | Lys | Tyr | Asn |
| 65 |  |  |  |  | 70 |  |  |  | 75 |  |  |  |  |  | 80 |

| GAG | AGG | TTC | AAA | AAC | AGG | GTC | ACA | ATC | ACT | TCA | GAC | ACA | TCC | GCC | AGC | 288 |
|---|---|---|---|---|---|---|---|---|---|---|---|---|---|---|---|---|
| Glu | Arg | Phe | Lys | Asn | Arg | Val | Thr | Ile | Thr | Ser | Asp | Thr | Ser | Ala | Ser |  |
|  |  |  |  | 85 |  |  |  |  | 90 |  |  |  |  | 95 |  |  |

| ACC | GCC | TAC | ATG | GAA | CTG | TCC | AGC | CTG | CGC | TCC | GAG | GAC | ACT | GCA | GTC | 336 |
|---|---|---|---|---|---|---|---|---|---|---|---|---|---|---|---|---|
| Thr | Ala | Tyr | Met | Glu | Leu | Ser | Ser | Leu | Arg | Ser | Glu | Asp | Thr | Ala | Val |  |
|  |  |  | 100 |  |  |  |  | 105 |  |  |  |  | 110 |  |  |  |

| TAT | TAC | TGT | GCC | AGA | GCA | CGC | CCG | GGG | TTC | GAC | TGG | TAC | TTC | GAT | GTC | 384 |
|---|---|---|---|---|---|---|---|---|---|---|---|---|---|---|---|---|
| Tyr | Tyr | Cys | Ala | Arg | Ala | Arg | Pro | Gly | Phe | Asp | Trp | Tyr | Phe | Asp | Val |  |
|  |  | 115 |  |  |  |  | 120 |  |  |  |  | 125 |  |  |  |  |

| TGG | GGA | CAG | GGT | ACC | CTT | GTC | ACC | GTC | AGT | TCA | 417 |
|---|---|---|---|---|---|---|---|---|---|---|---|
| Trp | Gly | Gln | Gly | Thr | Leu | Val | Thr | Val | Ser | Ser |  |
| 130 |  |  |  |  | 135 |  |  |  |  |  |  |

( 2 ) INFORMATION FOR SEQ ID NO:7:

( i ) SEQUENCE CHARACTERISTICS:
        ( A ) LENGTH: 139 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

| Met | Glu | Phe | Gly | Leu | Ser | Trp | Leu | Phe | Leu | Val | Ala | Ile | Leu | Lys | Gly |
|---|---|---|---|---|---|---|---|---|---|---|---|---|---|---|---|
| 1 |  |  |  | 5 |  |  |  |  | 10 |  |  |  |  | 15 |  |

| Val | Gln | Cys | Glu | Ala | Gln | Leu | Val | Gln | Ser | Gly | Ala | Glu | Val | Lys | Lys |
|---|---|---|---|---|---|---|---|---|---|---|---|---|---|---|---|
|  |  |  | 20 |  |  |  |  | 25 |  |  |  |  | 30 |  |  |

| Pro | Gly | Ala | Ser | Val | Lys | Val | Ser | Cys | Lys | Ala | Ser | Gly | Tyr | Thr | Phe |
|---|---|---|---|---|---|---|---|---|---|---|---|---|---|---|---|
|  |  |  | 35 |  |  |  |  | 40 |  |  |  |  | 45 |  |  |

| Thr | Asn | Tyr | Val | Met | His | Trp | Val | Arg | Gln | Ala | Pro | Gly | Gln | Arg | Leu |
|---|---|---|---|---|---|---|---|---|---|---|---|---|---|---|---|
|  | 50 |  |  |  |  | 55 |  |  |  |  | 60 |  |  |  |  |

| Glu | Trp | Met | Gly | Phe | Ile | Asn | Pro | Ser | Asn | Asp | Gly | Pro | Lys | Tyr | Asn |
|---|---|---|---|---|---|---|---|---|---|---|---|---|---|---|---|
| 65 |  |  |  |  | 70 |  |  |  | 75 |  |  |  |  |  | 80 |

| Glu | Arg | Phe | Lys | Asn | Arg | Val | Thr | Ile | Thr | Ser | Asp | Thr | Ser | Ala | Ser |
|---|---|---|---|---|---|---|---|---|---|---|---|---|---|---|---|
|  |  |  |  | 85 |  |  |  |  | 90 |  |  |  |  | 95 |  |

| Thr | Ala | Tyr | Met | Glu | Leu | Ser | Ser | Leu | Arg | Ser | Glu | Asp | Thr | Ala | Val |
|---|---|---|---|---|---|---|---|---|---|---|---|---|---|---|---|
|  |  |  | 100 |  |  |  |  | 105 |  |  |  |  | 110 |  |  |

| Tyr | Tyr | Cys | Ala | Arg | Ala | Arg | Pro | Gly | Phe | Asp | Trp | Tyr | Phe | Asp | Val |
|---|---|---|---|---|---|---|---|---|---|---|---|---|---|---|---|
|  |  | 115 |  |  |  |  | 120 |  |  |  |  | 125 |  |  |  |

| Trp | Gly | Gln | Gly | Thr | Leu | Val | Thr | Val | Ser | Ser |
|---|---|---|---|---|---|---|---|---|---|---|
| 130 |  |  |  |  | 135 |  |  |  |  |  |

( 2 ) INFORMATION FOR SEQ ID NO:8:

( i ) SEQUENCE CHARACTERISTICS:
        ( A ) LENGTH: 417 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..417

( i x ) FEATURE:
        ( A ) NAME/KEY: misc_feature
        ( B ) LOCATION: 1..417
        ( D ) OTHER INFORMATION: /note= "Sequence encoding CY1748
        (PB1.3-Humanized) Heavy Chain-B Signal Peptide and
        Variable Region"

( x i ) SEQUENCE DESCRIPTION: SEQ ID NO:8:

| | | | | | | | | | | | | | | | | |
|---|---|---|---|---|---|---|---|---|---|---|---|---|---|---|---|---|
| ATG | GAG | TTT | GGG | CTG | AGC | TGG | CTT | TTT | CTT | GTG | GCT | ATT | TTA | AAA | GGT | 48 |
| Met | Glu | Phe | Gly | Leu | Ser | Trp | Leu | Phe | Leu | Val | Ala | Ile | Leu | Lys | Gly | |
| 1 | | | | 5 | | | | | 10 | | | | | 15 | | |
| GTC | CAG | TGT | CAG | GTC | CAG | CTG | GTG | CAG | TCT | GGA | GCT | GAG | GTG | AAA | AAG | 96 |
| Val | Gln | Cys | Gln | Val | Gln | Leu | Val | Gln | Ser | Gly | Ala | Glu | Val | Lys | Lys | |
| | | | 20 | | | | | 25 | | | | | 30 | | | |
| CCT | GGG | GCT | TCA | GTG | AAG | GTG | TCC | TGC | AAG | GCT | TCT | GGA | TAC | ACA | TTC | 144 |
| Pro | Gly | Ala | Ser | Val | Lys | Val | Ser | Cys | Lys | Ala | Ser | Gly | Tyr | Thr | Phe | |
| | | 35 | | | | | 40 | | | | | 45 | | | | |
| ACC | AAC | TAT | GTT | ATG | CAC | TGG | GTG | CGC | CAA | GCT | CCC | GGG | CAG | AGG | CTT | 192 |
| Thr | Asn | Tyr | Val | Met | His | Trp | Val | Arg | Gln | Ala | Pro | Gly | Gln | Arg | Leu | |
| | 50 | | | | | 55 | | | | | 60 | | | | | |
| GAG | TGG | ATG | GGA | TTT | ATT | AAC | CCA | TCC | AAT | GAT | GGT | CCT | AAG | TAC | AAT | 240 |
| Glu | Trp | Met | Gly | Phe | Ile | Asn | Pro | Ser | Asn | Asp | Gly | Pro | Lys | Tyr | Asn | |
| 65 | | | | | 70 | | | | | 75 | | | | | 80 | |
| GAG | AGG | TTC | AAA | AAC | AGG | GTC | ACA | ATC | ACT | TCA | GAC | ACA | TCC | GCC | AGC | 288 |
| Glu | Arg | Phe | Lys | Asn | Arg | Val | Thr | Ile | Thr | Ser | Asp | Thr | Ser | Ala | Ser | |
| | | | | 85 | | | | | 90 | | | | | 95 | | |
| ACC | GCC | TAC | ATG | GAA | CTG | TCC | AGC | CTG | CGC | TCC | GAG | GAC | ACT | GCA | GTC | 336 |
| Thr | Ala | Tyr | Met | Glu | Leu | Ser | Ser | Leu | Arg | Ser | Glu | Asp | Thr | Ala | Val | |
| | | | 100 | | | | | 105 | | | | | 110 | | | |
| TAT | TAC | TGT | GCC | AGA | GCA | CGC | CCG | GGG | TTC | GAC | TGG | TAC | TTC | GAT | GTC | 384 |
| Tyr | Tyr | Cys | Ala | Arg | Ala | Arg | Pro | Gly | Phe | Asp | Trp | Tyr | Phe | Asp | Val | |
| | | 115 | | | | | 120 | | | | | 125 | | | | |
| TGG | GGA | CAG | GGT | ACC | CTT | GTC | ACC | GTC | AGT | TCA | | | | | | 417 |
| Trp | Gly | Gln | Gly | Thr | Leu | Val | Thr | Val | Ser | Ser | | | | | | |
| 130 | | | | | 135 | | | | | | | | | | | |

( 2 ) INFORMATION FOR SEQ ID NO:9:

( i ) SEQUENCE CHARACTERISTICS:
        ( A ) LENGTH: 139 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| | | | | | | | | | | | | | | |
|---|---|---|---|---|---|---|---|---|---|---|---|---|---|---|
| Met | Glu | Phe | Gly | Leu | Ser | Trp | Leu | Phe | Leu | Val | Ala | Ile | Leu | Lys | Gly |
| 1 | | | | 5 | | | | | 10 | | | | | 15 | |
| Val | Gln | Cys | Gln | Val | Gln | Leu | Val | Gln | Ser | Gly | Ala | Glu | Val | Lys | Lys |
| | | | 20 | | | | | 25 | | | | | 30 | | |
| Pro | Gly | Ala | Ser | Val | Lys | Val | Ser | Cys | Lys | Ala | Ser | Gly | Tyr | Thr | Phe |
| | | 35 | | | | | 40 | | | | | 45 | | | |
| Thr | Asn | Tyr | Val | Met | His | Trp | Val | Arg | Gln | Ala | Pro | Gly | Gln | Arg | Leu |
| | 50 | | | | | 55 | | | | | 60 | | | | |
| Glu | Trp | Met | Gly | Phe | Ile | Asn | Pro | Ser | Asn | Asp | Gly | Pro | Lys | Tyr | Asn |
| 65 | | | | | 70 | | | | | 75 | | | | | 80 |
| Glu | Arg | Phe | Lys | Asn | Arg | Val | Thr | Ile | Thr | Ser | Asp | Thr | Ser | Ala | Ser |
| | | | | 85 | | | | | 90 | | | | | 95 | |
| Thr | Ala | Tyr | Met | Glu | Leu | Ser | Ser | Leu | Arg | Ser | Glu | Asp | Thr | Ala | Val |
| | | | 100 | | | | | 105 | | | | | 110 | | |
| Tyr | Tyr | Cys | Ala | Arg | Ala | Arg | Pro | Gly | Phe | Asp | Trp | Tyr | Phe | Asp | Val |
| | | 115 | | | | | 120 | | | | | 125 | | | |
| Trp | Gly | Gln | Gly | Thr | Leu | Val | Thr | Val | Ser | Ser | | | | | |
| 130 | | | | | 135 | | | | | | | | | | |

( 2 ) INFORMATION FOR SEQ ID NO:10:

(i) SEQUENCE CHARACTERISTICS:
    (A) LENGTH: 417 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 1..417

(ix) FEATURE:
    (A) NAME/KEY: misc_feature
    (B) LOCATION: 1..417
    (D) OTHER INFORMATION: /note= "Sequence encoding CY1748
    (PB1.3-Humanized) Heavy Chain-C Signal Peptide and
    Variable Region"

(xi) SEQUENCE DESCRIPTION: SEQ ID NO:10:

```
ATG GAG TTT GGG CTG AGC TGG CTT TTT CTT GTG GCT ATT TTA AAA GGT      48
Met Glu Phe Gly Leu Ser Trp Leu Phe Leu Val Ala Ile Leu Lys Gly
 1               5                  10                  15

GTC CAG TGT GAG GCC CAG CTG GTG CAG TCT GGA GCT GAG GTG AAA AAG      96
Val Gln Cys Glu Ala Gln Leu Val Gln Ser Gly Ala Glu Val Lys Lys
             20                  25                  30

CCT GGG GCT TCA GTG AAG GTG TCC TGC AAG GCT TCT GGA TAC ACA TTC     144
Pro Gly Ala Ser Val Lys Val Ser Cys Lys Ala Ser Gly Tyr Thr Phe
         35                  40                  45

ACC AAC TAT GTT ATG CAC TGG GTG CGC CAA GCT CCC GGG CAG AGG CTT     192
Thr Asn Tyr Val Met His Trp Val Arg Gln Ala Pro Gly Gln Arg Leu
     50                  55                  60

GAG TGG ATG GGA TTT ATT AAC CCA TCC AAT GAT GGT CCT AAG TAC AAT     240
Glu Trp Met Gly Phe Ile Asn Pro Ser Asn Asp Gly Pro Lys Tyr Asn
 65                  70                  75                  80

GAG AGG TTC AAA AAC AGG GTC ACA ATC ACT TCA GAC AAA TCC GCC AGC     288
Glu Arg Phe Lys Asn Arg Val Thr Ile Thr Ser Asp Lys Ser Ala Ser
                 85                  90                  95

ACC GCC TAC ATG GAA CTG TCC AGC CTG CGC TCC GAG GAC ACT GCA GTC     336
Thr Ala Tyr Met Glu Leu Ser Ser Leu Arg Ser Glu Asp Thr Ala Val
            100                 105                 110

TAT TAC TGT GCC AGA GCA CGC CCG GGG TTC GAC TGG TAC TTC GAT GTC     384
Tyr Tyr Cys Ala Arg Ala Arg Pro Gly Phe Asp Trp Tyr Phe Asp Val
        115                 120                 125

TGG GGA CAG GGT ACC CTT GTC ACC GTC AGT TCA                         417
Trp Gly Gln Gly Thr Leu Val Thr Val Ser Ser
    130                 135
```

(2) INFORMATION FOR SEQ ID NO:11:

(i) SEQUENCE CHARACTERISTICS:
        (A) LENGTH: 139 amino acids
        (B) TYPE: amino acid
        (D) TOPOLOGY: linear (ii) MOLECULE TYPE: protein (xi) SEQUENCE DESCRIPTION: SEQ ID NO:11:

```
Met Glu Phe Gly Leu Ser Trp Leu Phe Leu Val Ala Ile Leu Lys Gly
 1               5                  10                  15

Val Gln Cys Glu Ala Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Thr Asn Tyr Val Met His Trp Val Arg Gln Ala Pro Gly Gln Arg Leu
     50                  55                  60
```

```
Glu Trp Met Gly Phe Ile Asn Pro Ser Asn Asp Gly Pro Lys Tyr Asn
 65              70                  75                 80

Glu Arg Phe Lys Asn Arg Val Thr Ile Thr Ser Asp Lys Ser Ala Ser
                 85                  90                  95

Thr Ala Tyr Met Glu Leu Ser Ser Leu Arg Ser Glu Asp Thr Ala Val
                100             105                 110

Tyr Tyr Cys Ala Arg Ala Arg Pro Gly Phe Asp Trp Tyr Phe Asp Val
            115             120                 125

Trp Gly Gln Gly Thr Leu Val Thr Val Ser Ser
    130             135
```

(2) INFORMATION FOR SEQ ID NO:12:

(i) SEQUENCE CHARACTERISTICS:
       (A) LENGTH: 378 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 1..378

(ix) FEATURE:
       (A) NAME/KEY: misc_feature
       (B) LOCATION: 1..378
       (D) OTHER INFORMATION: /note= "Sequence encoding CY1748
           (PB1.3-Humanized)Light Chain-A Signal Peptide and
           Variable Region"

(xi) SEQUENCE DESCRIPTION: SEQ ID NO:12:

```
ATG GGA TGG AGC TGT ATC ATC CTC TTC TTG GTA GCA ACA GCT ACA GGT      48
Met Gly Trp Ser Cys Ile Ile Leu Phe Leu Val Ala Thr Ala Thr Gly
  1               5                  10                  15

GTC CAC TCC GAC ATC CAG ATG ACC CAG AGC CCA TCC ACC CTG TCT GCA      96
Val His Ser Asp Ile Gln Met Thr Gln Ser Pro Ser Thr Leu Ser Ala
                 20                  25                  30

AGC GTA GGA GAC AGA GTC ACC GTC ACC TGC AAG GCC AGT CAG AAT GTG     144
Ser Val Gly Asp Arg Val Thr Val Thr Cys Lys Ala Ser Gln Asn Val
             35                  40                  45

GCT ACT AAT GTA GTC TGG TAT CAA CAG AAA CCA GGA GAG GCT CCT AAA     192
Ala Thr Asn Val Val Trp Tyr Gln Gln Lys Pro Gly Glu Ala Pro Lys
         50                  55                  60

GCG CTT ATT TAT ACG GCA TCC TAC CGG TTC AGT GGA GTC CCT GAA CGC     240
Ala Leu Ile Tyr Thr Ala Ser Tyr Arg Phe Ser Gly Val Pro Glu Arg
 65                  70                  75                  80

TTC TCA GGC AGT GGA TCT GGG ACA GAT TTC ACT CTC ACC ATC AGC AGT     288
Phe Ser Gly Ser Gly Ser Gly Thr Asp Phe Thr Leu Thr Ile Ser Ser
                 85                  90                  95

CTG CAG TCT GAT GAC TTT GCA ACT TAT TAC TGT CAA CAG TAT AAC AAT     336
Leu Gln Ser Asp Asp Phe Ala Thr Tyr Tyr Cys Gln Gln Tyr Asn Asn
                100             105                 110

TAC CCA TAC ACG TTC GGC CAA GGG ACC AAG CTC GAA ATC AAA             378
Tyr Pro Tyr Thr Phe Gly Gln Gly Thr Lys Leu Glu Ile Lys
            115             120                 125
```

(2) INFORMATION FOR SEQ ID NO:13:

(i) SEQUENCE CHARACTERISTICS:
       (A) LENGTH: 126 amino acids
       (B) TYPE: amino acid
       (D) TOPOLOGY: linear ( i i ) MOLECULE TYPE: protein ( x i ) SEQUENCE DESCRIPTION: SEQ ID NO:13:

| Met | Gly | Trp | Ser | Cys | Ile | Ile | Leu | Phe | Leu | Val | Ala | Thr | Ala | Thr | Gly |
|---|---|---|---|---|---|---|---|---|---|---|---|---|---|---|---|
| 1 | | | | 5 | | | | | 10 | | | | | 15 | |

| Val | His | Ser | Asp | Ile | Gln | Met | Thr | Gln | Ser | Pro | Ser | Thr | Leu | Ser | Ala |
|---|---|---|---|---|---|---|---|---|---|---|---|---|---|---|---|
| | | | | 20 | | | | 25 | | | | | 30 | | |

| Ser | Val | Gly | Asp | Arg | Val | Thr | Val | Thr | Cys | Lys | Ala | Ser | Gln | Asn | Val |
|---|---|---|---|---|---|---|---|---|---|---|---|---|---|---|---|
| | | 35 | | | | 40 | | | | | 45 | | | | |

| Ala | Thr | Asn | Val | Val | Trp | Tyr | Gln | Gln | Lys | Pro | Gly | Glu | Ala | Pro | Lys |
|---|---|---|---|---|---|---|---|---|---|---|---|---|---|---|---|
| | 50 | | | | | 55 | | | | | | 60 | | | |

| Ala | Leu | Ile | Tyr | Thr | Ala | Ser | Tyr | Arg | Phe | Ser | Gly | Val | Pro | Glu | Arg |
|---|---|---|---|---|---|---|---|---|---|---|---|---|---|---|---|
| 65 | | | | | 70 | | | | | 75 | | | | | 80 |

| Phe | Ser | Gly | Ser | Gly | Ser | Gly | Thr | Asp | Phe | Thr | Leu | Thr | Ile | Ser | Ser |
|---|---|---|---|---|---|---|---|---|---|---|---|---|---|---|---|
| | | | | 85 | | | | | 90 | | | | | 95 | |

| Leu | Gln | Ser | Asp | Asp | Phe | Ala | Thr | Tyr | Tyr | Cys | Gln | Gln | Tyr | Asn | Asn |
|---|---|---|---|---|---|---|---|---|---|---|---|---|---|---|---|
| | | | 100 | | | | | 105 | | | | | 110 | | |

| Tyr | Pro | Tyr | Thr | Phe | Gly | Gln | Gly | Thr | Lys | Leu | Glu | Ile | Lys |
|---|---|---|---|---|---|---|---|---|---|---|---|---|---|
| | | 115 | | | | | 120 | | | | | 125 | |

( 2 ) INFORMATION FOR SEQ ID NO:14:

( i ) SEQUENCE CHARACTERISTICS:
        ( A ) LENGTH: 378 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..378

( i x ) FEATURE:
        ( A ) NAME/KEY: misc_feature
        ( B ) LOCATION: 1..378
        ( D ) OTHER INFORMATION: /note= "Sequence encoding
            CY1748(PB1.3- Humanized) Light Chain-B Signal Peptide
            and Variable Region"

( x i ) SEQUENCE DESCRIPTION: SEQ ID NO:14:

| ATG | GGA | TGG | AGC | TGT | ATC | ATC | CTC | TTC | TTG | GTA | GCA | ACA | GCT | ACA | GGT | 48 |
|---|---|---|---|---|---|---|---|---|---|---|---|---|---|---|---|---|
| Met | Gly | Trp | Ser | Cys | Ile | Ile | Leu | Phe | Leu | Val | Ala | Thr | Ala | Thr | Gly | |
| 1 | | | | 5 | | | | | 10 | | | | | 15 | | |

| GTC | CAC | TCC | GAC | ATC | CAG | ATG | ACC | CAG | AGC | CCA | TCC | ACC | CTG | TCT | GCA | 96 |
|---|---|---|---|---|---|---|---|---|---|---|---|---|---|---|---|---|
| Val | His | Ser | Asp | Ile | Gln | Met | Thr | Gln | Ser | Pro | Ser | Thr | Leu | Ser | Ala | |
| | | | | 20 | | | | 25 | | | | | 30 | | | |

| AGC | GTA | GGA | GAC | AGA | GTC | ACC | GTC | ACC | TGC | AAG | GCC | AGT | CAG | AAT | GTG | 144 |
|---|---|---|---|---|---|---|---|---|---|---|---|---|---|---|---|---|
| Ser | Val | Gly | Asp | Arg | Val | Thr | Val | Thr | Cys | Lys | Ala | Ser | Gln | Asn | Val | |
| | | 35 | | | | 40 | | | | | 45 | | | | | |

| GCT | ACT | AAT | GTA | GTC | TGG | TAT | CAA | CAG | AAA | CCA | GGA | GAG | GCT | CCT | AAA | 192 |
|---|---|---|---|---|---|---|---|---|---|---|---|---|---|---|---|---|
| Ala | Thr | Asn | Val | Val | Trp | Tyr | Gln | Gln | Lys | Pro | Gly | Glu | Ala | Pro | Lys | |
| | 50 | | | | | 55 | | | | | | 60 | | | | |

| GCG | CTT | ATT | TAT | ACG | GCA | TCC | TAC | CGG | TTC | AGT | GGA | GTC | CCT | TCA | CGC | 240 |
|---|---|---|---|---|---|---|---|---|---|---|---|---|---|---|---|---|
| Ala | Leu | Ile | Tyr | Thr | Ala | Ser | Tyr | Arg | Phe | Ser | Gly | Val | Pro | Ser | Arg | |
| 65 | | | | | 70 | | | | | 75 | | | | | 80 | |

| TTC | TCA | GGC | AGT | GGA | TCT | GGG | ACA | GAT | TTC | ACT | CTC | ACC | ATC | AGC | AGT | 288 |
|---|---|---|---|---|---|---|---|---|---|---|---|---|---|---|---|---|
| Phe | Ser | Gly | Ser | Gly | Ser | Gly | Thr | Asp | Phe | Thr | Leu | Thr | Ile | Ser | Ser | |
| | | | | 85 | | | | | 90 | | | | | 95 | | |

| CTG | CAG | TCT | GAT | GAC | TTT | GCA | ACT | TAT | TAC | TGT | CAA | CAG | TAT | AAC | AAT | 336 |
|---|---|---|---|---|---|---|---|---|---|---|---|---|---|---|---|---|
| Leu | Gln | Ser | Asp | Asp | Phe | Ala | Thr | Tyr | Tyr | Cys | Gln | Gln | Tyr | Asn | Asn | |
| | | | 100 | | | | | 105 | | | | | 110 | | | |

| | | | | | | | | | | | | | | | | |
|---|---|---|---|---|---|---|---|---|---|---|---|---|---|---|---|---|
| TAC | CCA | TAC | ACG | TTC | GGC | CAA | GGG | ACC | AAG | CTC | GAA | ATC | AAA | | | 378 |
| Tyr | Pro | Tyr | Thr | Phe | Gly | Gln | Gly | Thr | Lys | Leu | Glu | Ile | Lys | | | |
| | | 115 | | | | 120 | | | | | | 125 | | | | |

( 2 ) INFORMATION FOR SEQ ID NO:15:

( i ) SEQUENCE CHARACTERISTICS:
        ( A ) LENGTH: 126 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Met Gly Trp Ser Cys Ile Ile Leu Phe Leu Val Ala Thr Ala Thr Gly
 1               5                  10                  15

Val His Ser Asp Ile Gln Met Thr Gln Ser Pro Ser Thr Leu Ser Ala
             20                  25                  30

Ser Val Gly Asp Arg Val Thr Val Thr Cys Lys Ala Ser Gln Asn Val
         35                  40                  45

Ala Thr Asn Val Val Trp Tyr Gln Gln Lys Pro Gly Glu Ala Pro Lys
     50                  55                  60

Ala Leu Ile Tyr Thr Ala Ser Tyr Arg Phe Ser Gly Val Pro Ser Arg
 65                  70                  75                  80

Phe Ser Gly Ser Gly Ser Gly Thr Asp Phe Thr Leu Thr Ile Ser Ser
                 85                  90                  95

Leu Gln Ser Asp Asp Phe Ala Thr Tyr Tyr Cys Gln Gln Tyr Asn Asn
             100                 105                 110

Tyr Pro Tyr Thr Phe Gly Gln Gly Thr Lys Leu Glu Ile Lys
             115                 120                 125
```

( 2 ) INFORMATION FOR SEQ ID NO:16:

( i ) SEQUENCE CHARACTERISTICS:
        ( A ) LENGTH: 378 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..378

( i x ) FEATURE:
        ( A ) NAME/KEY: misc_feature
        ( B ) LOCATION: 1..378
        ( D ) OTHER INFORMATION: /note= "Sequence encoding
            CY1748(PB1.3- Humanized) Light Chain-C Signal Peptide
            and Variable Region"

( x i ) SEQUENCE DESCRIPTION: SEQ ID NO:16:

| | | | | | | | | | | | | | | | | |
|---|---|---|---|---|---|---|---|---|---|---|---|---|---|---|---|---|
| ATG | GGA | TGG | AGC | TGT | ATC | ATC | CTC | TTC | TTG | GTA | GCA | ACA | GCT | ACA | GGT | 48 |
| Met | Gly | Trp | Ser | Cys | Ile | Ile | Leu | Phe | Leu | Val | Ala | Thr | Ala | Thr | Gly | |
| 1 | | | | 5 | | | | | 10 | | | | | 15 | | |
| GTC | CAC | TCC | GAC | ATC | CAG | ATG | ACC | CAG | AGC | CCA | TCC | ACC | CTG | TCT | GCA | 96 |
| Val | His | Ser | Asp | Ile | Gln | Met | Thr | Gln | Ser | Pro | Ser | Thr | Leu | Ser | Ala | |
| | | | 20 | | | | | 25 | | | | | 30 | | | |
| AGC | GTA | GGA | GAC | AGA | GTC | ACC | GTC | ACC | TGC | AAG | GCC | AGT | CAG | AAT | GTG | 144 |
| Ser | Val | Gly | Asp | Arg | Val | Thr | Val | Thr | Cys | Lys | Ala | Ser | Gln | Asn | Val | |
| | | 35 | | | | | 40 | | | | | 45 | | | | |
| GCT | ACT | AAT | GTA | GTC | TGG | TAT | CAA | CAG | AAA | CCA | GGA | GAG | GCT | CCT | AAA | 192 |
| Ala | Thr | Asn | Val | Val | Trp | Tyr | Gln | Gln | Lys | Pro | Gly | Glu | Ala | Pro | Lys | |
| | 50 | | | | | 55 | | | | | 60 | | | | | |

```
GCG CTT ATT TAT ACG GCA TCC TAC CGG TTC AGT GGA GTC CCT GAA CGC       240
Ala Leu Ile Tyr Thr Ala Ser Tyr Arg Phe Ser Gly Val Pro Glu Arg
 65              70                  75                  80

TTC TCA GGC AGT GGA TCT GGG ACA GAA TTC ACT CTC ACC ATC AGC AGT       288
Phe Ser Gly Ser Gly Ser Gly Thr Glu Phe Thr Leu Thr Ile Ser Ser
                 85                  90                  95

CTG CAG TCT GAT GAC TTT GCA ACT TAT TAC TGT CAA CAG TAT AAC AAT       336
Leu Gln Ser Asp Asp Phe Ala Thr Tyr Tyr Cys Gln Gln Tyr Asn Asn
                100                 105                 110

TAC CCA TAC ACG TTC GGC CAA GGG ACC AAG CTC GAA ATC AAA               378
Tyr Pro Tyr Thr Phe Gly Gln Gly Thr Lys Leu Glu Ile Lys
        115                 120                 125
```

( 2 ) INFORMATION FOR SEQ ID NO:17:

( i ) SEQUENCE CHARACTERISTICS:
        ( A ) LENGTH: 126 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Met Gly Trp Ser Cys Ile Ile Leu Phe Leu Val Ala Thr Ala Thr Gly
 1               5                  10                  15

Val His Ser Asp Ile Gln Met Thr Gln Ser Pro Ser Thr Leu Ser Ala
                20                  25                  30

Ser Val Gly Asp Arg Val Thr Val Thr Cys Lys Ala Ser Gln Asn Val
                35                  40                  45

Ala Thr Asn Val Val Trp Tyr Gln Gln Lys Pro Gly Glu Ala Pro Lys
 50                  55                  60

Ala Leu Ile Tyr Thr Ala Ser Tyr Arg Phe Ser Gly Val Pro Glu Arg
 65              70                  75                  80

Phe Ser Gly Ser Gly Ser Gly Thr Glu Phe Thr Leu Thr Ile Ser Ser
                 85                  90                  95

Leu Gln Ser Asp Asp Phe Ala Thr Tyr Tyr Cys Gln Gln Tyr Asn Asn
                100                 105                 110

Tyr Pro Tyr Thr Phe Gly Gln Gly Thr Lys Leu Glu Ile Lys
        115                 120                 125
```

( 2 ) INFORMATION FOR SEQ ID NO:18:

( i ) SEQUENCE CHARACTERISTICS:
        ( A ) LENGTH: 378 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..378

( i x ) FEATURE:
        ( A ) NAME/KEY: misc_feature
        ( B ) LOCATION: 1..378
        ( D ) OTHER INFORMATION: /note= "CY1748 (PB13-Humanized)
        Light Chain- D Signal Peptide and Variable Region"

( x i ) SEQUENCE DESCRIPTION: SEQ ID NO:18:

```
ATG GGA TGG AGC TGT ATC ATC CTC TTC TTG GTA GCA ACA GCT ACA GGT        48
Met Gly Trp Ser Cys Ile Ile Leu Phe Leu Val Ala Thr Ala Thr Gly
 1               5                  10                  15

GTC CAC TCC GAC ATC CAG ATG ACC CAG AGC CCA TCC ACC CTG TCT GCA        96
```

```
Val His Ser Asp Ile Gln Met Thr Gln Ser Pro Ser Thr Leu Ser Ala
         20                  25                  30

AGC GTA GGA GAC AGA GTC ACC GTC ACC TGC AAG GCC AGT CAG AAT GTG      144
Ser Val Gly Asp Arg Val Thr Val Thr Cys Lys Ala Ser Gln Asn Val
         35                  40                  45

GCT ACT AAT GTA GTC TGG TAT CAA CAG AAA CCA GGA GAG GCT CCT AAA      192
Ala Thr Asn Val Val Trp Tyr Gln Gln Lys Pro Gly Glu Ala Pro Lys
    50                      55                  60

GCG CTT ATT TAT ACG GCA TCC TAC CGG TTC AGT GGA GTC CCT TCA CGC      240
Ala Leu Ile Tyr Thr Ala Ser Tyr Arg Phe Ser Gly Val Pro Ser Arg
65                      70                  75                  80

TTC TCA GGC AGT GGA TCT GGG ACA GAA TTC ACT CTC ACC ATC AGC AGT      288
Phe Ser Gly Ser Gly Ser Gly Thr Glu Phe Thr Leu Thr Ile Ser Ser
                85                  90                  95

CTG CAG TCT GAT GAC TTT GCA ACT TAT TAC TGT CAA CAG TAT AAC AAT      336
Leu Gln Ser Asp Asp Phe Ala Thr Tyr Tyr Cys Gln Gln Tyr Asn Asn
                100                 105                 110

TAC CCA TAC ACG TTC GGC CAA GGG ACC AAG CTC GAA ATC AAA              378
Tyr Pro Tyr Thr Phe Gly Gln Gly Thr Lys Leu Glu Ile Lys
            115                 120                 125
```

( 2 ) INFORMATION FOR SEQ ID NO:19:

( i ) SEQUENCE CHARACTERISTICS:
      ( A ) LENGTH: 126 amino acids
      ( B ) TYPE: amino acid
      ( D ) TOPOLOGY: linear ( i i ) MOLECULE TYPE: protein ( x i ) SEQUENCE DESCRIPTION: SEQ ID NO:19:

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Thr Leu Ser Ala
         20                  25                  30

Ser Val Gly Asp Arg Val Thr Val Thr Cys Lys Ala Ser Gln Asn Val
         35                  40                  45

Ala Thr Asn Val Val Trp Tyr Gln Gln Lys Pro Gly Glu Ala Pro Lys
    50                      55                  60

Ala Leu Ile Tyr Thr Ala Ser Tyr Arg Phe Ser Gly Val Pro Ser Arg
65                      70                  75                  80

Phe Ser Gly Ser Gly Ser Gly Thr Glu Phe Thr Leu Thr Ile Ser Ser
                85                  90                  95

Leu Gln Ser Asp Asp Phe Ala Thr Tyr Tyr Cys Gln Gln Tyr Asn Asn
                100                 105                 110

Tyr Pro Tyr Thr Phe Gly Gln Gly Thr Lys Leu Glu Ile Lys
            115                 120                 125
```

( 2 ) INFORMATION FOR SEQ ID NO:20:

( i ) SEQUENCE CHARACTERISTICS:
      ( A ) LENGTH: 62 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:20:

```
Cys Gln Asp Leu Pro Val Pro Asn Glu Ala Arg Val Asn Cys Ser His
1               5                   10                  15

Pro Phe Gly Ala Phe Arg Tyr Gln Ser Val Cys Ser Phe Thr Cys Asn
```

-continued

```
                        20                      25                         30
            Glu Gly Leu Leu Leu Val Gly Ala Ser Val Leu Gln Cys Leu Ala Thr
                    35                      40                      45
            Gly Asn Trp Asn Ser Val Pro Pro Glu Cys Gln Ala Ile Pro
                    50                      55                      60
```

( 2 ) INFORMATION FOR SEQ ID NO:21:

( i ) SEQUENCE CHARACTERISTICS:
        ( A ) LENGTH: 128 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..128
        ( D ) OTHER INFORMATION: /label=MOUSE_IIA ( x i ) SEQUENCE DESCRIPTION: SEQ ID NO:21:

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser Pro Gly Lys Ser Leu Glu Trp Ile
        35                  40                  45

Gly Asp Ile Asn Pro Asn Gly Gly Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Xaa Tyr Tyr Ser Ser Ser Tyr Met Xaa Ala Xaa Xaa Tyr
            100                 105                 110

Tyr Ala Phe Asp Tyr Trp Gly Gln Gly Thr Thr Val Thr Val Ser Ser
        115                 120                 125
```

( 2 ) INFORMATION FOR SEQ ID NO:22:

( i ) SEQUENCE CHARACTERISTICS:
        ( A ) LENGTH: 128 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..128
        ( D ) OTHER INFORMATION: /label=HUMAN_I ( x i ) SEQUENCE DESCRIPTION: SEQ ID NO:22:

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Ile Ser Trp Val Arg Gln Ala Pro Gly Gln Gly Leu Glu Trp Met
        35                  40                  45

Gly Trp Ile Asn Pro Tyr Gly Asn Gly Asp Thr Asn Tyr Ala Gln Lys
    50                  55                  60
```

```
Phe Gln Gly Arg Val Thr Ile Thr Ala Asp Thr Ser Thr Ser Thr Ala
 65                  70                  75                  80

Tyr Met Glu Leu Ser Ser Leu Arg Ser Glu Asp Thr Ala Val Tyr Tyr
                 85                  90                  95

Cys Ala Arg Ala Pro Gly Tyr Gly Ser Gly Gly Gly Cys Tyr Arg Gly
             100                 105                 110

Asp Tyr Phe Asp Tyr Trp Gly Gln Gly Thr Leu Val Thr Val Ser Ser
             115                 120                 125
```

( 2 ) INFORMATION FOR SEQ ID NO:23:

( i ) SEQUENCE CHARACTERISTICS:
      ( A ) LENGTH: 121 amino acids
      ( B ) TYPE: amino acid
      ( C ) STRANDEDNESS: single
      ( D ) TOPOLOGY: linear ( i i ) MOLECULE TYPE: protein ( i x ) FEATURE:
      ( A ) NAME/KEY: Protein
      ( B ) LOCATION: 1..121
      ( D ) OTHER INFORMATION: /label=HUMAN21/28'CL ( x i ) SEQUENCE DESCRIPTION: SEQ ID NO:23:

```
Pro Cys Ala Val Gln Leu Val Gln Ser Gly Ala Glu Val Lys Lys Pro
  1               5                  10                  15

Gly Ala Ser Val Lys Val Ser Cys Lys Ala Ser Gly Tyr Thr Phe Thr
             20                  25                  30

Ser Tyr Ala Met His Trp Val Arg Gln Ala Pro Gly Gln Arg Leu Glu
             35                  40                  45

Trp Met Gly Trp Ile Asn Ala Gly Asn Gly Asn Thr Lys Tyr Ser Gln
     50                  55                  60

Lys Phe Gln Gly Arg Val Thr Ile Thr Arg Asp Thr Ser Ala Ser Thr
 65                  70                  75                  80

Ala Tyr Met Glu Leu Ser Ser Leu Arg Ser Glu Asp Thr Ala Val Tyr
                 85                  90                  95

Tyr Cys Ala Arg Gly Gly Tyr Tyr Gly Ser Gly Ser Asn Tyr Trp Gly
             100                 105                 110

Gln Gly Thr Leu Val Thr Val Ser Ser
             115                 120
```

( 2 ) INFORMATION FOR SEQ ID NO:24:

( i ) SEQUENCE CHARACTERISTICS:
      ( A ) LENGTH: 108 amino acids
      ( B ) TYPE: amino acid
      ( C ) STRANDEDNESS: single
      ( D ) TOPOLOGY: linear ( i i ) MOLECULE TYPE: protein ( i x ) FEATURE:
      ( A ) NAME/KEY: Protein
      ( B ) LOCATION: 1..108
      ( D ) OTHER INFORMATION: /label=mouse_kappa-V ( x i ) SEQUENCE DESCRIPTION: SEQ ID NO:24:

```
Asp Ile Gln Met Thr Gln Ser Pro Ser Ser Leu Ser Ala Ser Leu Gly
  1               5                  10                  15

Asp Arg Val Thr Ile Thr Cys Arg Ala Ser Gln Asp Ile Ser Asn
             20                  25                  30

Tyr Leu Asn Trp Tyr Gln Gln Lys Pro Gly Gln Ser Pro Lys Leu Leu
             35                  40                  45
```

```
    Ile  Tyr  Tyr  Ala  Ser  Arg  Leu  His  Ser  Gly  Val  Pro  Ser  Arg  Phe  Ser
         50                    55                     60

Gly  Ser  Gly  Ser  Gly  Thr  Asp  Tyr  Ser  Leu  Thr  Ile  Ser  Asn  Leu  Glu
    65                       70                     75                          80

Gln  Glu  Asp  Ile  Ala  Thr  Tyr  Phe  Cys  Gln  Gln  Gly  Asn  Thr  Leu  Pro
                        85                     90                          95

Arg  Thr  Phe  Gly  Gly  Gly  Thr  Lys  Leu  Glu  Ile  Lys
                   100                    105
```

( 2 ) INFORMATION FOR SEQ ID NO:25:

( i ) SEQUENCE CHARACTERISTICS:
        ( A ) LENGTH: 114 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..114
        ( D ) OTHER INFORMATION: /label=human_kappa_1

( x i ) SEQUENCE DESCRIPTION: SEQ ID NO:25:

```
    Asp  Ile  Gln  Met  Thr  Gln  Ser  Pro  Ser  Ser  Leu  Ser  Ala  Ser  Val  Gly
    1                    5                     10                          15

Asp  Arg  Val  Thr  Ile  Thr  Cys  Arg  Ala  Ser  Gln  Ser  Leu  Val  Xaa  Xaa
                        20                     25                          30

Ser  Ile  Ser  Asn  Tyr  Leu  Ala  Trp  Tyr  Gln  Gln  Lys  Pro  Gly  Lys  Ala
                   35                     40                     45

Pro  Lys  Leu  Leu  Ile  Tyr  Ala  Ala  Ser  Ser  Leu  Glu  Ser  Gly  Val  Pro
         50                    55                     60

Ser  Arg  Phe  Ser  Gly  Ser  Gly  Ser  Gly  Thr  Asp  Phe  Thr  Leu  Thr  Ile
    65                       70                     75                          80

Ser  Ser  Leu  Gln  Pro  Glu  Asp  Phe  Ala  Thr  Tyr  Tyr  Cys  Gln  Gln  Tyr
                        85                     90                          95

Asn  Ser  Leu  Pro  Glu  Ile  Trp  Thr  Phe  Gly  Gln  Gly  Thr  Lys  Val  Glu
                   100                    105                    110

Ile  Lys
```

( 2 ) INFORMATION FOR SEQ ID NO:26:

( i ) SEQUENCE CHARACTERISTICS:
        ( A ) LENGTH: 106 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..106
        ( D ) OTHER INFORMATION: /label=human_DEN ( x i ) SEQUENCE DESCRIPTION: SEQ ID NO:26:

```
    Asp  Ile  Gln  Met  Thr  Gln  Ser  Pro  Ser  Thr  Leu  Ser  Ala  Ser  Val  Gly
    1                    5                     10                          15

Asp  Arg  Val  Thr  Ile  Thr  Cys  Arg  Thr  Ser  Gln  Ser  Ile  Ser  Arg  Trp
                        20                     25                          30

Leu  Ala  Trp  Tyr  Gln  Gln  Lys  Pro  Gly  Glu  Ala  Pro  Lys  Leu  Leu  Ile
                   35                     40                     45
```

-continued

```
    Tyr  Gly  Ala  Ser  Asn  Leu  Glu  Ser  Gly  Val  Pro  Arg  Phe  Ser  Gly  Ser
         50                       55                      60
    Gly  Ser  Gly  Thr  Glu  Phe  Thr  Leu  Thr  Ile  Ser  Ser  Leu  Gln  Ser  Asp
    65                       70                       75                      80
    Asp  Phe  Ala  Thr  Tyr  Tyr  Cys  Gln  Gln  Tyr  Asp  Ser  Phe  Pro  Tyr  Thr
                        85                       90                      95
    Phe  Gly  Gln  Gly  Thr  Lys  Leu  Glu  Ile  Lys
                   100                      105
```

( 2 ) INFORMATION FOR SEQ ID NO:27:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:27:

TTTCACAGTC CTGCATGC                                           18

( 2 ) INFORMATION FOR SEQ ID NO:28:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:28:

TGCTATGCCT TTGCAGGT                                           18

( 2 ) INFORMATION FOR SEQ ID NO:29:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:29:

CCTGATGGCT TCACACAT                                           18

( 2 ) INFORMATION FOR SEQ ID NO:30:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:30:

GGGAATGGCT TGGCATTC                                           18

( 2 ) INFORMATION FOR SEQ ID NO:31:

( i ) SEQUENCE CHARACTERISTICS:
        ( A ) LENGTH: 18 base pairs
        ( B ) TYPE: nucleic acid
        ( C ) STRANDEDNESS: single (D) TOPOLOGY: linear (ii) MOLECULE TYPE: DNA (primer)

(xi) SEQUENCE DESCRIPTION: SEQ ID NO:31:

CTGCAAAGCT TGACAGAC				18

(2) INFORMATION FOR SEQ ID NO:32:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:32:

CGAAATAGCC TCACAGGT				18

(2) INFORMATION FOR SEQ ID NO:33:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:33:

CTGCACAGCT TTACACAC				18

(2) INFORMATION FOR SEQ ID NO:34:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:34:

CTGGGCAGCT AAACACTG				18

(2) INFORMATION FOR SEQ ID NO:35:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:35:

AAACCTCCCA CACCCCCT				18

(2) INFORMATION FOR SEQ ID NO:36:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:36:

TGCACACCTT TGCTAAGC                                                                                            18

( 2 ) INFORMATION FOR SEQ ID NO:37:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: DNA (primer)

( x i ) SEQUENCE DESCRIPTION: SEQ ID NO:37:

CTGCAAAGCT TGACAGAC                                                                                            18

( 2 ) INFORMATION FOR SEQ ID NO:38:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:38:

Cys Arg Ala Val Lys Thr Ile Gln Glu Ala Leu Lys
 1               5                   10

( 2 ) INFORMATION FOR SEQ ID NO:39:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:39:

Cys Lys Gly Ile Ala Thr Ile Gln Glu Ala Leu Lys
 1               5                   10

( 2 ) INFORMATION FOR SEQ ID NO:40:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:40:

Cys Glu Ala Ile Lys Thr Ile Gln Glu Ala Leu Lys
 1               5                   10

( 2 ) INFORMATION FOR SEQ ID NO:41:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:41:

Cys Gln Ala Ile Pro Thr Ile Gln Glu Ala Leu Lys (2) INFORMATION FOR SEQ ID NO:42:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:42:

```
Cys Gln Ala Leu Gln Thr Ile Gln Glu Ala Leu Lys
1               5                   10
```

(2) INFORMATION FOR SEQ ID NO:43:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:43:

```
Cys Glu Ala Ile Ser Thr Ile Gln Glu Ala Leu Lys
1               5                   10
```

(2) INFORMATION FOR SEQ ID NO:44:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:44:

```
Cys Lys Ala Val Gln Thr Ile Gln Glu Ala Leu Lys
1               5                   10
```

(2) INFORMATION FOR SEQ ID NO:45:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:45:

```
Cys Leu Ala Ala Gln Thr Ile Gln Glu Ala Leu
1               5                   10
```

What is claimed is:

1. A P-selectin antibody that competitively inhibits the binding of an antibody secreted by a cell line designated ATCC Accession No. HB11041 to P-selectin as measured by a competitive inhibition assay, wherein the P-selectin antibody binds to P-selectin in the presence of a peptide CQNRYTDLVAIQNKNE (SEQ ID No. 1) and in the absence of calcium ion.

2. The P-selectin antibody of claim 1 that is an IgG antibody.

3. The P-selectin antibody of claim 1 that is a murine antibody.

4. The P-selectin antibody of claim 1 that is produced by a cell line designated ATCC Accession No. HB11041.

5. The P-selectin antibody of claim 1 that is a Fab, Fab' F(ab')$_2$, Fabc or Fv fragment.

6. The P-selectin antibody of claim 1 that allows thrombin-activated platelet aggregation in its presence.

7. A humanized P-selectin antibody comprising:

a. a humanized light chain comprising the complementarity determining regions (CDRs) having amino acid sequences corresponding to the CDRs of an immunoglobulin light chain in the P-selectin antibody of claim 1, and variable region framework regions corresponding to a set of human light chain variable region framework sequences and a human light chain constant region sequence; and b. a humanized heavy chain comprising the complementarity determining regions (CDRs) having amino acid sequences corresponding to the CDRs of an immunoglobulin heavy chain in the P-selectin antibody of claim 1, and variable region framework regions corresponding to a set of human heavy chain variable region framework sequences and a human heavy chain constant region sequence.

8. The humanized P-selectin antibody of claim 7, wherein the P-selectin antibody of claim 1 is produced by the cell line designated ATCC Accession No. HB11041.

9. The humanized P-selectin antibody of claim 8, wherein the human light chain variable region framework sequence is substituted in at least one position selected from a first group consisting of L21, L46, L60 and L70, by an amino acid present in the equivalent position of the immunoglobulin light chain variable region framework sequence in the antibody produced by the cell line designated ATCC Accession No. HB11041.

10. The humanized P-selectin antibody of claim 8, wherein the human heavy chain variable region framework sequence is substituted in at least one position selected from a second group consisting of H1, H2, H71 and H73, by an amino acid present in the equivalent position of the heavy chain variable region framework sequence in the antibody produced by the cell line designated ATCC Accession No. HB11041.

11. The humanized P-selectin antibody of claim 8, wherein:

a) the human light chain variable region framework sequence is substituted in at least one position selected from a first group consisting of L21, L46, L60 and L70, by an amino acid present in the equivalent position of the immunoglobulin light chain variable region framework sequence in the antibody produced by the cell line designated ATCC Accession No. HB11041; and b) the human heavy chain variable region framework sequence is substituted in at least one position selected from a second group consisting of H1, H2, H71 and H73, by an amino acid present in the equivalent position of the heavy chain variable region framework sequence in the antibody produced by the cell line designated ATCC Accession No. HB11041.

12. The humanized P-selectin antibody of claim 7, wherein the humanized heavy chain variable region framework sequences are 21/28'CL heavy chain variable region framework sequences.

13. The humanized P-selectin antibody of claim 7, wherein the humanized light chain variable region framework sequences are DEN light chain variable region framework sequences.

14. The humanized P-selectin antibody of claim 9, wherein the humanized light chain variable region framework sequences are substituted in at least two positions from the first group.

15. The humanized P-selectin antibody of claim 10, wherein the humanized heavy chain variable region framework sequences are substituted in at least two positions from the second group.

16. The humanized P-selectin antibody of claim 7, wherein the humanized light chain comprises the 1748RLA light chain variable region amino acid sequence shown in FIG. 14 (SEQ. ID. No. 13).

17. The humanized P-selectin antibody of claim 7, wherein the humanized light chain comprises the 1748RLB light chain variable region amino acid sequence shown in FIG. 15 (SEQ. ID. No. 15).

18. The humanized P-selectin antibody of claim 7, wherein the humanized light chain comprises the 1748RLC light chain variable region amino acid sequence shown in FIG. 16 (SEQ. ID. No. 17).

19. The humanized P-selectin antibody of claim 7, wherein the humanized light chain comprises the 1748RLD light chain variable region amino acid sequence shown in FIG. 17 (SEQ. ID. No. 19).

20. The humanized P-selectin antibody of claim 7, wherein the humanized heavy chain comprises the 1748RHA heavy chain variable region amino acid sequence shown in FIG. 11 (SEQ. ID. No. 7).

21. The humanized P-selectin antibody of claim 19, wherein the humanized heavy chain comprises the 1748RHB heavy chain variable region amino acid sequence shown in FIG. 12 (SEQ. ID. No. 9).

22. The humanized P-selectin antibody of claim 7, wherein the humanized heavy chain comprises the 1748RHC heavy chain variable region amino acid sequence shown in FIG. 13 (SEQ. ID. No. 11).

23. The humanized P-selectin antibody of claim 7, wherein the humanized heavy chain comprises the 1748RHB heavy chain variable region amino acid sequence shown in FIG. 12 (SEQ. ID. No. 9).

24. The humanized P-selectin antibody of claim 7 that is a Fab, Fab', F(ab')$_2$, Fabc or Fv fragment.

25. The humanized P-selectin antibody of claim 7, wherein the constant region sequence has an effector function.

26. The humanized P-selectin antibody of claim 25, wherein the effector function is capable of complement fixation or antibody dependent cytotoxicity.

27. The humanized P-selectin antibody of claim 7 wherein the constant region sequence lacks an effector function.

28. The humanized P-selectin antibody of claim 7, wherein the human light chain variable region framework sequences are from a human kappa light chain variable region framework sequence.

29. A composition comprising a carrier and the P-selectin antibody of claims 1, 2, 3, 4, 5, or 6.

30. A composition comprising a carrier and the humanized P-selectin antibody of claims 7, 8, 9, 10, or 11.

31. The composition of claim 30, wherein the humanized P-selectin antibody is a Fab fragment.

32. A P-selectin antibody that competitively inhibits the binding of an antibody secreted by a cell line designated ATCC Accession No. HB11041 to P-selectin as measured by a competitive inhibition assay, wherein the P-selectin antibody binds to P-selectin in the presence of a peptide CQNRYTDLVAIQNKNE (SEQ ID No. 1) and in the absence of calcium ion and the P-selectin antibody either:

a) inhibits P-selectin binding to neutrophils, monocytes or platelets;

b) inhibits binding of activated endothelial cells to neutrophils, monocytes or platelets; or c) inhibits binding of activated platelets to neutrophils or monocytes.

33. The P-selectin antibody of claim 32 that is an IgG antibody.

34. The P-selectin antibody of claim 32 that is a murine antibody.

35. The P-selectin antibody of claim 32 that is a Fab, Fab' F(ab')$_2$, Fabc or Fv fragment.

36. The P-selectin antibody of claim 32 that allows thrombin-activated platelet aggregation in its presence.

37. A humanized P-selectin antibody comprising:
   a. a humanized light chain comprising the complementarity determining regions (CDRs) having amino acid sequences corresponding to the CDRs of an immunoglobulin light chain in the P-selectin antibody of claim 32, and variable region framework regions corresponding to a set of human light chain variable region framework sequences and a human light chain constant region sequence; and
   b. a humanized heavy chain comprising the complementarity determining regions (CDRs) having amino acid sequences corresponding to the CDRs of an immunoglobulin heavy chain in the P-selectin antibody of claim 32, and variable region framework regions corresponding to a set of human heavy chain variable region framework sequences and a human heavy chain constant region sequence.

38. A composition comprising the P-selectin antibody of claim 32 and a carrier.

39. A composition comprising the humanized P-selectin antibody of claim 37 and a carrier.

40. A method of treating ischemia-reperfusion injury comprising administering to a patient a therapeutically effective dose of the P-selectin antibody of claim 32.

41. The method of claim 40, wherein the P-selectin antibody is IgG$_1$.

42. The method of claim 40, wherein the P-selectin antibody is murine.

43. The method of claim 42, wherein the P-selectin antibody is produced by the cell line designated as ATCC Accession No. HB11041.

44. The method of claim 40, wherein the patient is suffering from thrombotic, epidermal, myocardial, renal, cerebral, splenic, hepatic, spinal, splanchnic, pulmonary, partial-body, or whole-body ischemia.

45. A method of treating acute lung injury comprising administering to a patient a therapeutically effective dose of the P-selectin antibody of claim 32.

46. A method of treating ischemia-reperfusion injury comprising administering to a patient a therapeutically effective amount of the humanized P-selectin antibody of claim 37.

47. The method of claim 46, wherein the patient is suffering from thrombotic, epidermal, myocardial, renal, cerebral, splenic, hepatic, spinal, splanchnic, pulmonary, partial-body, or whole-body ischemia.

48. A method of treating acute lung injury comprising administering to a patient in need thereof a therapeutically effective dose of the pharmaceutical composition of claim 37.

49. A method for detecting P-selectin, the method comprising:
   administering the P-selectin antibody of claim 32 to a patient or a tissue sample therefrom; and
   detecting complexes formed by specific binding between the P-selectin antibody and P-selectin present in the target sample.

50. A method for detecting P-selectin, the method comprising:
   administering the humanized P-selectin antibody of claim 37 to a patient or a tissue sample therefrom; and
   detecting complexes formed by specific binding between the P-selectin antibody and P-selectin present in the target sample.

51. A cell line expressing the P-selectin antibody of claim 1.

52. A composition comprising a cell line designated ATCC Accession No. HB11041.

53. A stable cell line comprising:
   a nucleic acid segment encoding the heavy chain of the humanized P-selectin antibody of claim 7, the segment operably linked to a promoter to allow expression of the heavy chain; and
   a second nucleic acid segment encoding the light chain of the humanized P-selectin antibody of claim 7, the second segment operably linked to a second promoter to allow expression of the light chain;
   wherein the stable cell line is capable of producing the humanized P-selectin antibody of claim 7.

54. The cell line of claim 7 that is capable of producing about 30 μg of the humanized immunoglobulin/$10^6$ cells/day.

55. The cell line of claim 7, designated as ATCC Accession No. CRL 11596.

56. A nucleic acid encoding the heavy chain of the humanized P-selectin antibody of claim 7.

57. A nucleic acid encoding the light chain of the humanized P-selectin antibody of claim 7.

* * * * *